United States Patent
Kakinuma et al.

(10) Patent No.: US 12,006,382 B2
(45) Date of Patent: Jun. 11, 2024

(54) (METH)ACRYLATE, MONOMER COMPOSITION FOR DENTAL MATERIAL, MOLDED BODY, COMPOSITION FOR DENTAL MATERIAL, DENTAL MATERIAL, AND METHOD OF MANUFACTURING (METH)ACRYLATE

(71) Applicant: MITSUI CHEMICALS, INC., Tokyo (JP)

(72) Inventors: Naoyuki Kakinuma, Ichihara (JP); Eri Koizumi, Ichihara (JP)

(73) Assignee: MITSUI CHEMICALS, INC., Tokyo (JP)

(*) Notice: Subject to any disclaimer, the term of this patent is extended or adjusted under 35 U.S.C. 154(b) by 717 days.

(21) Appl. No.: 16/973,576

(22) PCT Filed: Aug. 20, 2019

(86) PCT No.: PCT/JP2019/032456
§ 371 (c)(1),
(2) Date: Dec. 9, 2020

(87) PCT Pub. No.: WO2020/040141
PCT Pub. Date: Feb. 27, 2020

(65) Prior Publication Data
US 2021/0246239 A1    Aug. 12, 2021

(30) Foreign Application Priority Data

Aug. 21, 2018  (JP) .............................. 2018-154941
Aug. 21, 2018  (JP) .............................. 2018-154942
Aug. 21, 2018  (JP) .............................. 2018-154943

(51) Int. Cl.
*C08F 20/38* (2006.01)
*A61K 6/887* (2020.01)

(52) U.S. Cl.
CPC .............. *C08F 20/38* (2013.01); *A61K 6/887* (2020.01)

(58) Field of Classification Search
CPC ....................................... C08F 20/38
See application file for complete search history.

(56) References Cited

U.S. PATENT DOCUMENTS

2004/0039080 A1    2/2004  Honda et al.

FOREIGN PATENT DOCUMENTS

| JP | S64-026505 A | 1/1989 | |
|---|---|---|---|
| JP | H01-313410 A | 12/1989 | |
| JP | H11315059 A | 11/1999 | |
| JP | 2000204069 A | 7/2000 | |
| JP | 2013213200 A * | 10/2013 | ............... C08F 2/48 |
| JP | 2013213200 A | 10/2013 | |
| JP | 2013544823 A | 12/2013 | |

(Continued)

OTHER PUBLICATIONS

Machine-generated English-language translation of JP-2013213200-A.*

(Continued)

*Primary Examiner* — Vu A Nguyen
(74) *Attorney, Agent, or Firm* — BUCHANAN, INGERSOLL & ROONEY PC

(57) ABSTRACT

A (meth)acrylate includes a reaction product of a thiol compound containing two or more thiol groups, and a (meth)acrylate compound containing two or more (meth) acryloyloxy groups.

10 Claims, 50 Drawing Sheets

(56) References Cited

FOREIGN PATENT DOCUMENTS

| JP | 2015196685 A | 11/2015 |
| JP | 2018021102 A | 2/2018 |
| WO | 0234207 A1 | 5/2002 |
| WO | 2012157566 A1 | 11/2012 |

OTHER PUBLICATIONS

Shin et al., Macromolecules 2009, 42, 3294-3301.*
Gimbert et al., Tetrahedron 61 (2005) 8598-8605.*
International Search Report (PCT/ISA/210) issued on Oct. 8, 2019, by the Japanese Patent Office as the International Searching Authority for International Application No. PCT/JP2019/032456.
Written Opinion (PCT/ISA/237) issued on Oct. 8, 2019, by the Japanese Patent Office as the International Searching Authority for International Application No. PCT/JP2019/032456.

* cited by examiner

(METH)ACRYLATE, MONOMER COMPOSITION FOR DENTAL MATERIAL, MOLDED BODY, COMPOSITION FOR DENTAL MATERIAL, DENTAL MATERIAL, AND METHOD OF MANUFACTURING (METH)ACRYLATE

TECHNICAL FIELD

The present invention relates to a (meth)acrylate, a monomer composition for a dental material, a molded body, a composition for a dental material, a dental material, and a method of manufacturing a (meth)acrylate

BACKGROUND ART

A composite resin, which is a representative example of a composition for a dental material, typically contains a monomer composition containing a monomer, a filler, a polymerization initiator, a polymerization inhibitor, a dye and the like. In recent years, a composite resin having a higher mechanical property has been demanded, and the physical property of the cured product of the monomer composition contained in the composite resin has a great influence on the physical property of the cured product of the composite resin containing the monomer composition. Therefore, various studies have been made on the monomer which is the main component of the monomer composition, and for example, polyfunctional (meth)acrylates as shown in Patent Literature 1 to 4 are known as monomers.

[Patent Literature 1] Japanese National-Phase Publication (JP-A) No. 2000-204069
[Patent Literature 2] JP-A No. 2013-544823
[Patent Literature 3] JP-A No. H11-315059
[Patent Literature 4] WO. 2012/157566

SUMMARY OF INVENTION

Technical Problem

As described above, in order to expand the applicable range of the composition for a dental material containing a monomer such as a composite resin, it is necessary to improve the mechanical property of the cured product. Therefore, there is a demand for a (meth)acrylate that can be used singly or in combination with other polymerizable compound to obtain a cured product having excellent mechanical property.

One aspect of the present invention is made in view of the above problem, and an object thereof is to provide a (meth)acrylate, a method of manufacturing thereof, a monomer composition for a dental material, and a composition for a dental material, capable of manufacturing a cured product with an excellent mechanical property, and a molded body and a dental material, with an excellent mechanical property.

Solution to Problem

Examples of the first means for solving the above problem include the following <1A> to <12A>.
Examples of the second means for solving the above problem include the following <1B> to <12B>.
Examples of the third means for solving the above problem include the following <1C> to <10C>.

<1A> A monomer composition for a dental material comprising a reaction product of a thiol compound (1) containing two or more thiol groups, and a (meth)acrylate compound (2) containing two or more (meth)acryloyloxy groups.

<2A> The monomer composition for a dental material according to <1A>, wherein the reaction product comprises a structure formed by reacting the thiol groups contained in the thiol compound (1) and the (meth)acryloyloxy groups contained in the (meth)acrylate compound (2).

<3A> The monomer composition for a dental material according to <1A>, wherein a ratio (b/a) of a mass b in the (meth)acrylate compound (2) with respect to a mass a in the thiol compound (1) is in a range of from 0.5 to 35.

<4A> The monomer composition for a dental material according to any one of <1A> to <3A>, wherein the thiol compound (1) is at least one selected from the group consisting of 1,4-butandithiol, 1,8-octanedithiol, 3,6-dioxa-1,8-octanedithiol, 3,7-dithia-1,9-nonanedithiol, 1,4-butanediol bis(thioglycolate), bis(3-mercaptopropionic acid)ethylene glycol, 1,4-bis(3-mercaptobutyryloxy)butane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, 4-mercaptomethyl-1,8-dimercapto-3,6-dithiaoctane, 1,1,3,3-tetrakis(mercaptomethylthio)propane, trimethylrol propane tris(3-mercaptopropionate), pentaerythritol tetrakis(2-mercaptoacetate), pentaerythritol tetrakis(3-mercaptopropionate) and tris-[(3-mercaptopropionyloxy)-ethyl]-isocyanurate.

<5A> The monomer composition for a dental material according to any one of <1A> to <4A>, wherein the (meth)acrylate compound (2) is at least one selected from the group consisting of neopentyl di(meth)acrylate, 1,4-butanediol di(meth)acrylate, 1,6-hexanediol di(meth)acrylate, 1,8-octanediol di(meth)acrylate, 1,9-nonanediol di(meth)acrylate, 1,10-decanediol di(meth)acrylate, tricyclodecanedimethanol di(meth)acrylate, ethylene glycol di(meth)acrylate, diethylene glycol di(meth)acrylate, triethylene glycol di(meth)acrylate, tetraethylene glycol di(meth)acrylate, polyethylene glycol di(meth)acrylate, tripropylene glycol di(meth)acrylate, tetrapropylene glycol di(meth)acrylate, polypropylene glycol di(meth)acrylate, 2,2-bis[4-(3-(meth)acryloyloxy-2-hydroxypropoxy)phenyl]propane, ethylene oxide-modified bisphenol A di(meth)acrylate, and propylene oxide-modified bisphenol A di(meth)acrylate.

<6A> The monomer composition for a dental material according to any one of <1A> to <5A>, wherein the reaction product does not contain a thiol group, and contains a (meth)acryloyloxy group.

<7A> The monomer composition for a dental material comprising a sulfide bond and an ester bond.

<8A> The monomer composition for a dental material according to any one of <1A> to <7A>, wherein the (meth)acrylate (A) comprises a structure represented by the following general formula (B).

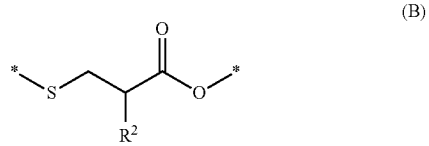

In the general formula (B), R² represents a hydrogen atom or a methyl group; and each * represents a binding site.

<9A> The monomer composition for a dental material according to any one of <1A> to <8A>, comprising a (meth)acrylate (B) comprising a (meth)acrylate other than the (meth)acrylate (A).

<10A> A molded body comprising a cured product of the monomer composition for a dental material according to any one of <1A> to <9A>.

<11A> A composition for a dental material comprising the monomer composition according to any one of <1A> to <9A>, a polymerization initiator, and a filler.

<12A> A dental material comprising a cured product of the composition for a dental material according to <11 A>.

<1B> A (meth)acrylate represented by the following general formula (1).

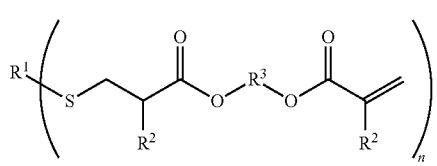

(1)

In the general formula (1), R¹ represents a residue of a bifunctional to tetrafunctional thiol compound from which all thiol groups have been removed; R² represents a hydrogen atom or a methyl group; R³ represents a residue of a di(meth)acrylate from which two (meth)acryloyloxy groups have been removed; n is an integer from 2 to 4; and plural instances of R² and R³ may be the same or different, respectively.

<2B> The (meth)acrylate according to <1B>, wherein the thiol compound has 2 to 20 carbon atoms and comprises at least one bond selected from a sulfide bond, an ester bond, an ether bond, and an alkylene group.

<3B> The (meth)acrylate according to <1B> or <2B>, wherein a molecular weight of the R¹ is from 100 to 500 in the general formula (1).

<4B> The (meth)acrylate according to any one of <1B> to <3B>, wherein the R¹ is a group represented by the following formula (2), (3), (4), (5), (6-1), (6-2), (6-3), (7), (8), (9) or (10) in the general formula (1).

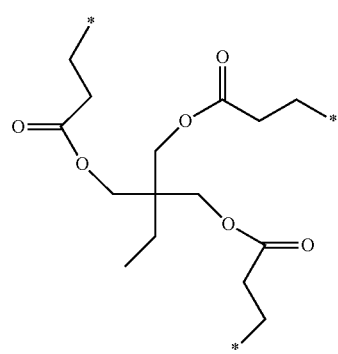

(2)

-continued

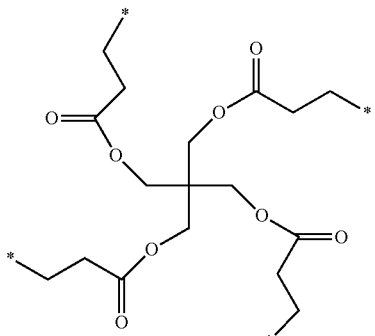

(3)

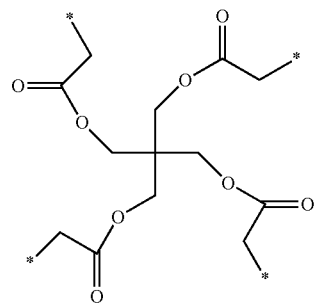

(4)

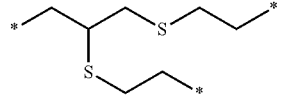

(5)

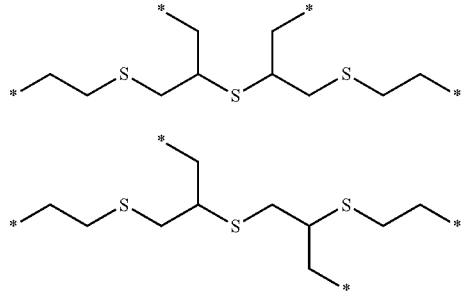

(6-1)

(6-2)

(6-3)

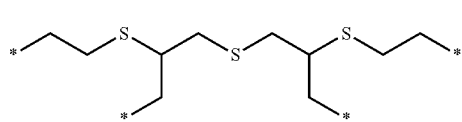

(7)

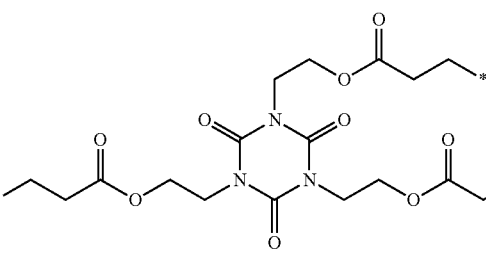

(8)

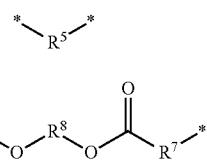

(9)

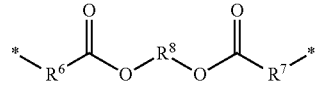

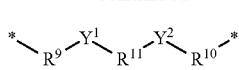

In formulae (2), (3), (4), (5), (6-1), (6-2), (6-3), (7), (8), (9) and (10), each * represents a binding site; in formula (8), $R^5$ represents a divalent hydrocarbon group having 1 to 10 carbon atoms; in formula (9), $R^6$, $R^7$, and $R^8$ each independently represent a divalent hydrocarbon group having 1 to 10 carbon atoms; in formula (10), $R^9$, $R^{10}$, and $R^{11}$ each independently represent a divalent hydrocarbon group having 1 to 10 carbon atoms; and $Y^1$ and $Y^2$ each independently represent an oxygen atom or a sulfur atom.

<5B> The (meth)acrylate according to any one of <1B> to <4B>, wherein the $R^3$ comprises at least one group selected from the group consisting of a linear or branched divalent acyclic hydrocarbon group having 1 to 50 carbon atoms, a divalent cyclic hydrocarbon group having 3 to 50 carbon atoms, and a divalent organic group having 1 to 50 carbon atoms, and containing an oxygen atom in a main chain, in the general formula (1).

<6B> The (meth)acrylate according to any one of <1B> to <5B>, wherein the (meth)acrylate is neopentyl di(meth)acrylate, 1,4-butanediol di(meth)acrylate, 1,6-hexanediol di(meth)acrylate, 1,8-octanediol di(meth)acrylate, 1,9-nonanediol di(meth)acrylate, 1,10-decanediol di(meth)acrylate, tricyclodecanedimethanol di(meth)acrylate, ethylene glycol di(meth)acrylate, diethylene glycol di(meth)acrylate, triethylene glycol di(meth)acrylate, tetraethylene glycol di(meth)acrylate, polyethylene glycol di(meth)acrylate, tripropylene glycol di(meth)acrylate, tetrapropylene glycol di(meth)acrylate, polypropylene glycol di(meth)acrylate, 2,2-bis[4-(3-(meth)acryloyloxy-2-hydroxypropoxy)phenyl]propane, ethylene oxide-modified bisphenol A di(meth)acrylate, or propylene oxide-modified bisphenol A di(meth)acrylate.

<7B> The (meth)acrylate according to any one of <1B> to <5B>, having a viscosity at 25° C. of from 1 mPa·s to 10,000 mPa·s.

<8B> A monomer composition comprising a (meth)acrylate (A) comprising the (meth)acrylate according to any one of <1B> to <6B>, and a (meth)acrylate (B) comprising a (meth)acrylate other than the (meth)acrylate (A).

<9B> The monomer composition according to <8B>, wherein the (meth)acrylate (B) is a (meth)acrylate represented by the following general formula (A).

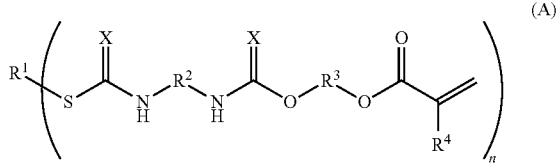

In the general formula (A), $R^1$ represents a residue of a bifunctional to tetrafunctional thiol compound from which all thiol groups have been removed; $R^2$ represents a residue of an iso(thio)cyanate compound from which all iso(thio)cyanate groups have been removed; $R^3$ represents a residue of a (meth)acrylate containing a hydroxy group from which a (meth)acryloyloxy group and the hydroxy group have been removed; and $R^4$ represents a hydrogen atom or a methyl group. X represents an oxygen atom or a sulfur atom. n is an integer from 2 to 4. Plural instances of $R^2$ to $R^4$ may be the same or different, respectively.

<10B> A molded body comprising a cured product of the monomer composition according to <8B> or <9B>.

<11B> A composition for a dental material comprising the monomer composition according to <8B> or <9B>, a polymerization initiator, and a filler.

<12B> A dental material comprising a cured product of the composition for a dental material according to <11B>.

<1C> A method of manufacturing a (meth)acrylate, the method comprising: a step of preparing a composition comprising a thiol compound (1) containing two or more thiol groups, a (meth)acrylate compound (2) containing two or more (meth)acryloyloxy groups, and an alkylphosphine compound (5); and a step of producing a (meth)acrylate (A) containing a sulfide bond by reacting the thiol compound (1) and the (meth)acrylate compound (2).

<2C> The method of manufacturing the (meth)acrylate according to <1C>, wherein a content of the alkylphosphine compound (5) is 0.2 parts by mass or less with respect to 100 parts by mass of the composition.

<3C> The method of manufacturing the (meth)acrylate according to <1C> or <2C>, wherein a reaction temperature of the thiol compound (1) and the (meth)acrylate compound (2) is 50° C. or less in the step of producing the (meth)acrylate (A).

<4C> The method of manufacturing the (meth)acrylate according to any one of <1C> to <3C>, wherein the alkylphosphine compound (5) comprises a trialkylphosphine compound.

<5C> The method of manufacturing the (meth)acrylate according to <4C>, wherein the trialkylphosphine compound comprises at least one selected from the group consisting of tri-n-butylphosphine, tri-n-hexylphosphine, tricyclohexylphosphine and tri-n-octylphosphine.

<6C> The method of manufacturing the (meth)acrylate according to any one of <1C> to <5C>, wherein the (meth)acrylate (A) does not contain a thiol group.

<7C> The method of manufacturing the (meth)acrylate according to any one of <1C> to <6C>, wherein the (meth)acrylate (A) comprises a structure represented by the following general formula (B).

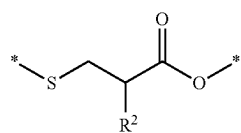

In general formula (B), $R^2$ represents a hydrogen atom or a methyl group. Each * represents a binding site.

<8C> A method of manufacturing a monomer composition comprising a step of preparing the (meth)acrylate (A) by the method of manufacturing the (meth)acrylate according to any one of <1C> to <7C>, and a step of producing a monomer composition by mixing the (meth)acrylate (A), and a (meth)acrylate (B) comprising a (meth)acrylate other than the (meth)acrylate (A).

<9C> A method of manufacturing a composition for a dental material comprising a step of preparing the (meth)acrylate (A) by the method of manufacturing the (meth)acrylate according to any one of <1C> to <7C>, and a step of producing a composition for a dental material by mixing the (meth)acrylate (A), a (meth) acrylate (B) comprising a (meth)acrylate other than the (meth)acrylate (A), a polymerization initiator, and a filler.

<10C> A method of manufacturing a dental material comprising a step of preparing a composition for a dental material by the method of manufacturing the composition for a dental material according to <9C>, and a step of producing a dental material by curing the composition for a dental material.

Advantageous Effects of Invention

One aspect of the present invention enables to provide a (meth)acrylate, a method of manufacturing thereof, a monomer composition for a dental material, and a composition for a dental material, capable of manufacturing a cured product with an excellent mechanical property, and a molded body and a dental material, with an excellent mechanical property.

DESCRIPTION OF EMBODIMENTS

Mode for Carrying Out the Invention

Figure 1:
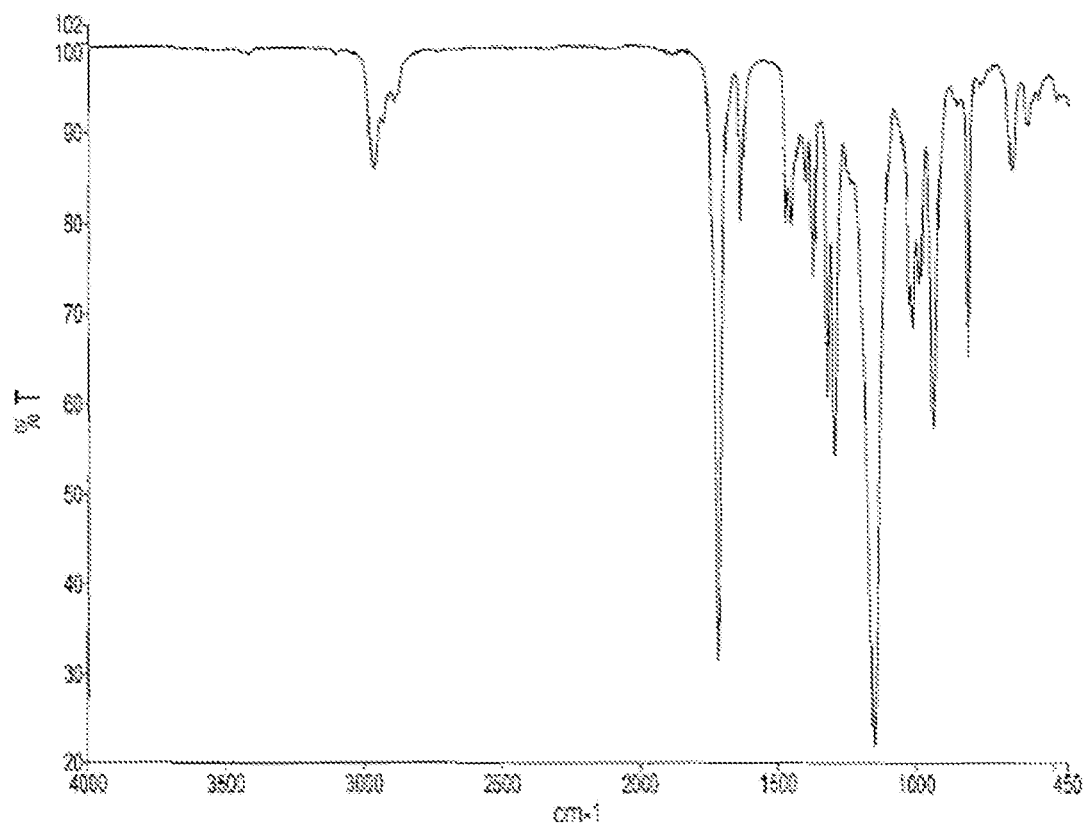
FIG. 1 shows IR spectrum of ene-thiol methacrylate (A-1) obtained in Example 1A.
Figure 2:
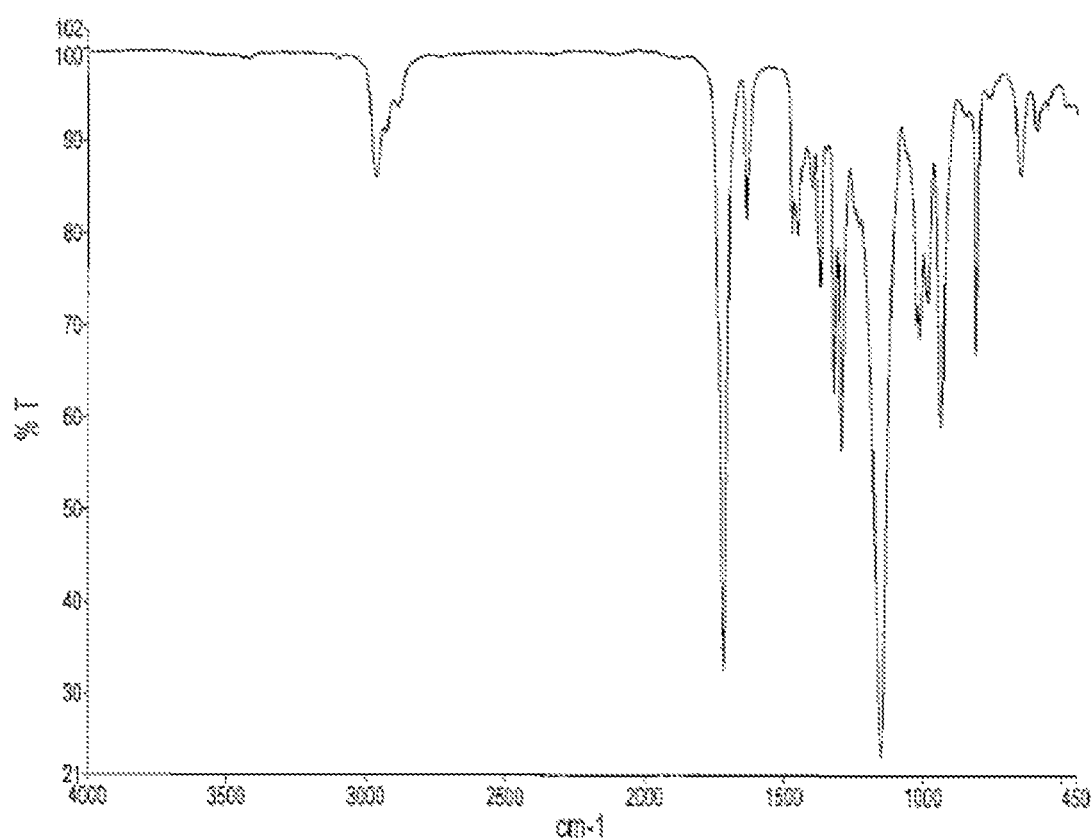
FIG. 2 shows IR spectrum of ene-thiol methacrylate (A-2) obtained in Example 2A.
Figure 3:
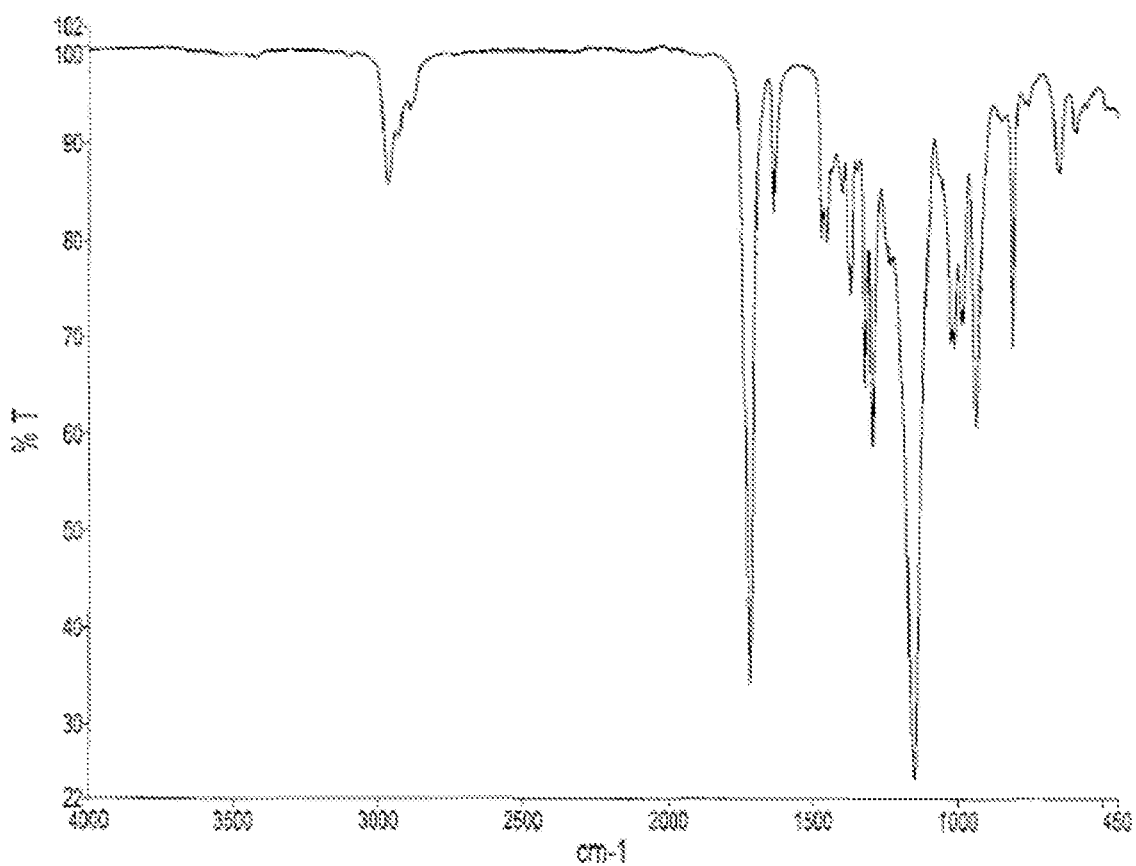
FIG. 3 shows IR spectrum of ene-thiol methacrylate (A-3) obtained in Example 3A.
Figure 4:
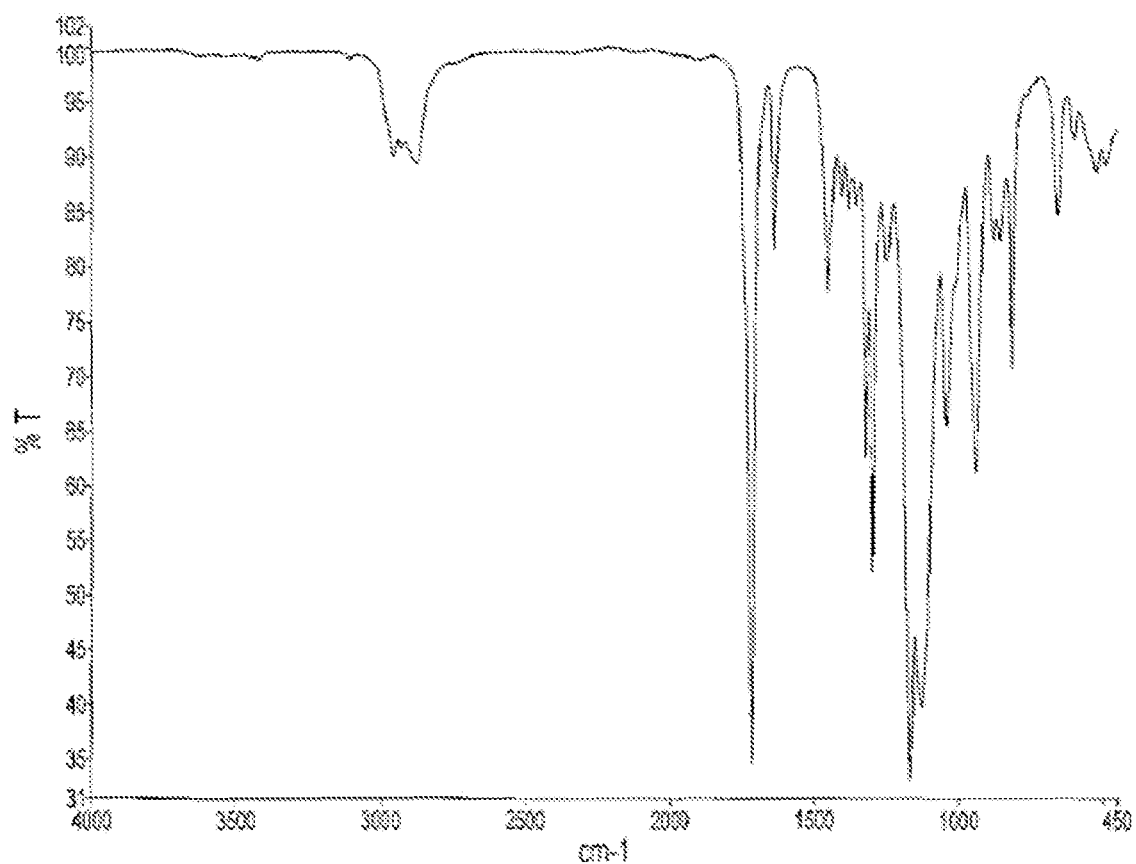
FIG. 4 shows IR spectrum of ene-thiol methacrylate (A-4) obtained in Example 4A.
Figure 5:
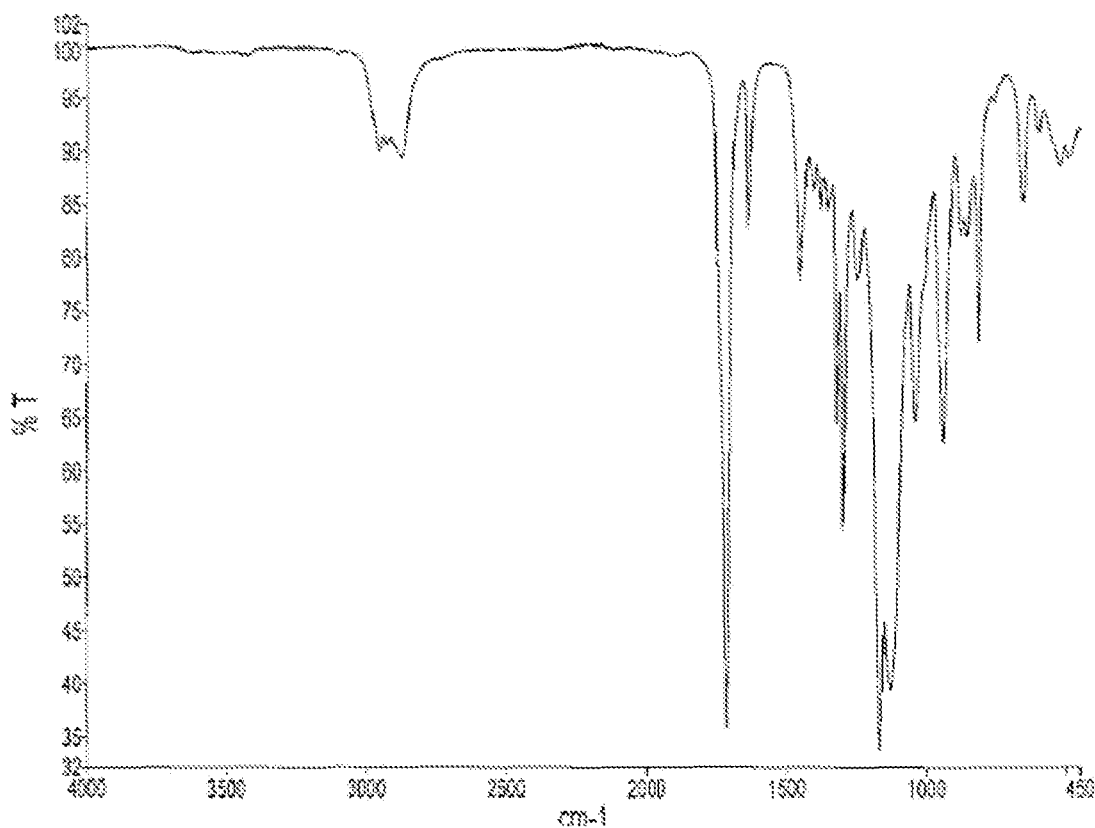
FIG. 5 shows IR spectrum of ene-thiol methacrylate (A-5) obtained in Example 5A.
Figure 6:
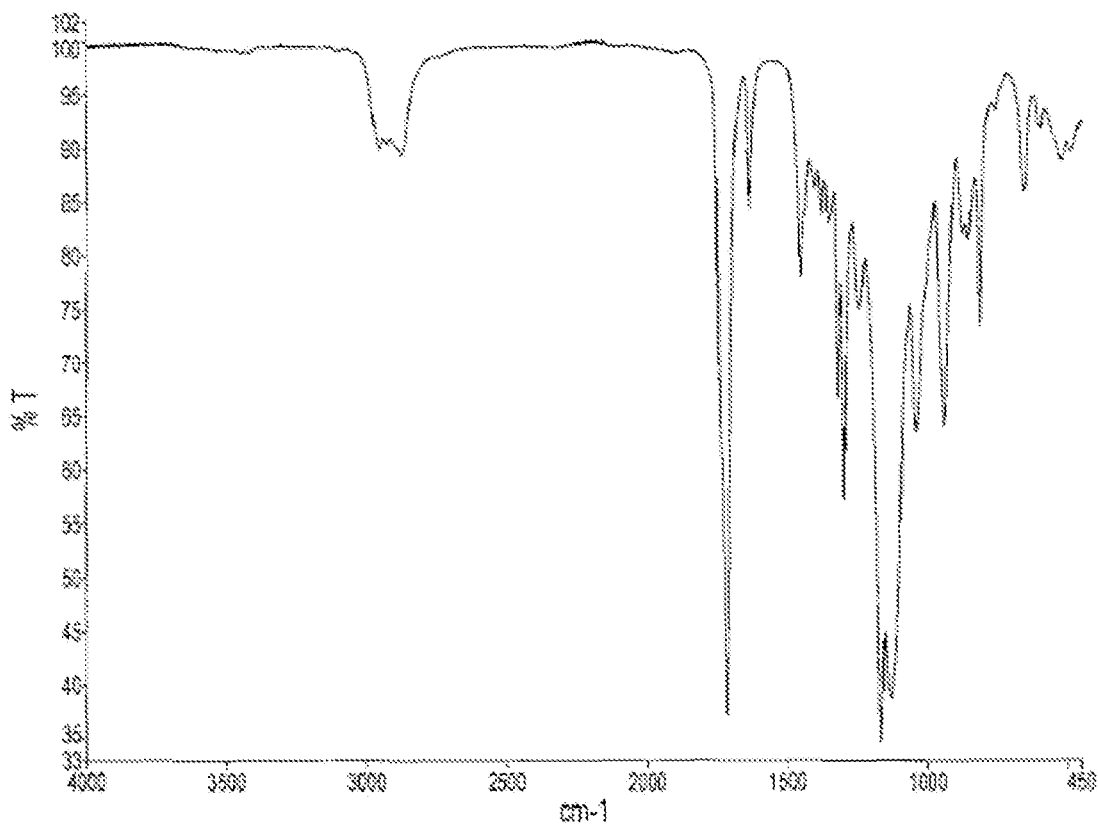
FIG. 6 shows IR spectrum of ene-thiol methacrylate (A-6) obtained in Example 6A.
Figure 7:
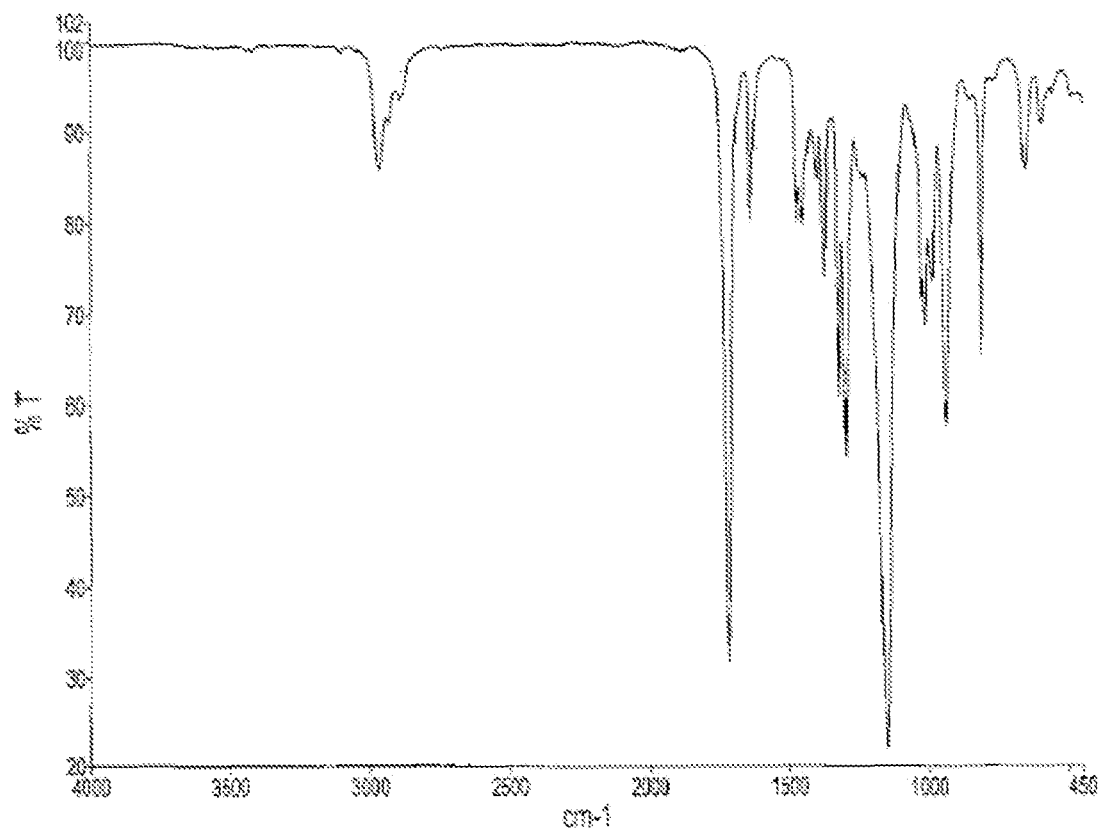
FIG. 7 shows IR spectrum of ene-thiol methacrylate (A-7) obtained in Example 7A.
Figure 8:
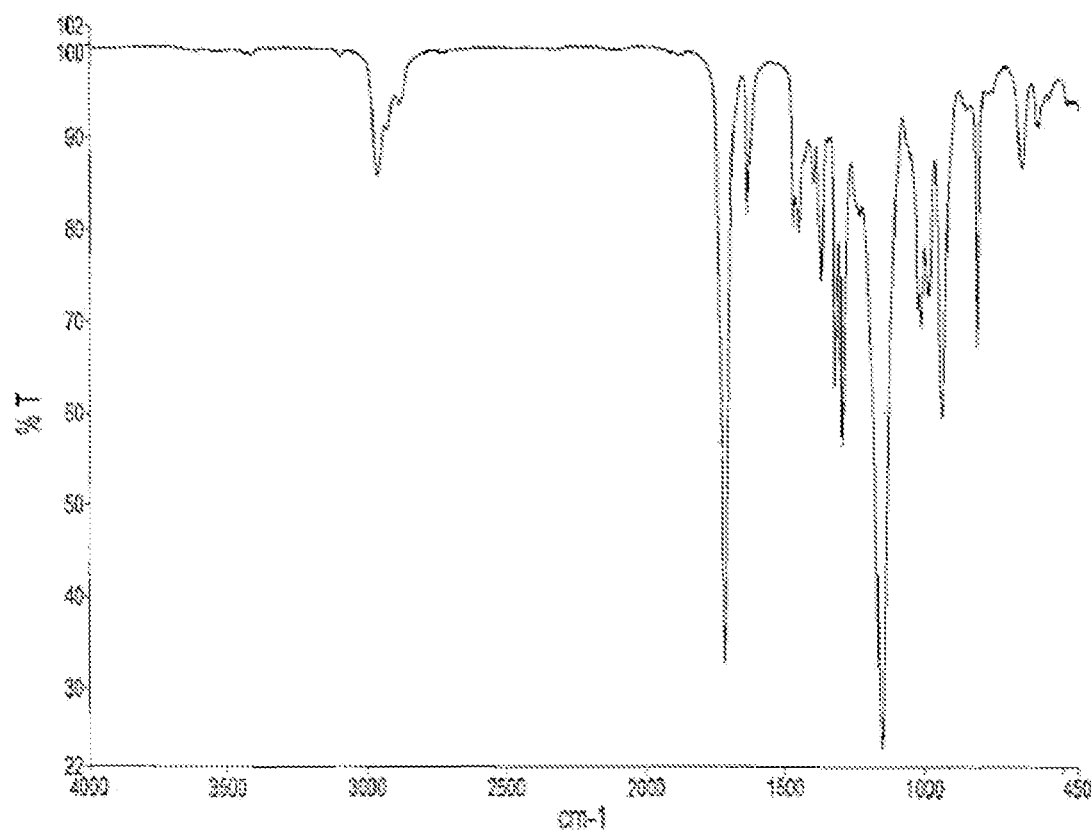
FIG. 8 shows IR spectrum of ene-thiol methacrylate (A-8) obtained in Example 8A.
Figure 9:
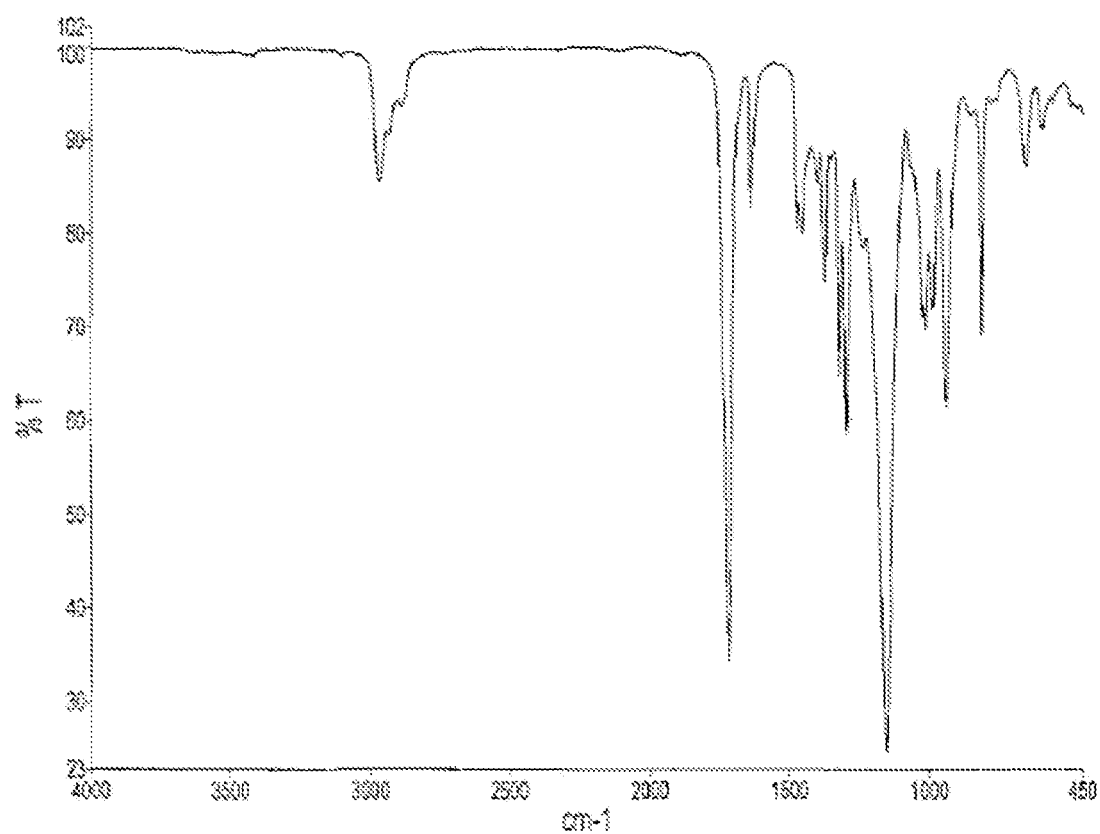
FIG. 9 shows IR spectrum of ene-thiol methacrylate (A-9) obtained in Example 9A.
Figure 10:
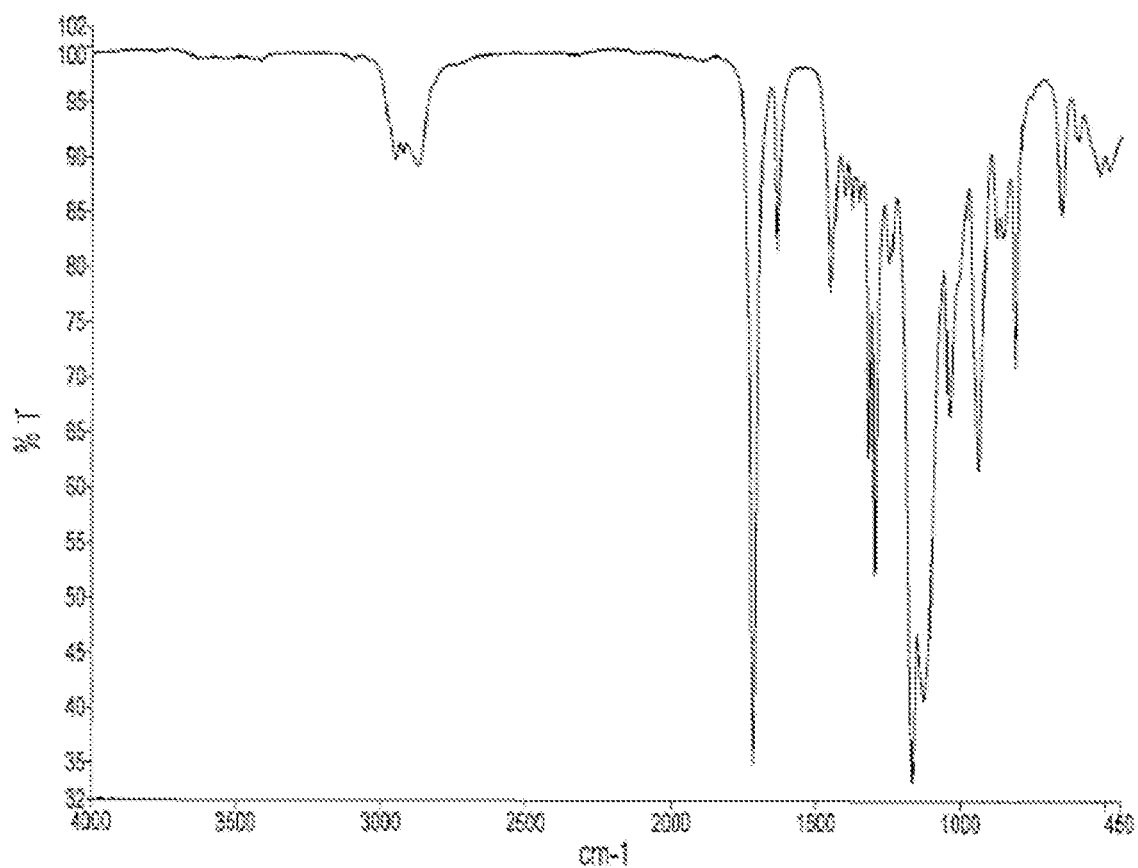
FIG. 10 shows IR spectrum of ene-thiol methacrylate (A-10) obtained in Example 10A.
Figure 11:
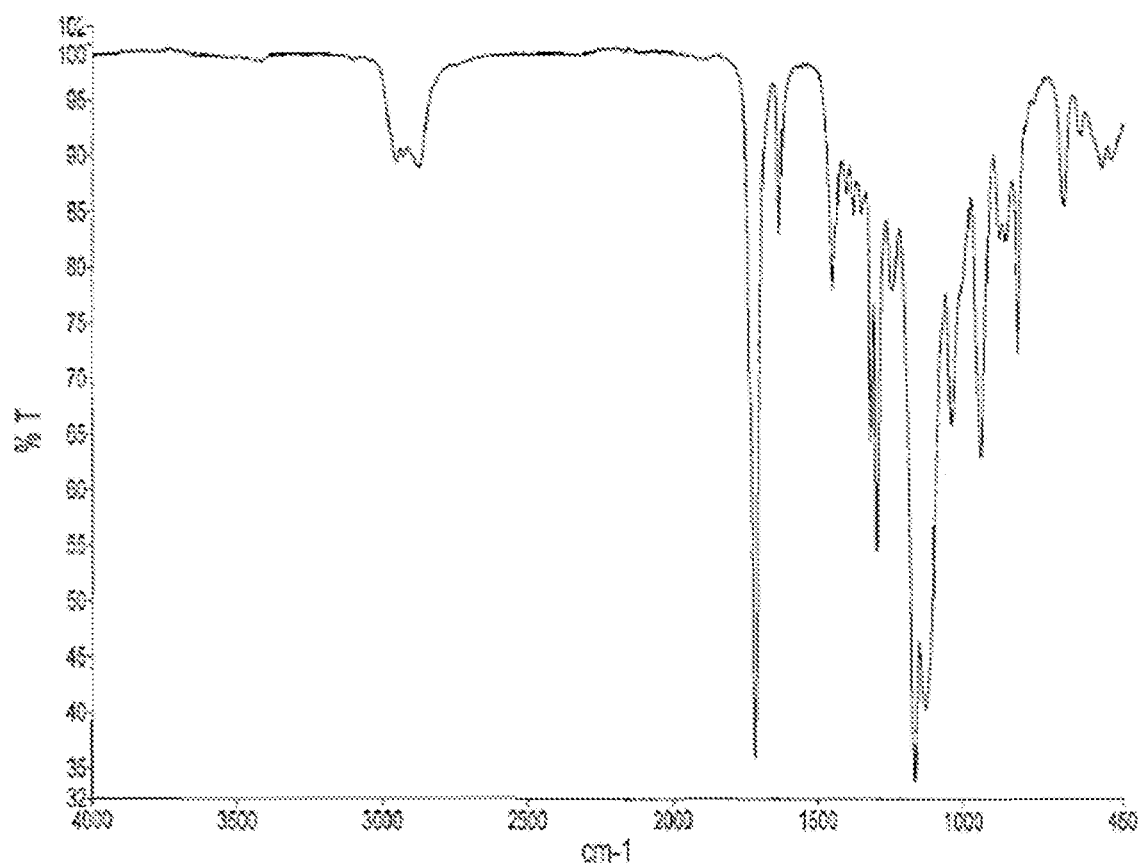
FIG. 11 shows IR spectrum of ene-thiol methacrylate (A-11) obtained in Example 11A.
Figure 12:
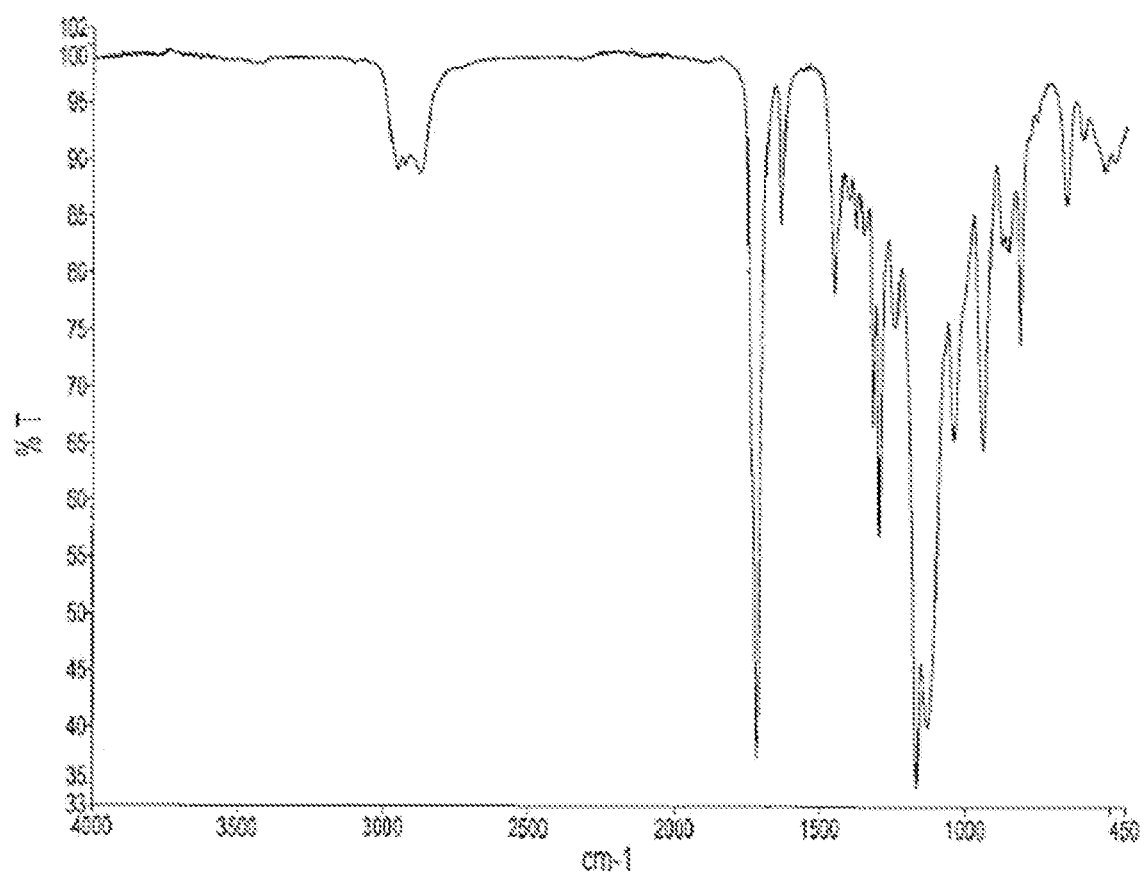
FIG. 12 shows IR spectrum of ene-thiol methacrylate (A-12) obtained in Example 12A.
Figure 13:
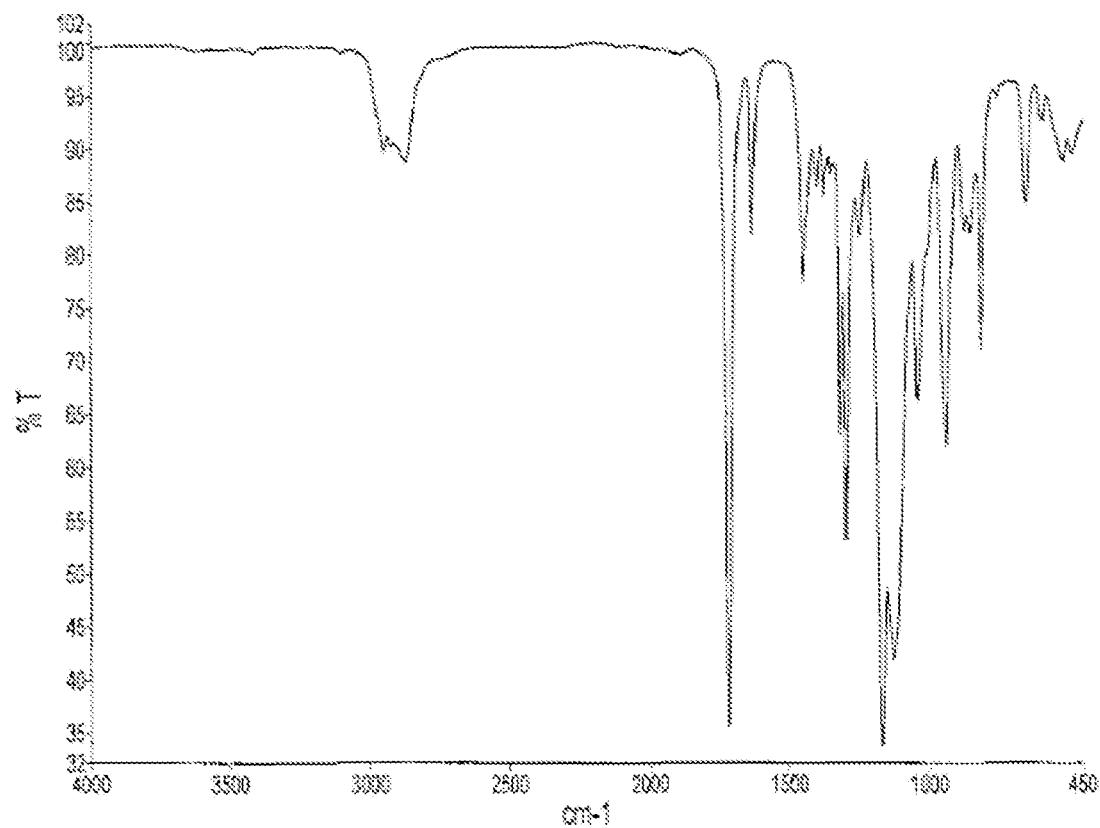
FIG. 13 shows IR spectrum of ene-thiol methacrylate (A-13) obtained in Example 13A.
Figure 14:
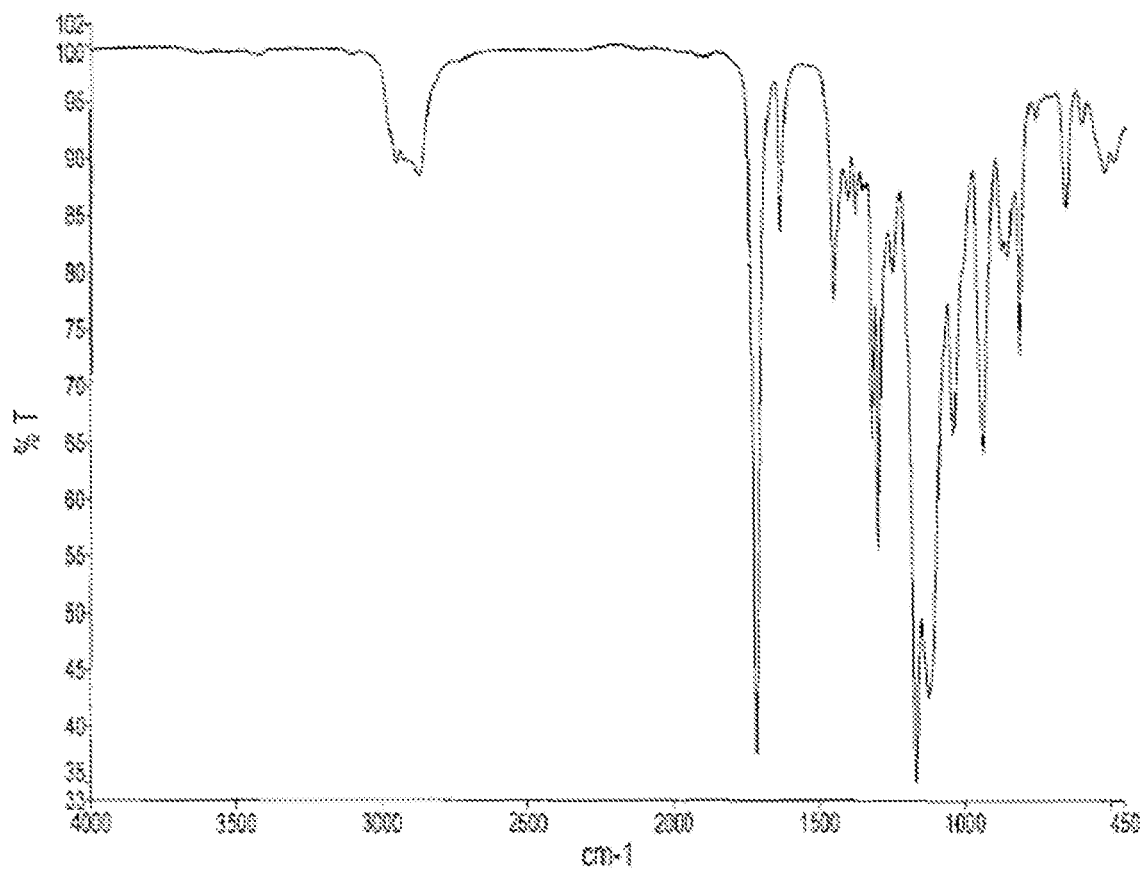
FIG. 14 shows IR spectrum of ene-thiol methacrylate (A-14) obtained in Example 14A.
Figure 15:
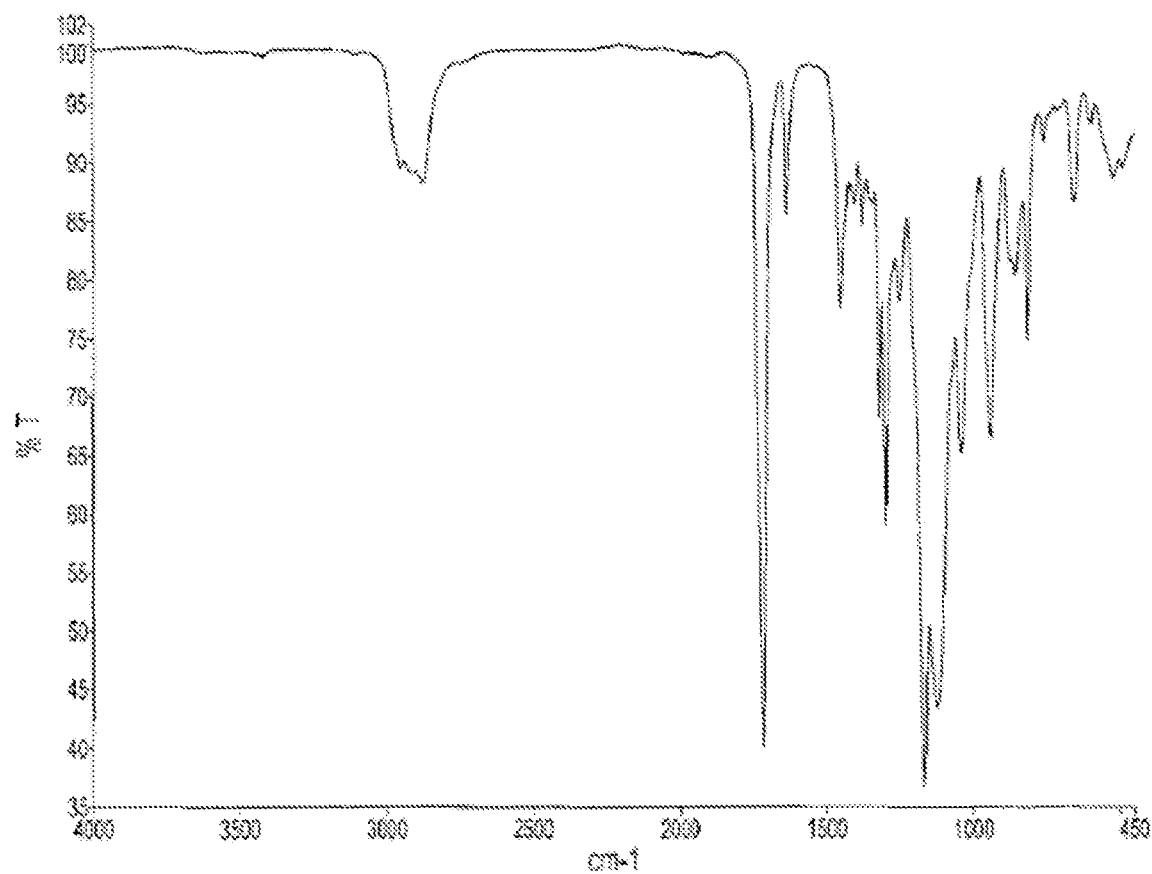
FIG. 15 shows IR spectrum of ene-thiol methacrylate (A-15) obtained in Example 15A.
Figure 16:
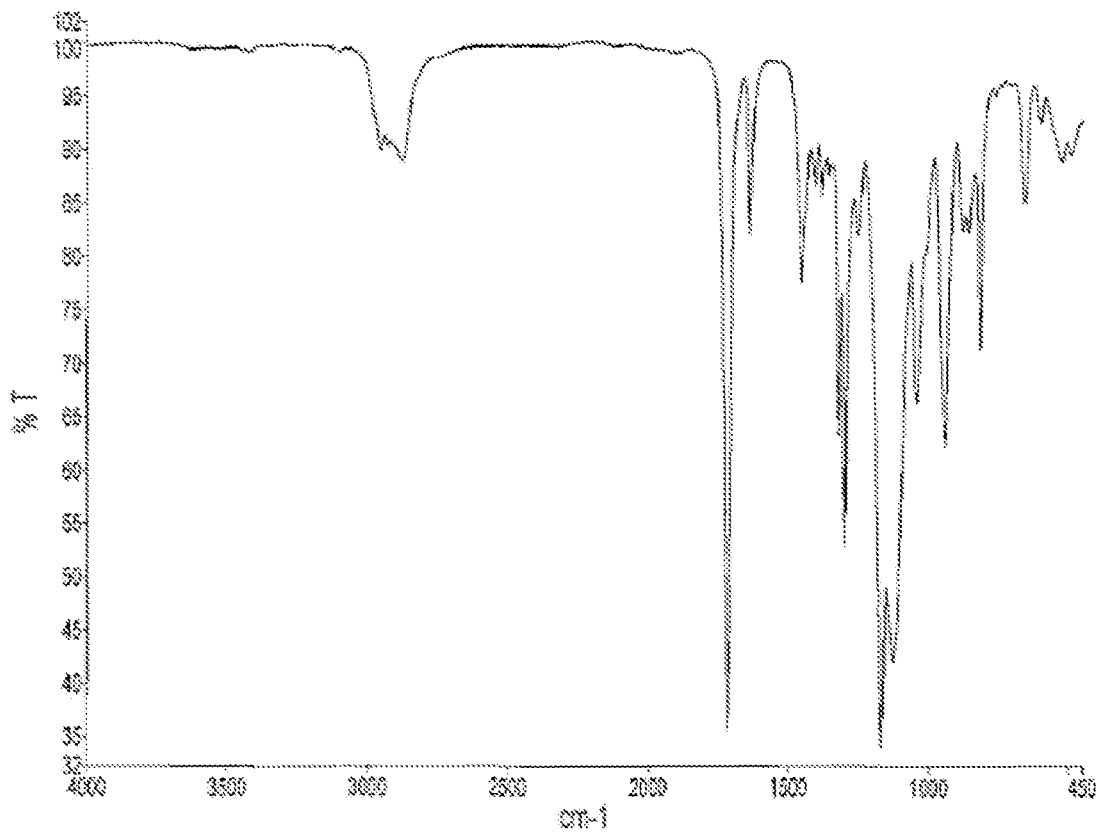
FIG. 16 shows IR spectrum of ene-thiol methacrylate (A-16) obtained in Example 16A.
Figure 17:
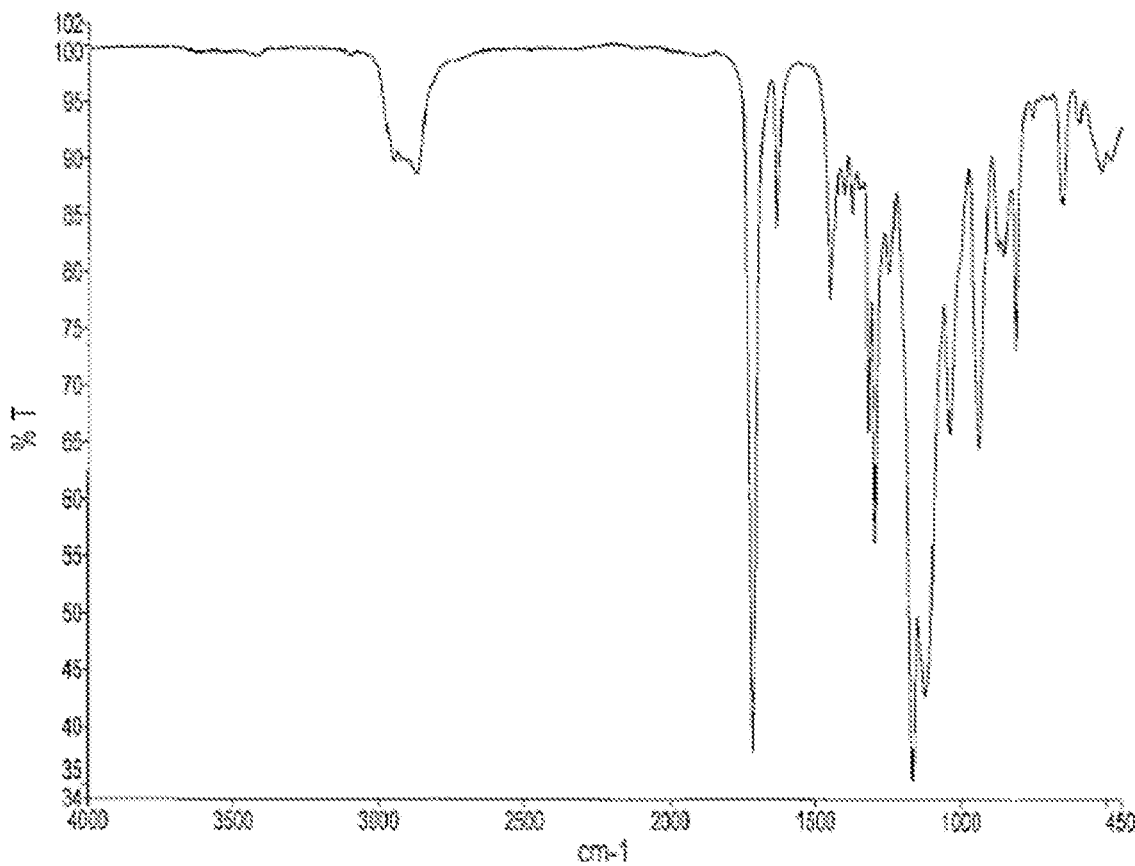
FIG. 17 shows IR spectrum of ene-thiol methacrylate (A-17) obtained in Example 17A.
Figure 18:
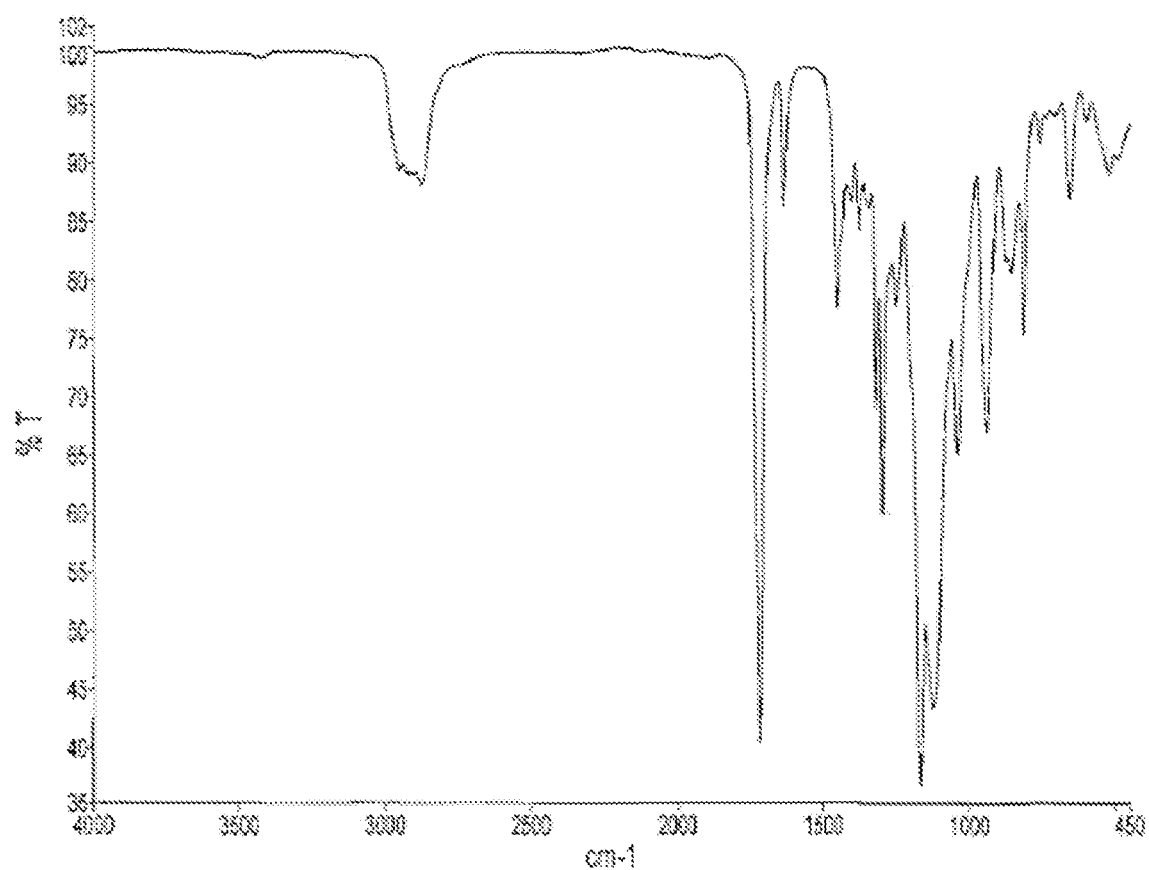
FIG. 18 shows IR spectrum of ene-thiol methacrylate (A-18) obtained in Example 18A.
Figure 19:
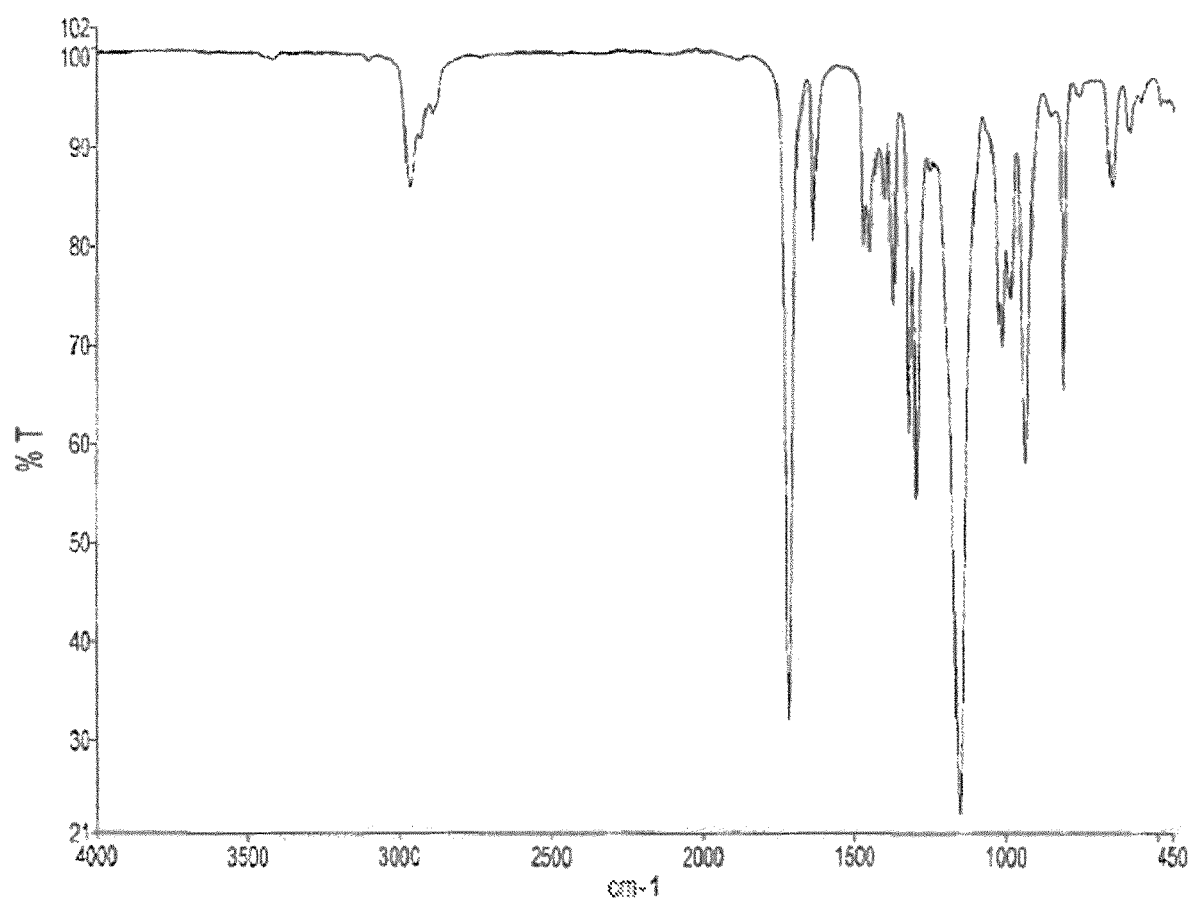
FIG. 19 shows IR spectrum of ene-thiol methacrylate (A-19) obtained in Example 19A.
Figure 20:
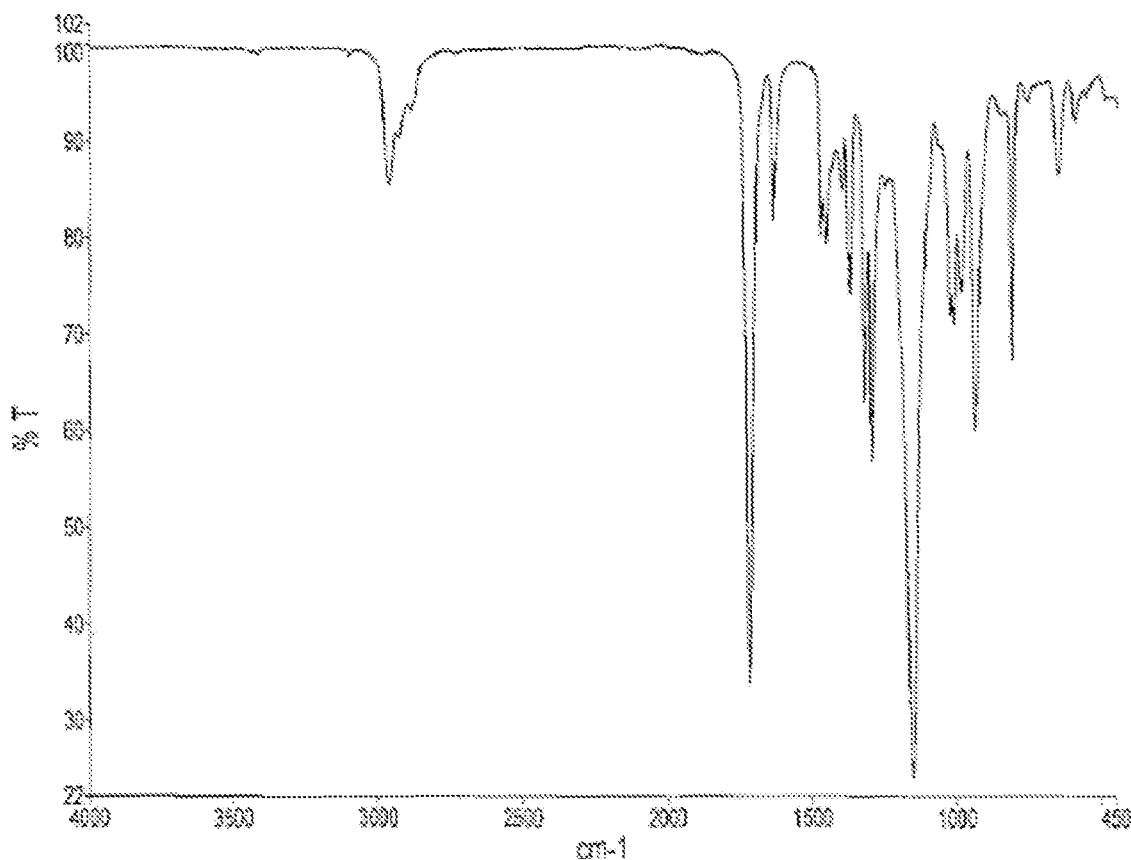
FIG. 20 shows IR spectrum of ene-thiol methacrylate (A-20) obtained in Example 20A.
Figure 21:
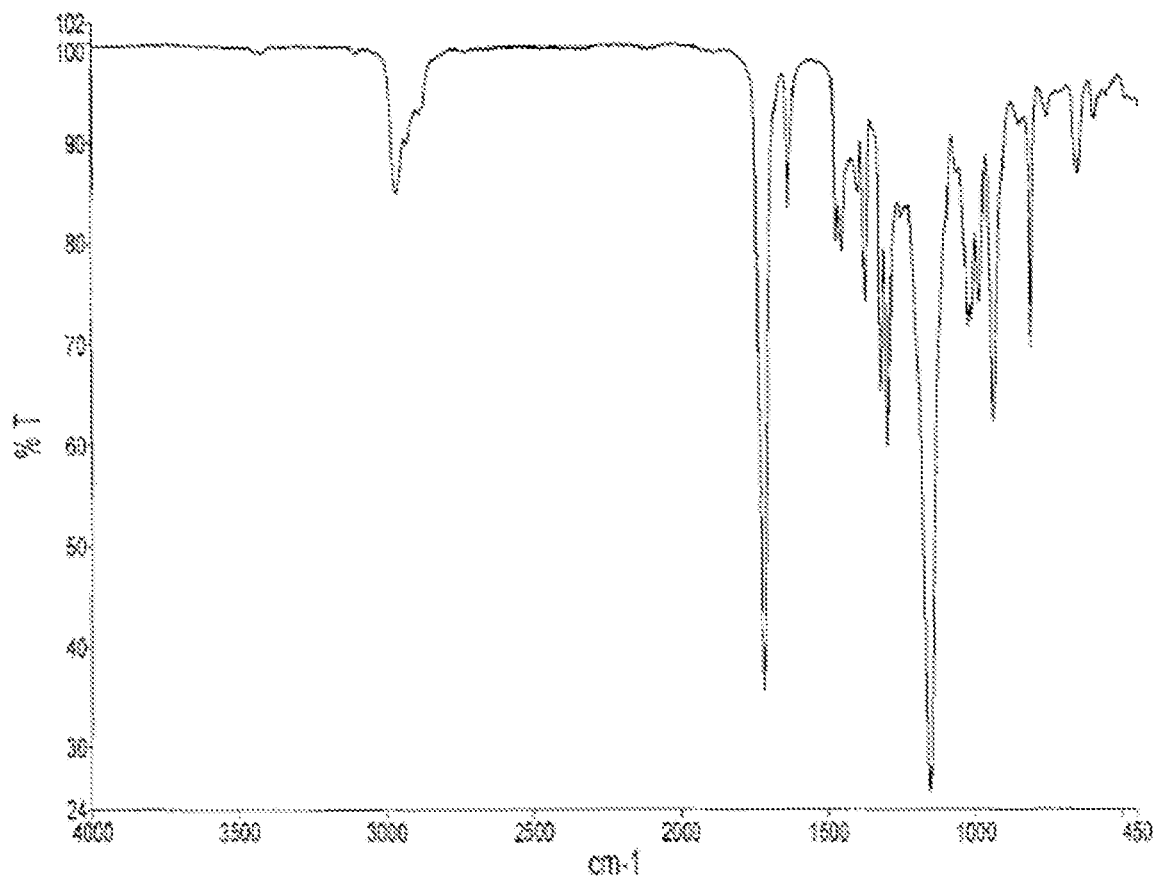
FIG. 21 shows IR spectrum of ene-thiol methacrylate (A-21) obtained in Example 21A.
Figure 22:
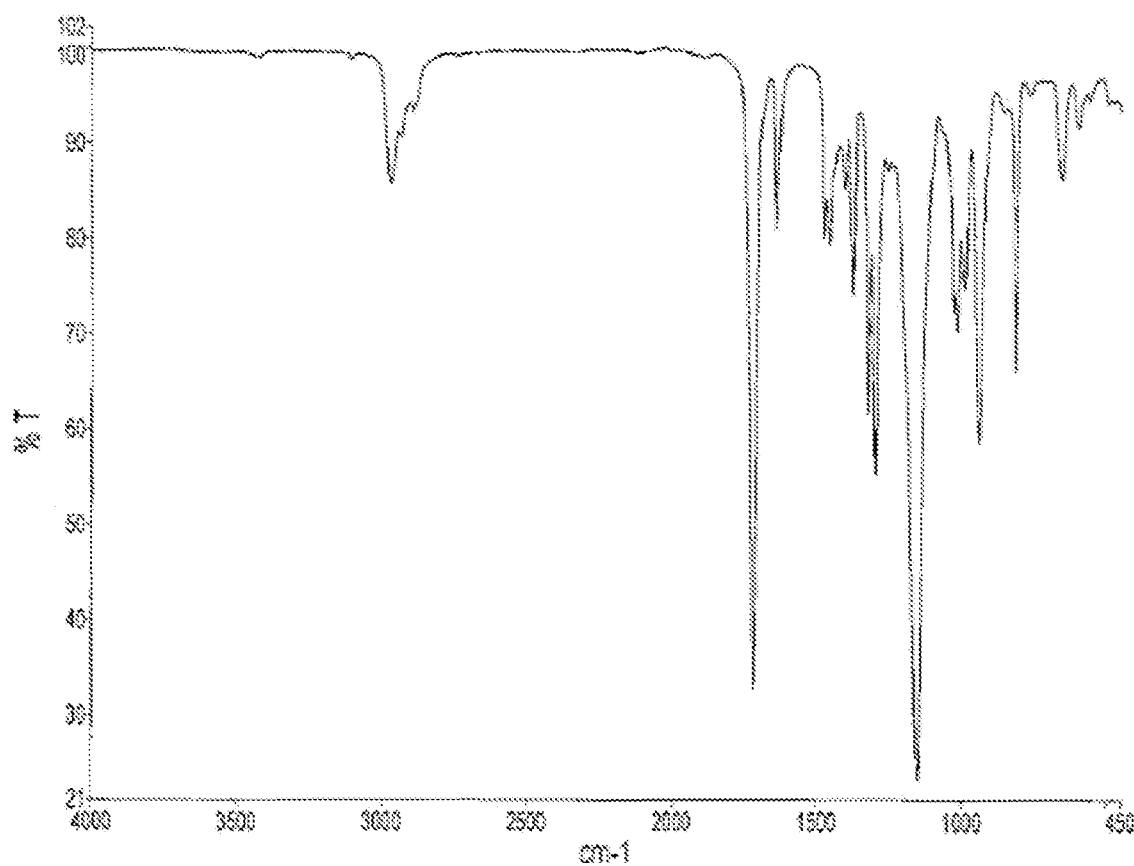
FIG. 22 shows IR spectrum of ene-thiol methacrylate (A-22) obtained in Example 22A.
Figure 23:
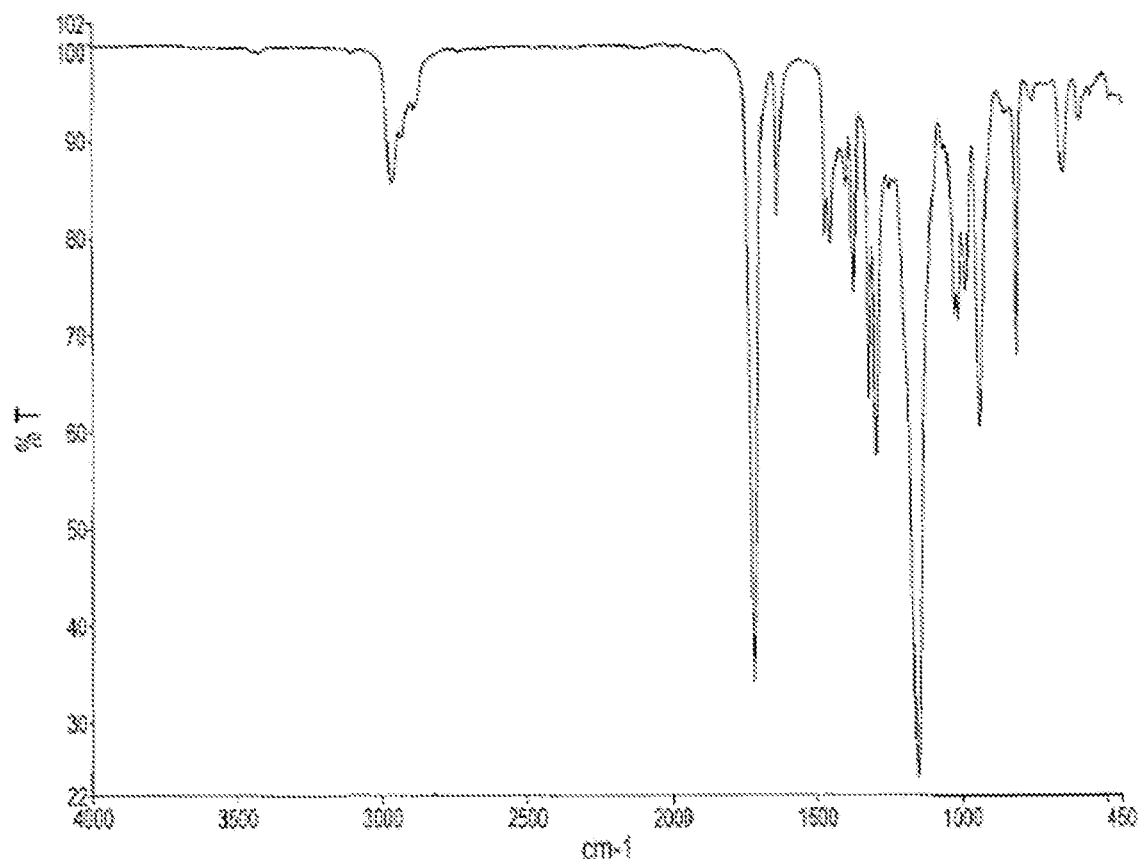
FIG. 23 shows IR spectrum of ene-thiol methacrylate (A-23) obtained in Example 23A.
Figure 24:
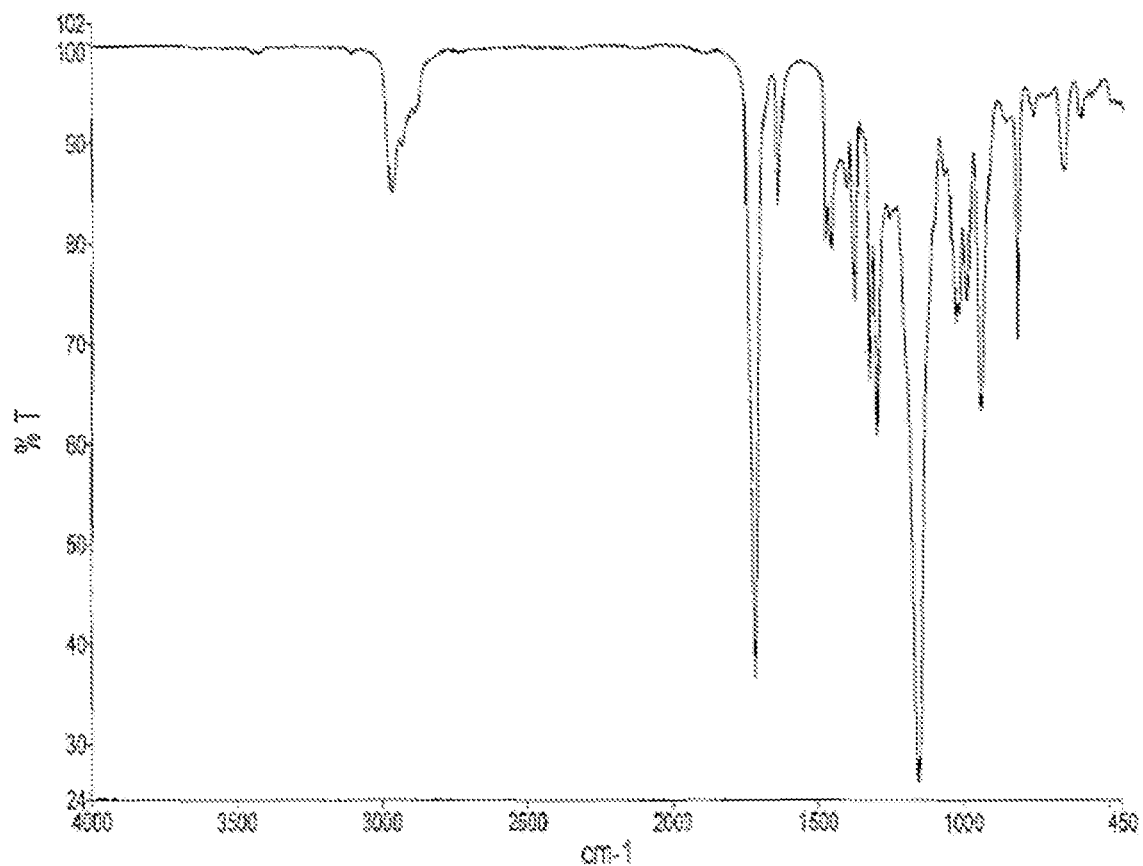
FIG. 24 shows IR spectrum of ene-thiol methacrylate (A-24) obtained in Example 24A.
Figure 25:
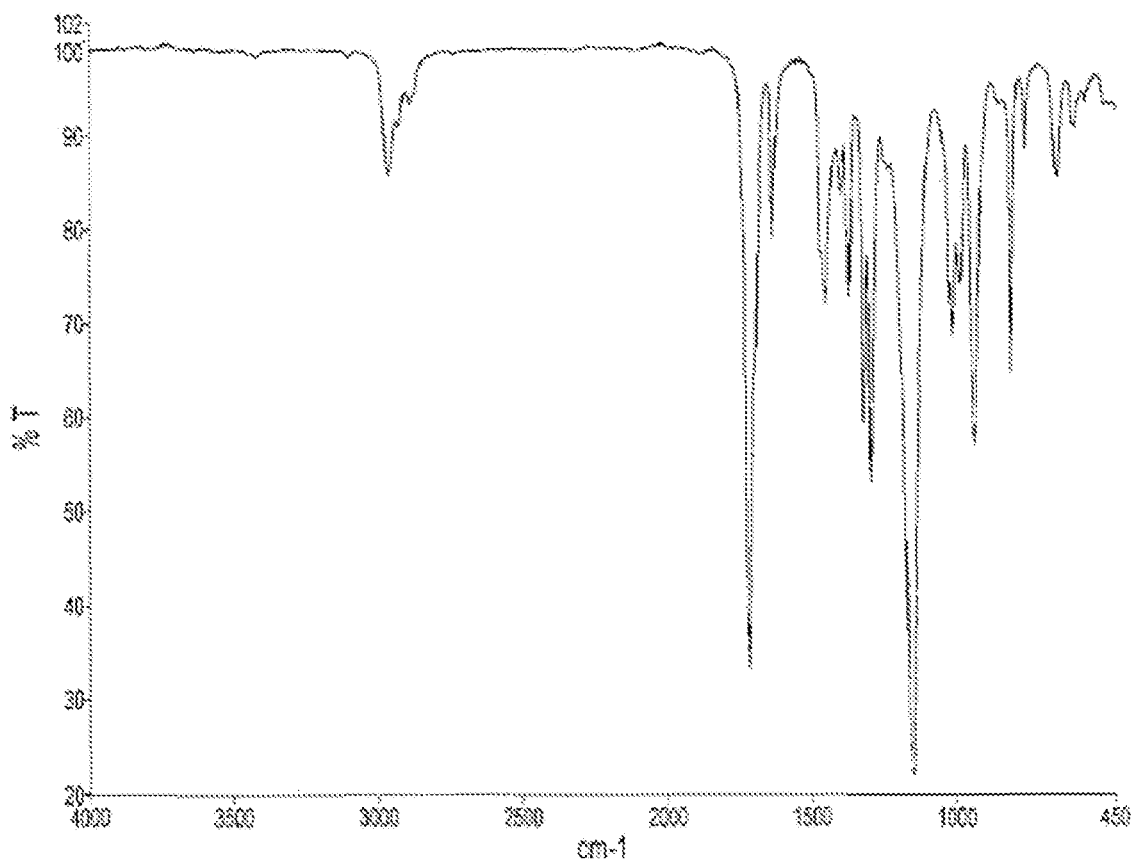
FIG. 25 shows IR spectrum of ene-thiol methacrylate (A-25) obtained in Example 25A.
Figure 26:
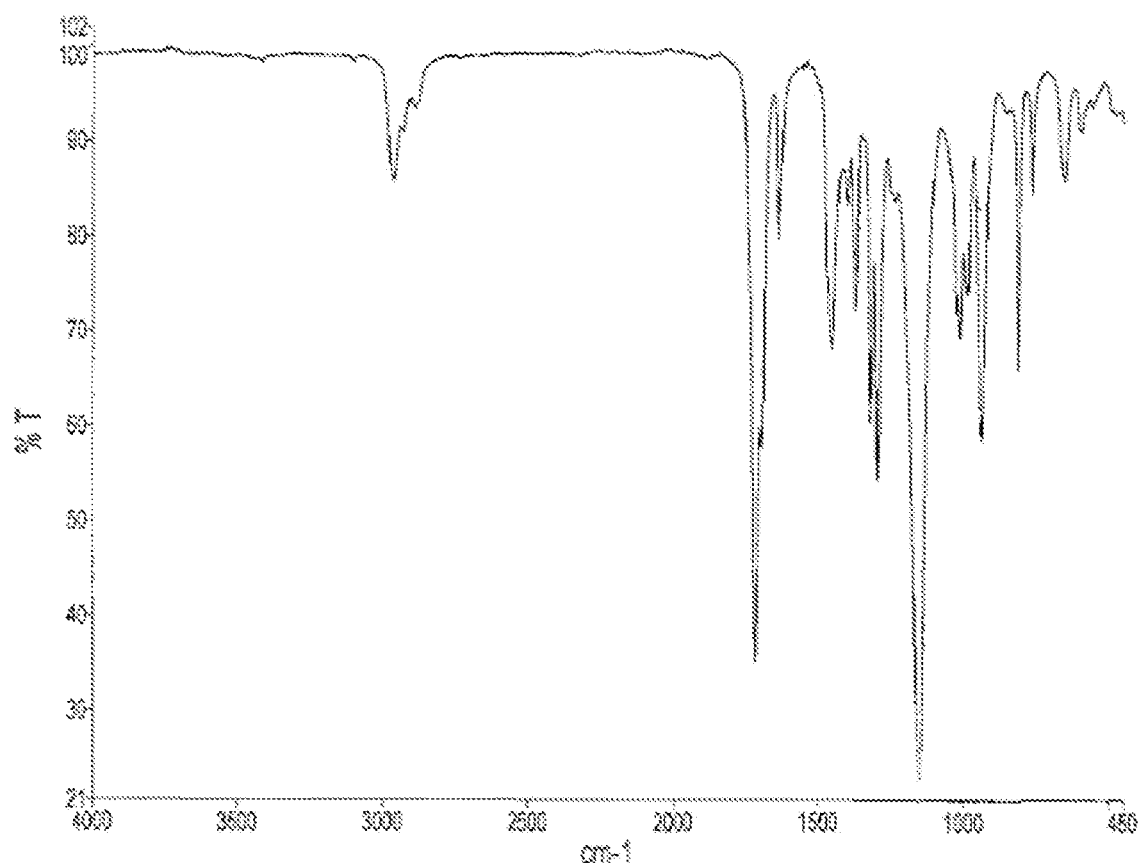
FIG. 26 shows IR spectrum of ene-thiol methacrylate (A-26) obtained in Example 26A.
Figure 27:
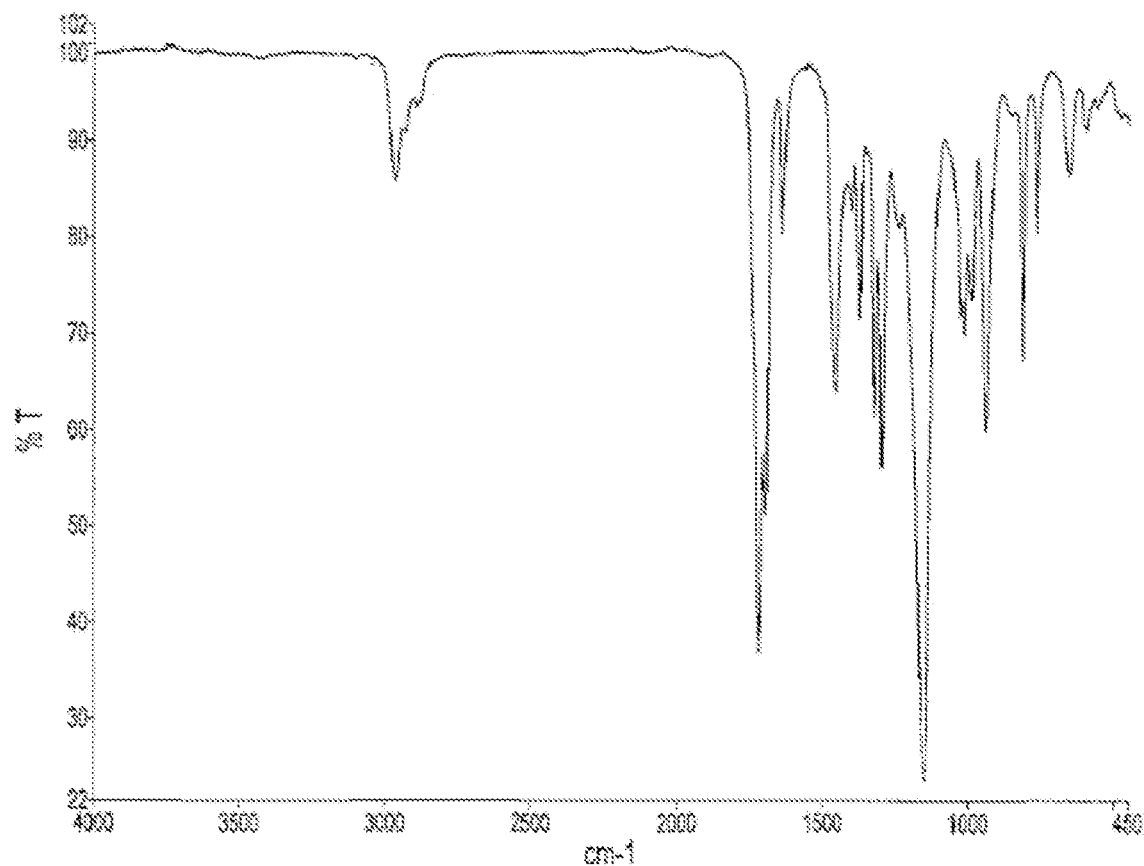
FIG. 27 shows IR spectrum of ene-thiol methacrylate (A-27) obtained in Example 27A.
Figure 28:
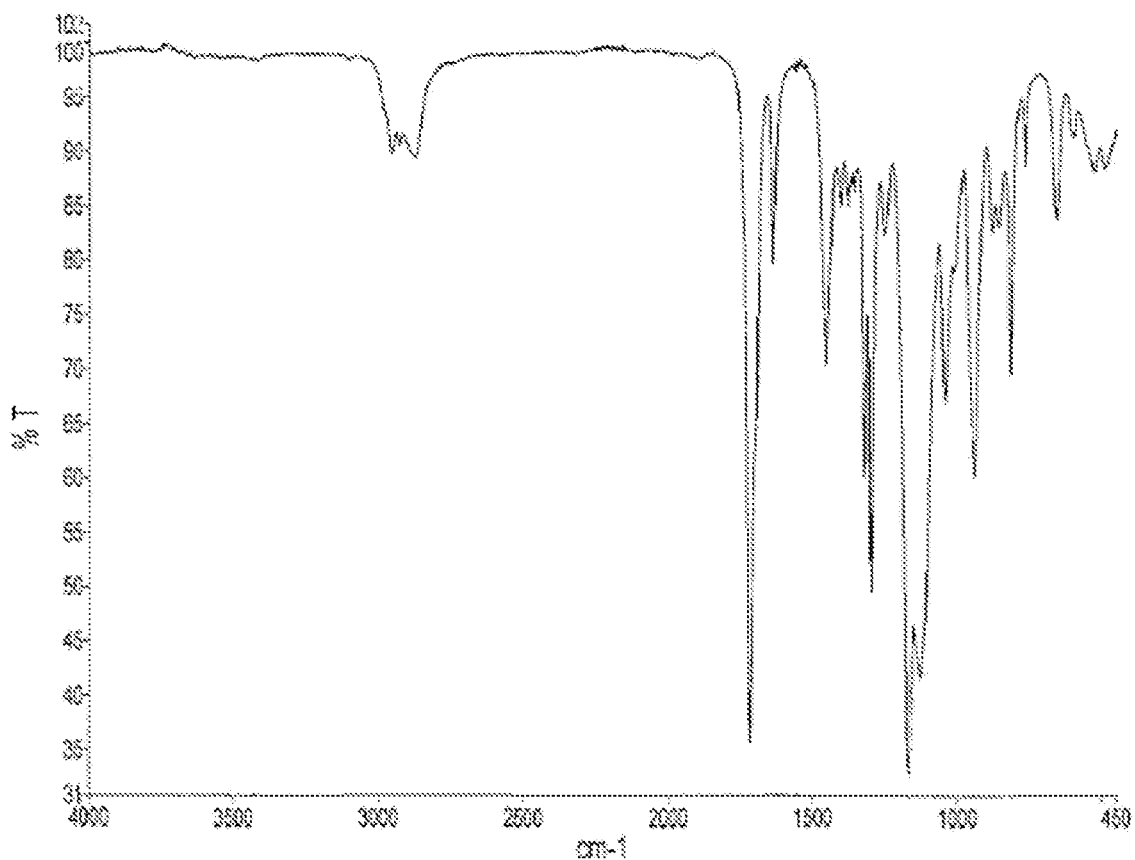
FIG. 28 shows IR spectrum of ene-thiol methacrylate (A-28) obtained in Example 28A.
Figure 29:
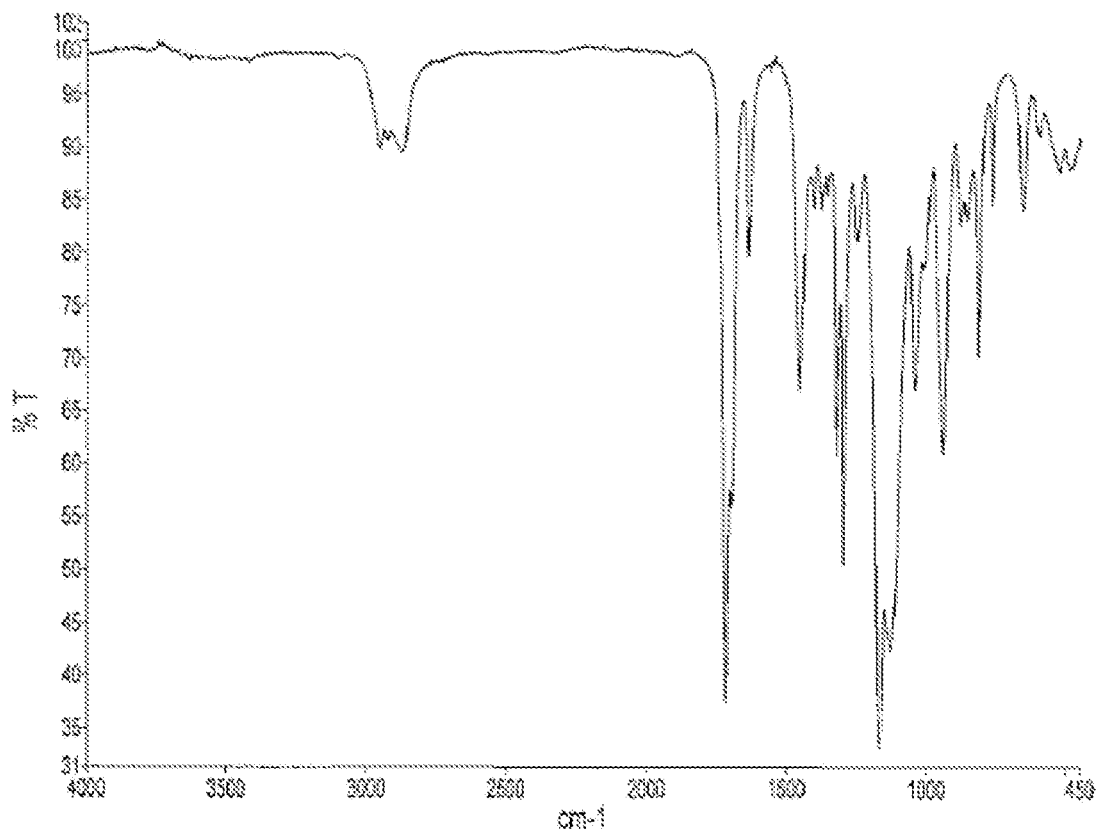
FIG. 29 shows IR spectrum of ene-thiol methacrylate (A-29) obtained in Example 29A.
Figure 30:
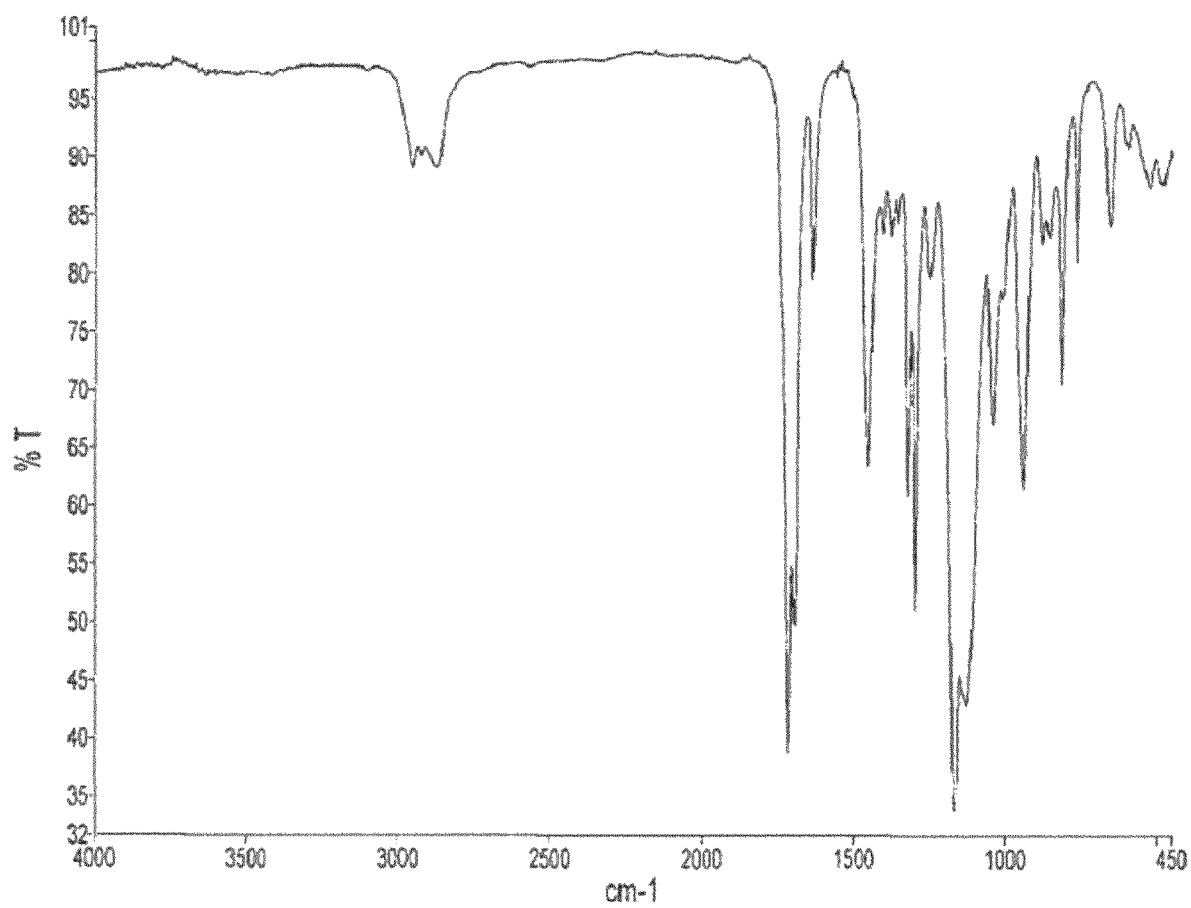
FIG. 30 shows IR spectrum of ene-thiol methacrylate (A-30) obtained in Example 30A.
Figure 31:
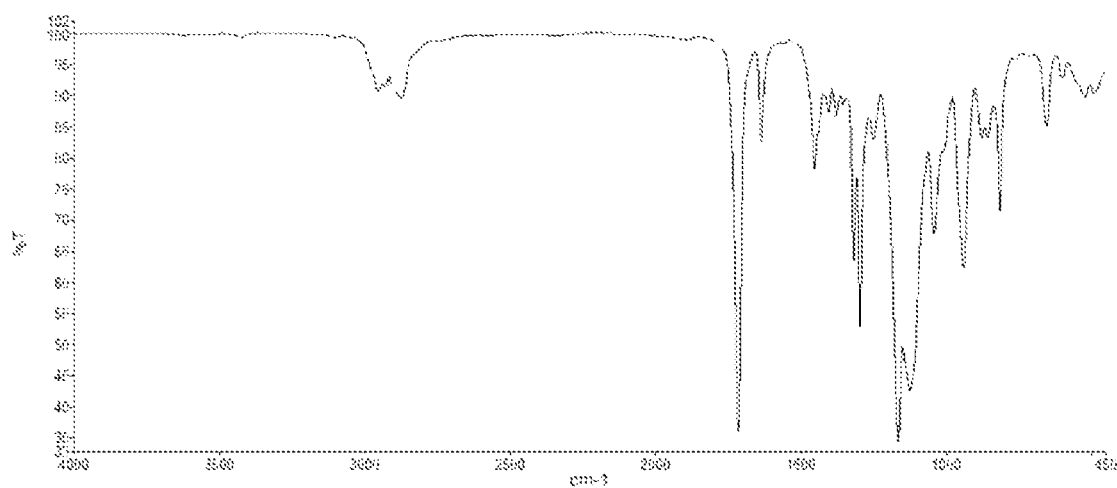
FIG. 31 shows IR spectrum of ene-thiol methacrylate (A-31) obtained in Example 31A.
Figure 32:
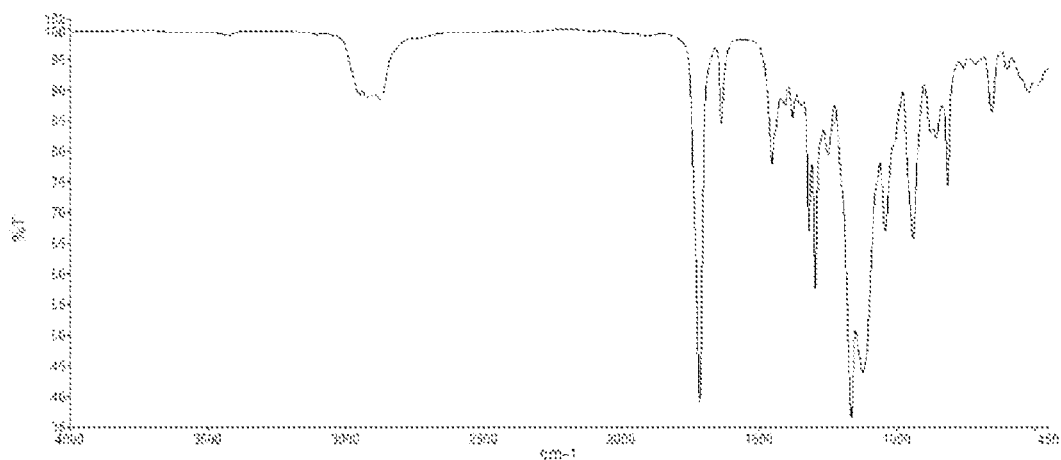
FIG. 32 shows IR spectrum of ene-thiol methacrylate (A-32) obtained in Example 32A.
Figure 33:
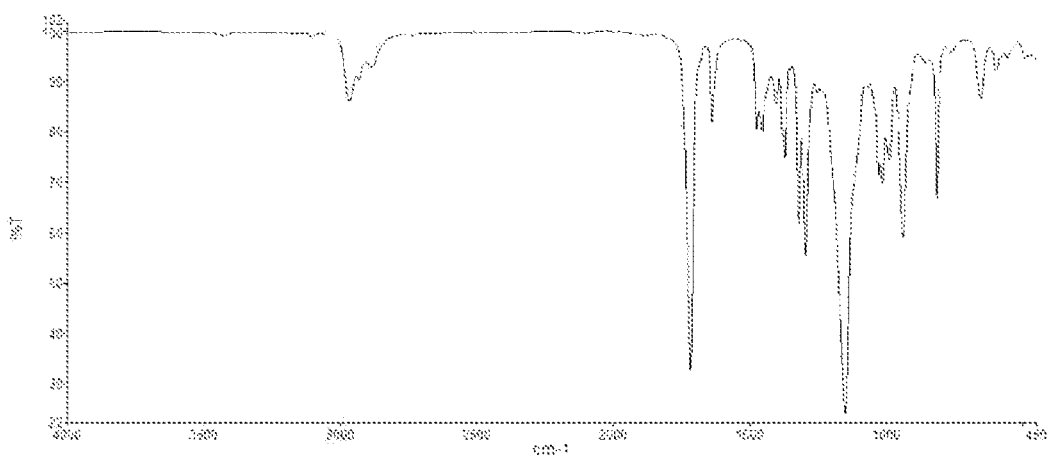
FIG. 33 shows IR spectrum of ene-thiol methacrylate (A-33) obtained in Example 33A.
Figure 34:
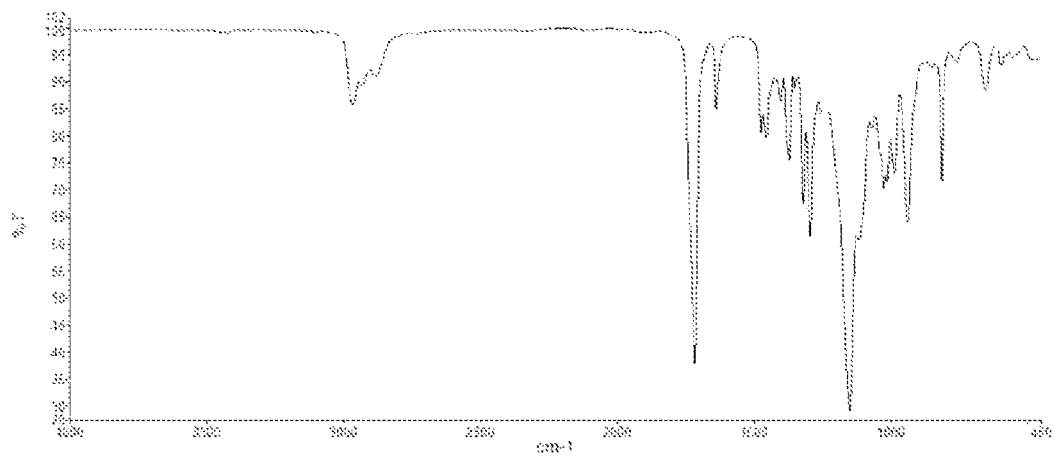
FIG. 34 shows IR spectrum of ene-thiol methacrylate (A-34) obtained in Example 34A.
Figure 35:
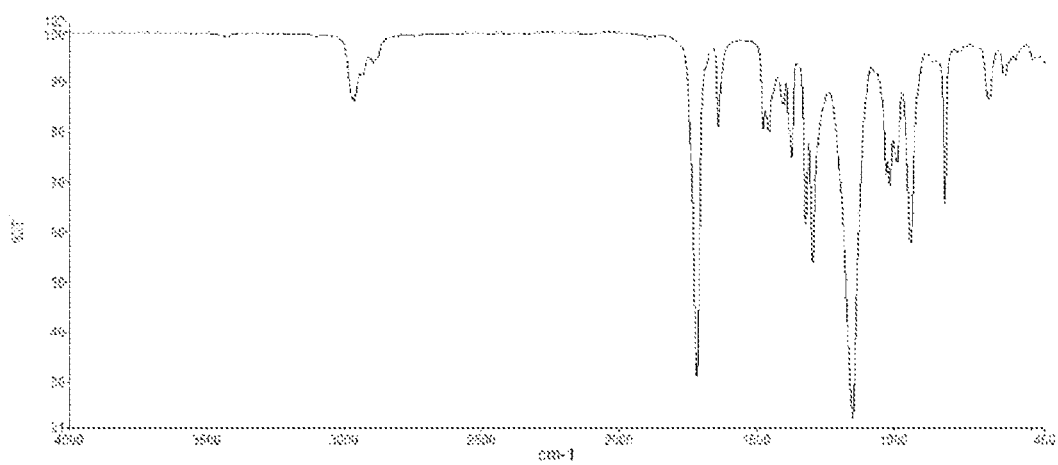
FIG. 35 shows IR spectrum of ene-thiol methacrylate (A-35) obtained in Example 35A.
Figure 36:
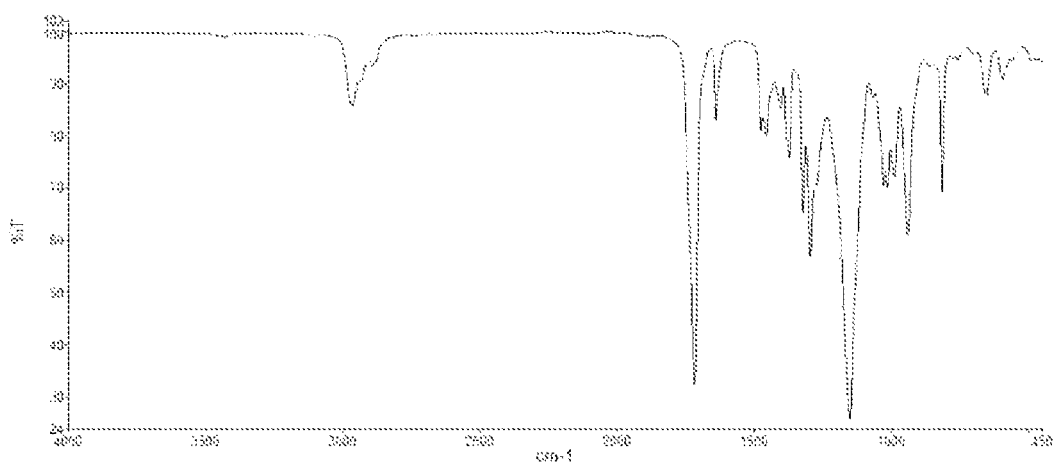
FIG. 36 shows IR spectrum of ene-thiol methacrylate (A-36) obtained in Example 36A.
Figure 37:
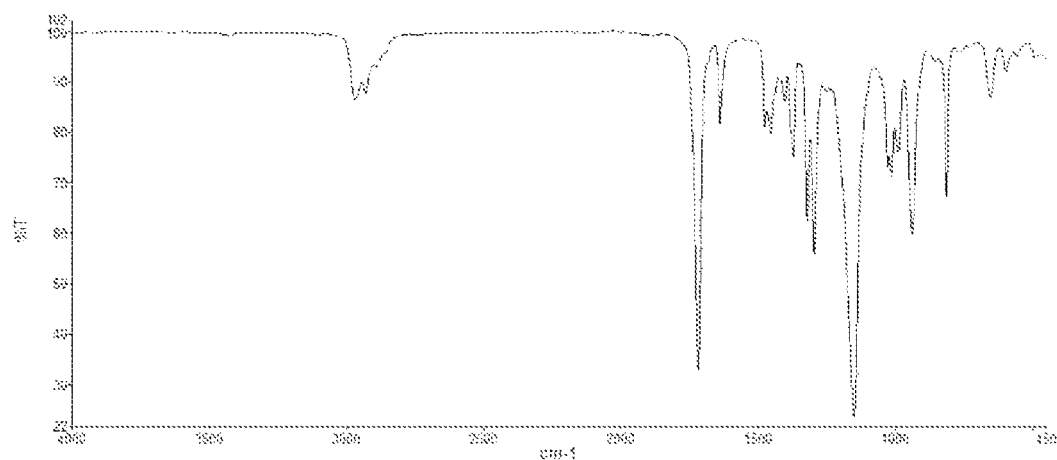
FIG. 37 shows IR spectrum of ene-thiol methacrylate (A-37) obtained in Example 37A.
Figure 38:
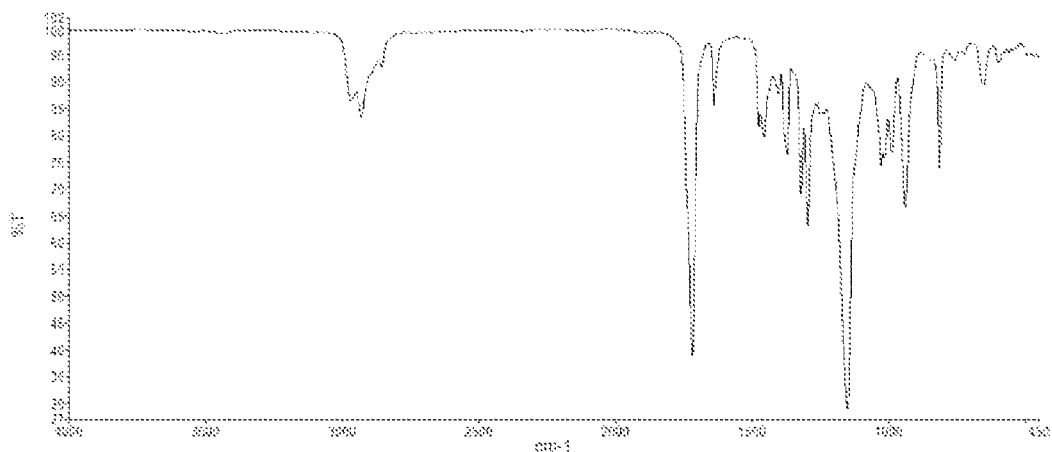
FIG. 38 shows IR spectrum of ene-thiol methacrylate (A-38) obtained in Example 38A.
Figure 39:
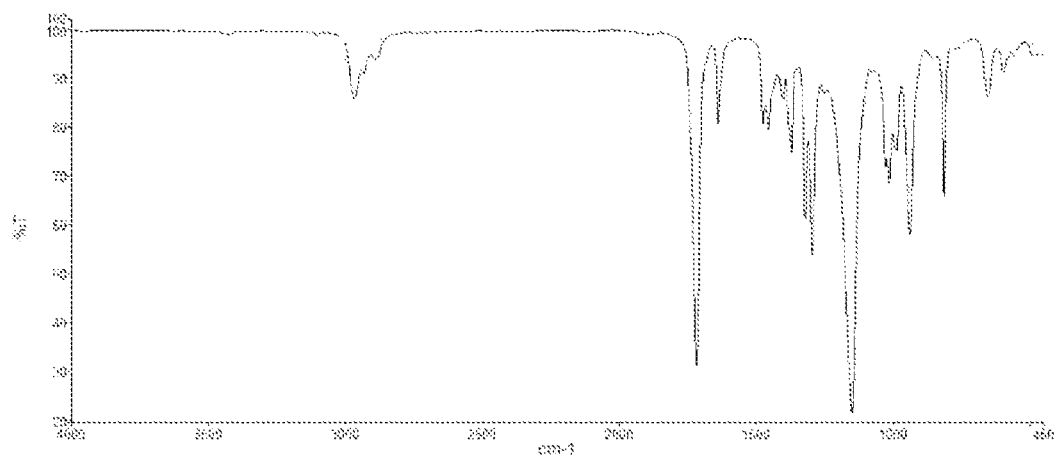
FIG. 39 shows IR spectrum of ene-thiol methacrylate (A-39) obtained in Example 39A.
Figure 40:
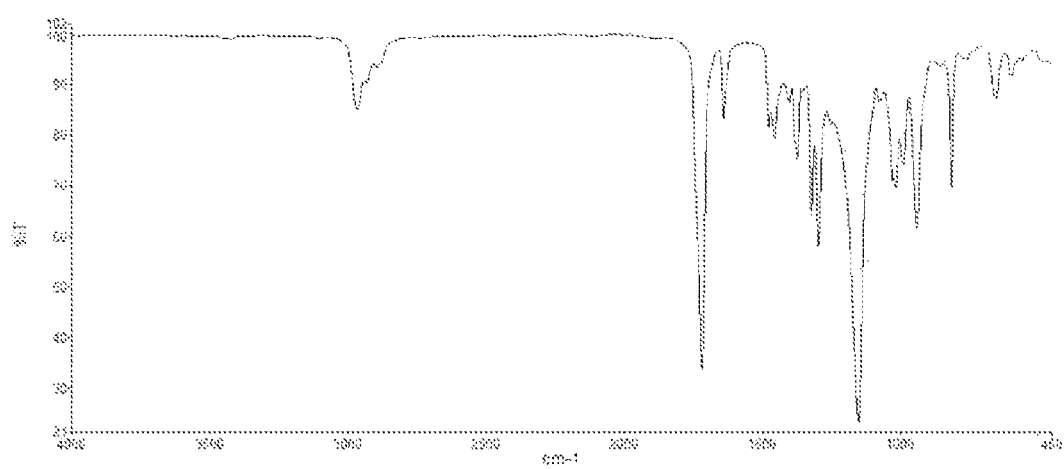
FIG. 40 shows IR spectrum of ene-thiol methacrylate (A-40) obtained in Example 40A.
Figure 41:
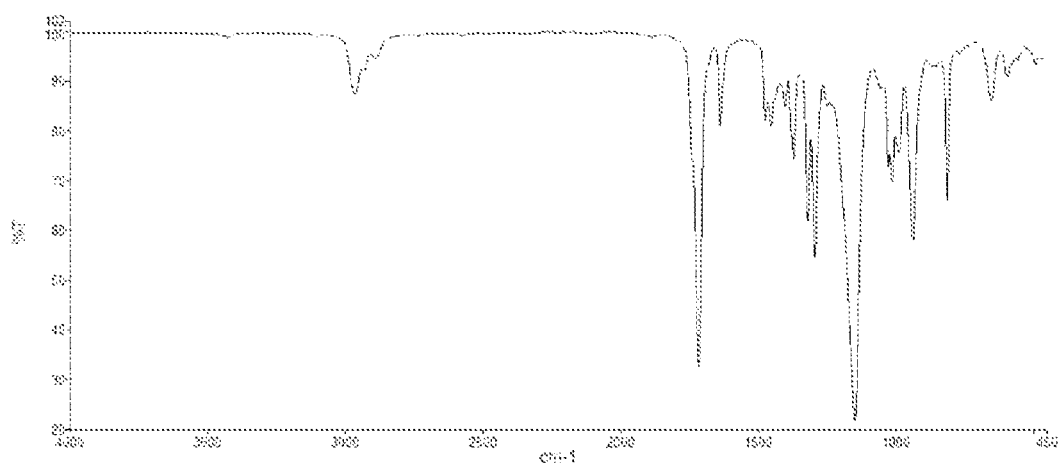
FIG. 41 shows IR spectrum of ene-thiol methacrylate (A-41) obtained in Example 41A.
Figure 42:
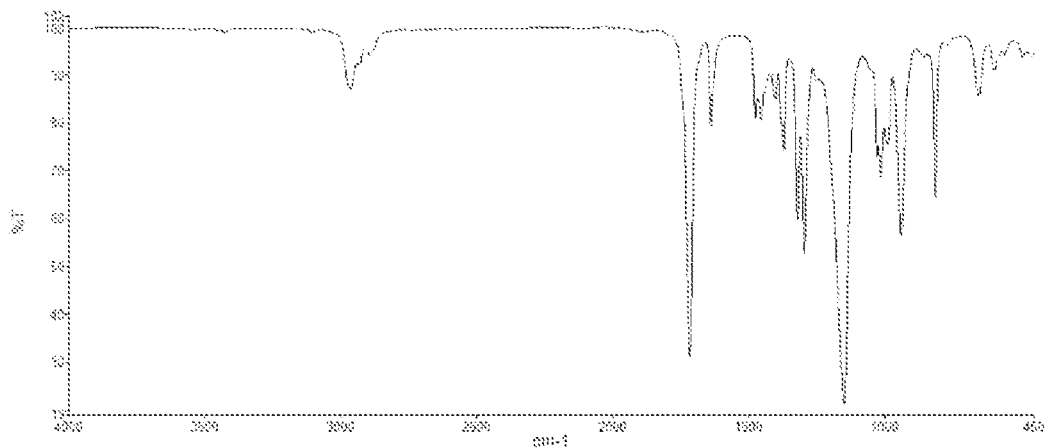
FIG. 42 shows IR spectrum of ene-thiol methacrylate (A-42) obtained in Example 42A.
Figure 43:
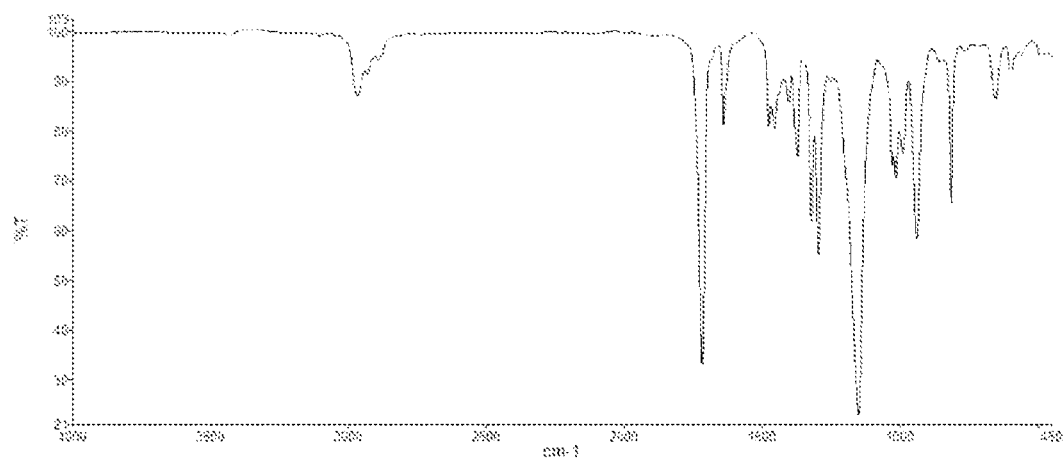
FIG. 43 shows IR spectrum of ene-thiol methacrylate (A-43) obtained in Example 43A.
Figure 44:
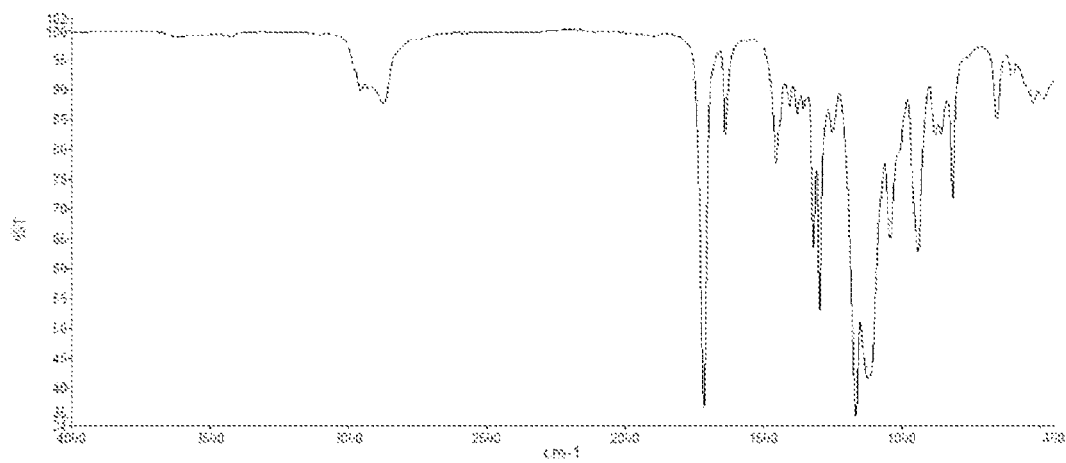
FIG. 44 shows IR spectrum of ene-thiol methacrylate (A-44) obtained in Example 44A.
Figure 45:
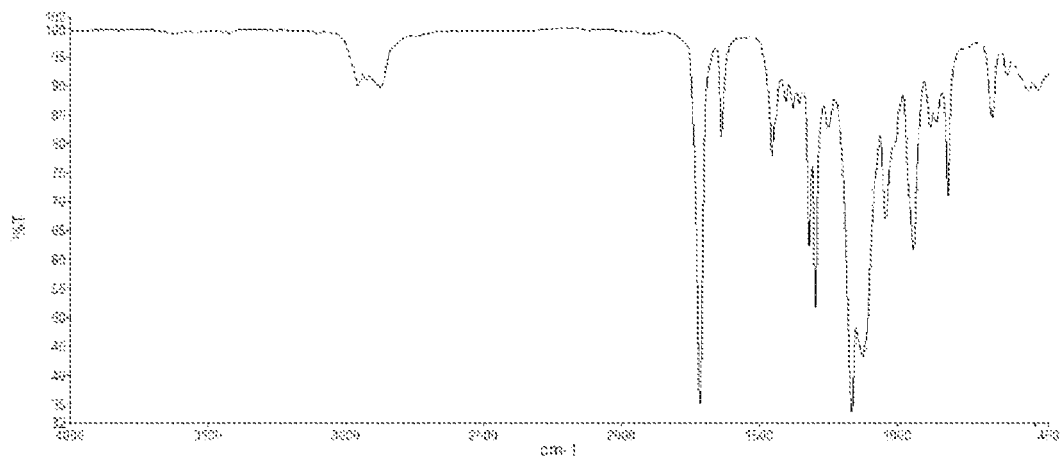
FIG. 45 shows IR spectrum of ene-thiol methacrylate (A-45) obtained in Example 45A.
Figure 46:
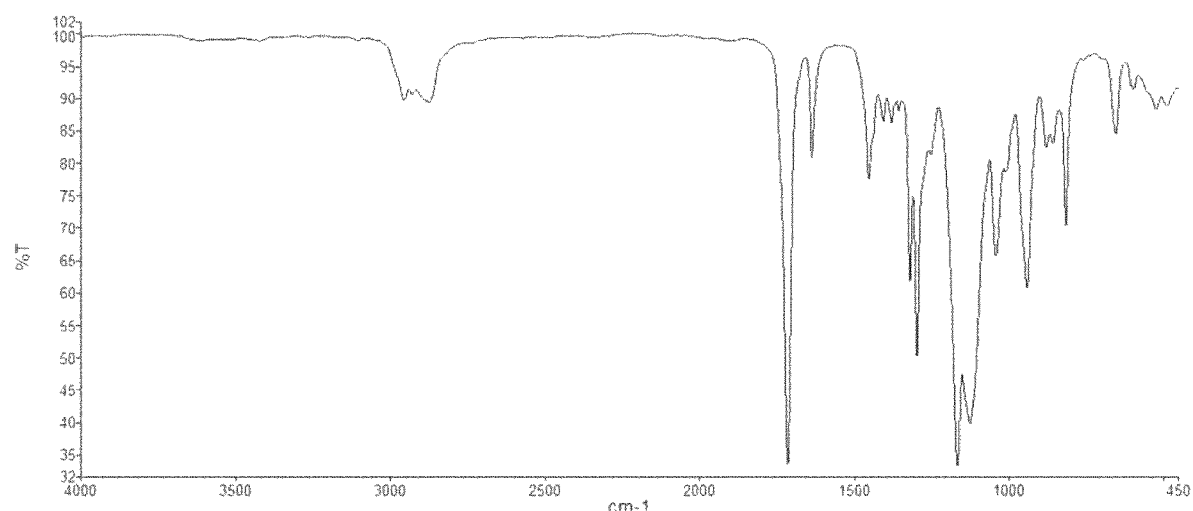
FIG. 46 shows IR spectrum of ene-thiol methacrylate (A-46) obtained in Example 46A.
Figure 47:
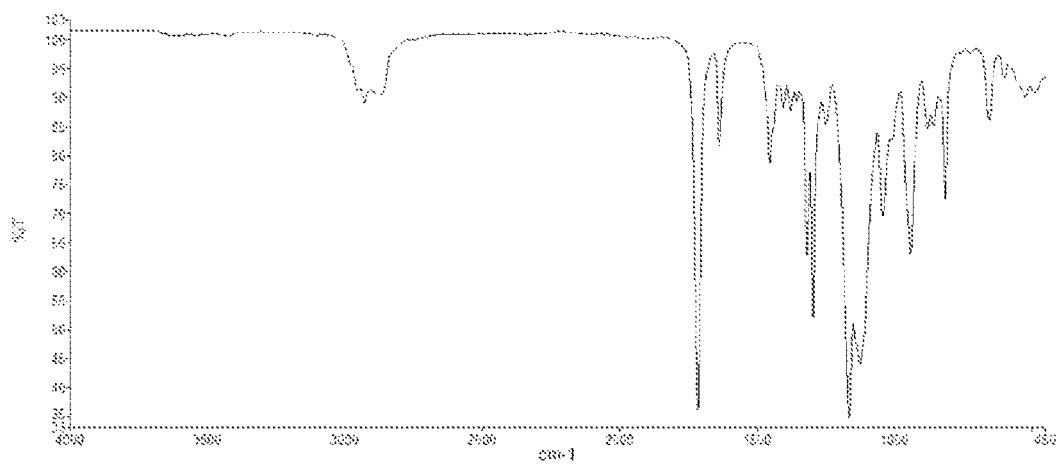
FIG. 47 shows IR spectrum of ene-thiol methacrylate (A-47) obtained in Example 47A.
Figure 48:
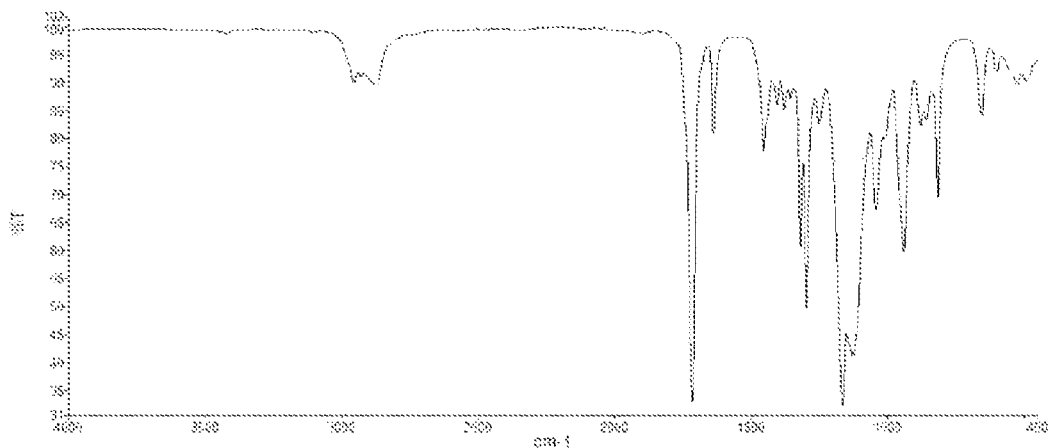
FIG. 48 shows IR spectrum of ene-thiol methacrylate (A-48) obtained in Example 48A.

Embodiments of the invention are described below in detail. It is noted here, however, that the invention is not limited to the below-described embodiments. In the below-described embodiments, the constituents thereof are not indispensable unless otherwise specified. The same applies to the numerical values and ranges thereof, without restricting the invention.

In the present disclosure, those numerical ranges that are stated with "to" each denote a range that includes the numerical values stated before and after "to" as the lower and upper limit values, respectively.

In a set of numerical ranges that are stated stepwise in the disclosure, the upper limit value or the lower limit value of a numerical range may be replaced with an upper limit value or a lower limit value of other numerical range. Further, in a numerical range stated in the disclosure, the upper limit or the lower limit of the numerical range may be replaced with a relevant value indicated in any of Examples.

In the present disclosure, "(meth)acryloyl" means acryloyl or methacryloyl, and "(meth)acrylate" means acrylate or methacrylate.

In the present disclosure, "iso(thio)cyanate" means isocyanate or isothiocyanate.

[(Meth)acrylate]

A (meth)acrylate in the present disclosure includes a reaction product of a thiol compound (1) containing two or more thiol groups, and a (meth)acrylate compound (2) containing two or more (meth)acryloyloxy groups. By using this (meth)acrylate, a cured product having an excellent mechanical property can be produced.

By the way, when a main component monomer capable of improving the mechanical property of the cured product is selected, the viscosity of the monomer composition may increase and handleability may decrease.

Therefore, from the point of improving handleability by decreasing the viscosity of the monomer composition, a diluting monomer may be added to a main component monomer. Examples of conventionally known diluting monomers include a (meth)acrylate such as triethylene glycol dimethacrylate.

However, when the conventionally known diluting monomer described above is added to the main component monomer to prepare the monomer composition, a function such as toughness in the cured product may decrease. On the other hand, the (meth)acrylate in the present disclosure described above is used as the diluting monomer which improves handleability of the monomer composition, There is a tendency that the mechanical property of the cured product can be improved as compared with the case where the conventionally known diluting monomer described above is used. Therefore, for example, the (meth)acrylate in the present disclosure described above may be used in combination with a main component monomer which can be polymerized in the monomer composition.

Modified Example of (Meth)Acrylate

A modified example of a (meth)acrylate in the present disclosure contains a structure represented by the following general formula (B) and two or more (meth)acryloyloxy groups. By using this (meth)acrylate, a cured product having an excellent mechanical property can be produced.

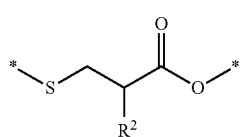

(B)

In the general formula (B), $R^2$ represents a hydrogen atom or a methyl group. Each * represents a binding site.

The (meth)acrylate in the present disclosure and the modified example thereof shown above may have a preferred aspect in the (meth)acrylate (A) described later.

[Monomer Composition for Dental Material]

A monomer composition for a dental material (hereinafter, it is also referred to as "monomer composition") in the present disclosure contains a (meth)acrylate (A) which is a reaction product of a thiol compound (1) containing two or more thiol groups (mercapto groups), and a (meth)acrylate compound (2) containing two or more (meth)acryloyloxy groups. The (meth)acrylate (A) is typically a polymerizable monomer.

The reaction product contained in the monomer composition in the present disclosure contain a structure formed by reacting the thiol groups contained in the thiol compound (1) and the (meth)acryloyloxy groups contained in the (meth)acrylate compound (2). The reaction product may not contain a thiol group, and may contain a (meth)acryloyloxy group. The reaction product may contain a sulfide bond, may contain a sulfide bond and an ester bond, and may contain a structure represented by the following general formula (B). A thiol group, a sulfide bond, and an ester bond in the reaction product can be confirmed by, for example, FT-IR (Fourier Transform Infrared Spectroscopy) measurement.

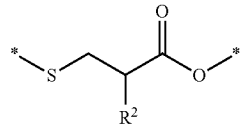

(B)

In the general formula (B), $R^2$ represents a hydrogen atom or a methyl group. Each * represents a binding site. For example, a residue of the thiol compound (1) from which one or more thiol groups have been removed, or a reside of the (meth)acrylate compound (2) from which one (meth)acryloyloxy group has been removed, may be bonded in the binding site. A residue of the thiol compound (1) from which one or more thiol groups have been removed, may be bonded in the binding site adjacent to the sulfur atom in the general formula (B). A reside of the (meth)acrylate compound (2) from which one (meth)acryloyloxy groups has been removed, may be bonded in the binding site adjacent to the oxygen atom in the general formula (B).

The reaction product may or may not contain a thiol group. For example, in the reaction of the thiol group contained in the thiol compound (1) and the (meth)acryloyloxy group contained in the (meth)acrylate compound (2), all the thiol groups contained in the thiol compound (1) may react, or some thiol groups may remain unreacted in the reaction product. The presence or absence of the thiol group may be confirmed by, for example, FT-IR measurement.

The reaction product may contain the thiol group, and may further contain the (meth)acryloyloxy group. For example, in the reaction of the thiol group contained in the thiol compound (1) and the (meth)acryloyloxy group contained in the (meth)acrylate compound (2), all the thiol groups contained in the thiol compound (1) may have reacted, and some (meth) acryloyloxy groups contained in the (meth)acrylate compound (2) may remain unreacted in the reaction product. The presence or absence of the (meth) acryloyloxy group may be confirmed by, for example, FT-IR measurement.

Examples of the thiol compound (1) include aliphatic polythiol compounds, aromatic polythiol compounds, and heterocyclic polythiol compounds.

The thiol compound (1) is not particularly limited, and examples thereof include aliphatic polythiol compounds such as 1,3-propanedithiol, 1,4-butanedithiol, 1,6-hexanedithiol, 2,5-hexanedithiol, 1,8-octanedithiol, 1,9-nonanedithiol, 3,6-dioxa-1,8-octanedithiol, 3,7-dithia-1,9-nonanedithiol, 1,4-butanediol bis(thioglycolate), bis(3-mercaptopropionic acid)ethylene glycol, 1,4-bis(3-mercaptobutyryloxy)butane, 1,2,3-propanetrithiol, tetrakis(mercaptomethyl)methane, trimethylolpropane tris(2-mercaptoacetate), trimethylolpropane tris(3-mercaptopropionate), trimethylolethane tris(2-mercaptoacetate), trimethylolethane tris(3-mercaptopropionate), pentaerythritol tetrakis(2-mercaptoacetate), pentaerythritol tetrakis(3-mercaptopropionate), dipentaerythritol hexakis(3-mercaptopropionate), 1,2,3-tris (mercaptomethylthio)propane, 1,2,3-tris(2-mercaptoethylthio)propane, 1,2,3-tris (3-mercaptopropylthio)propane, 4-mercaptomethyl-1,8-dimercapto-3,6-dithiaoctane, 5,7-dimercaptomethyl-1,11-dimercapto-3,6,9-trithiaundecane, 4,7-dimercapto methyl-1,11-dimercapto-3,6,9-trithiaundecane, 4,8-dimercaptomethyl-1,11-dimercapto-3,6,9-trithiaundecane, tetrakis(mercaptomethylthiomethyl)methane, tetrakis(2-mercaptoethylthiomethyl)methane, tetrakis(3-mercaptopropylthiomethyl)methane, bis(2,3-dimercaptopropyl)sulfide, and an ester of these thioglycolic acid or mercaptopropionic acid; aliphatic polythiol compounds such as 1,1,3,3-tetrakis(mercaptomethylthio)propane, 1,1,2,2-tetrakis(mercaptomethylthio)ethane, tris(mercaptomethylthio)methane, and tris(mercaptoethylthio)methane; aromatic polythiol compounds such as 1,3,5-trimercaptobenzene, 1,3,5-tris(mercaptomethyl)benzene, 1,3,5-tris(mercaptomethyleneoxy)benzene, and 1,3,5-tris(mercaptoethyleneoxy)benzene; and heterocyclic polythiol compounds such as 2,4,6-trimercapto-s-triazine, 2,4,6-trimercapto-1,3,5-triazine, and tris-[(3-mercaptopropionyloxy)-ethyl]-isocyanurate.

From the point of producing the (meth)acrylate (A) capable of producing a cured product having an excellent mechanical property, the thiol compound (1) is preferably 1,4-butandithiol, 1,8-octanedithiol, 3,6-dioxa-1,8-octanedithiol, 3,7-dithia-1,9-nonanedithiol, 1,4-butanediol bis(thioglycolate), bis(3-mercaptopropionic acid)ethylene glycol, 1,4-bis(3-mercaptobutyryloxy)butane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, 4-mercaptomethyl-1,8-dimercapto-3,6-dithiaoctane, 1,1,3,3-tetrakis(mercaptomethylthio)propane, trimethylrol propane tris(3-mercaptopropionate), pentaerythritol tetrakis(2-mercaptoacetate), pentaerythritol tetrakis(3-mercaptopropionate) or tris-[(3-mercaptopropionyloxy)-ethyl]-isocyanurate.

The (meth)acrylate compound (2) is not particularly limited, and examples thereof include neopentyl di(meth)acrylate, 1,4-butanediol di(meth)acrylate, 1,6-hexanediol di(meth)acrylate, 1,8-octanediol di(meth)acrylate, 1,9-nonanediol di(meth)acrylate, 1,10-decanediol di(meth)acrylate, tricyclodecanedimethanol di(meth)acrylate, ethylene glycol di(meth)acrylate, diethylene glycol di(meth)acrylate, triethylene glycol di(meth)acrylate, tetraethylene glycol di(meth)acrylate, polyethylene glycol di(meth)acrylate, tripropylene glycol di(meth)acrylate, tetrapropylene glycol di(meth)acrylate, polypropylene glycol di(meth)acrylate, 2,2-bis[4-(3-(meth)acryloyloxy-2-hydroxypropoxy)phenyl]propane, ethylene oxide-modified bisphenol A di(meth)acrylate, and propylene oxide-modified bisphenol A di(meth)acrylate.

From the point of handleability in mixing with a main component monomer, a viscosity at 25° C. of the (meth)acrylate in the present disclosure may be from 1 mPa·s to 10,000 mpPas, may be from 10 mPa s to 7,000 mPa s, may be 50 mPa s to 5,000 mPa s, or may be from 100 mPa s to 3,000 mPa·s. The viscosity in the present disclosure is a value measured by E-type viscometer (TVE-22H manufactured by Toki Sangyo Co., Ltd).

In a mixture of the (meth)acrylate (A) and an unreacted product which is at least one of the thiol compound (1) and the (meth)acrylate compound (2) used in the production of the (meth)acrylate (A), a viscosity at 25° C. may be from 1 mPa s to 10,000 mPa s, may be from 10 mPa s to 7,000 mPa s, may be 50 mPa s to 5,000 mPa s, or may be from 100 mPa s to 3,000 mPa·s. The viscosity in the present disclosure is a value measured by E-type viscometer (TVE-22H manufactured by Toki Sangyo Co., Ltd).

In the reaction product, as described above, all the thiol groups contained in the thiol compound (1) may have reacted, and some (meth)acryloyloxy groups contained in the (meth)acrylate compound (2) remain unreacted. For example, the reaction product may be a (meth)acrylate represented by the general formula (1).

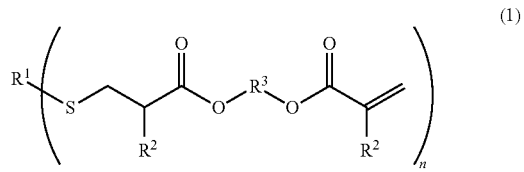

In the general formula (1), $R^1$ represents a residue of a bifunctional to tetrafunctional thiol compound from which all thiol groups have been removed; $R^2$ represents a hydrogen atom or a methyl group; $R^3$ represents a residue of a di(meth)acrylate from which two (meth)acryloyloxy groups have been removed. n is an integer from 2 to 4. Plural instances of $R^2$ and $R^3$ may be the same or different, respectively. The bifunctional to tetrafunctional thiol compound may be the thiol compound (1) as described above, or the di(meth)acrylate may be the (meth)acrylate compound (2) as described above.

In the general formula (1), $R^1$ is preferably a residue obtained by removing all thiol groups from a bifunctional to tetrafunctional thiol compound having 2 to 20 carbon atoms and containing at least one bond selected from a sulfide bond, an ester bond, an ether bond, and an alkylene group. The thiol compound as described above is preferably a compound having 2 to 20 carbon atoms and containing at least one bond selected from a sulfide bond, an ester bond, an ether bond, and an alkylene group, and more preferably a compound having 2 to 20 carbon atoms and containing one or more sulfide bonds, ester bonds, or ether bonds, further preferably a compound having 2 to 20 carbon atoms and containing two or more sulfide bonds, ester bonds, or ether bonds, or a compound having 2 to 20 carbon atoms and containing an alkylene group and not containing a sulfide bond, an ester bond, or an ether bond, and particularly preferably a compound having 2 to 20 carbon atoms and containing two or three sulfide bonds, a compound having 2 to 20 carbon atoms and containing three or four ester bonds, a compound having 2 to 20 carbon atoms and containing two ether bonds, or a compound having 2 to 20 carbon atoms and containing an alkylene group and not containing a sulfide bond, an ester bond, or an ether bond.

In the general formula (1), $R^1$ may represent a residue of a trifunctional or tetrafunctional thiol compound from which all thiol groups have been removed, or n may be 3 or 4.

In the general formula (1), a molecular weight of the $R^1$ is preferably from 100 to 500.

In the general formula (1), $R^1$ is preferably a group represented by the following formula (2), (3), (4), (5), (6-1), (6-2), (6-3), (7), (8), (9) or (10). * in each formula represents a binding site, and more specifically, represents a binding site with a sulfur atom shown in the general formula (1). In formula (8), $R^5$ represents a divalent hydrocarbon group having 1 to 10 carbon atoms. In formula (9), $R^6$, $R^7$, and $R^8$ each independently represent a divalent hydrocarbon group having 1 to 10 carbon atoms. In formula (10), $R^9$, $R^{10}$, and $R^{11}$ each independently represent a divalent hydrocarbon group having 1 to 10 carbon atoms; and $Y^1$ and $Y^2$ each independently represent an oxygen atom or a sulfur atom. Examples of the divalent hydrocarbon group having 1 to 10 carbon atoms include a divalent acyclic hydrocarbon group and a divalent cyclic hydrocarbon group described later.

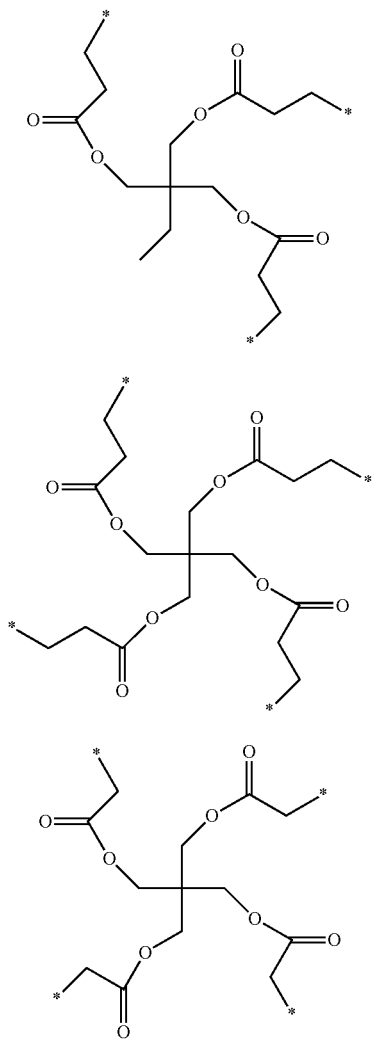

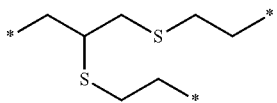

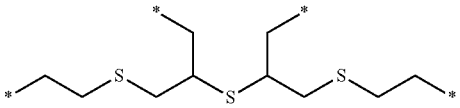

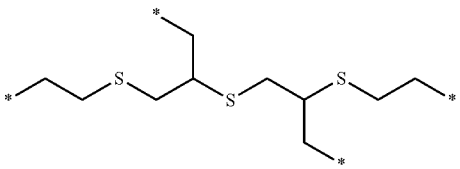

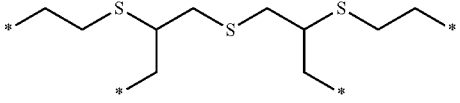

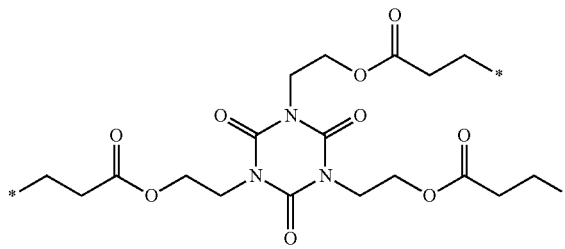

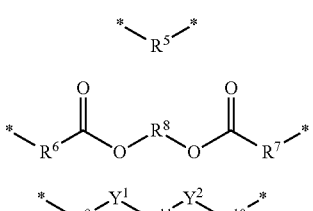

In the general formula (1), $R^2$ independently represents a hydrogen atom or a methyl group, and it is preferable that each of the plurality of $R^2$ is a hydrogen atom or a methyl group.

In the general formula (1), $R^3$ represents a residue of a di(meth)acrylate from which two (meth)acryloyloxy groups have been removed. Further, $R^3$ represents a residue obtained by removing two (meth)acryloyloxy groups from a di(meth)acrylate having 1 to 50 carbon atoms.

In the general formula (1), $R^3$ is preferably a linear or branched divalent acyclic hydrocarbon group having 1 to 50 carbon atoms, a divalent cyclic hydrocarbon group having 3 to 50 carbon atoms, or a divalent organic group having 1 to 50 carbon atoms, and containing an oxygen atom in a main chain. The divalent cyclic hydrocarbon group having 3 to 50 carbon atoms may be composed of only a cyclic hydrocarbon moiety, or may be a combination of a cyclic hydrocarbon moiety and an acyclic hydrocarbon moiety. In the present disclosure, examples of the divalent acyclic hydrocarbon group include an alkylene group, an alkenylene group and an alkynylene group, and examples of the divalent cyclic hydrocarbon group include a cycloalkylene group, a cycloalkenylene group and a cycloalkynylene group, and an arylene group. The divalent organic group containing an oxygen atom in a main chain does not preferbly a structure in which oxygen atoms are continuously present in the main chain, for example, "—O—O—", and it is preferable that a structure other than the oxygen atom is a hydrocarbon group. A hydrogen atom contained in the acyclic hydrocarbon group and the cyclic hydrocarbon group may be substituted with a substituent such as a halogen atom such as a chlorine atom or a bromine atom, an alkoxy group, a nitro group, a hydroxy group, or a carbonyl group, and a hydrogen atom contained in the cyclic hydrocarbon group may be substituted with a substituent such as a halogen atom such as a chlorine atom or a bromine atom, an alkoxy group, a nitro group, a hydroxy group, a carbonyl group, or an alkyl group.

The linear or branched divalent acyclic hydrocarbon group having 1 to 50 carbon atoms is preferably a linear or branched divalent acyclic hydrocarbon group having 1 to 20 carbon atoms, and more preferably a linear or branched divalent acyclic hydrocarbon group having 1 to 10 carbon atoms.

The divalent cyclic hydrocarbon group having 3 to 50 carbon atoms is preferably a divalent cyclic hydrocarbon group having 6 to 30 carbon atoms, and more preferably a divalent cyclic hydrocarbon group having 10 to 25 carbon atoms.

The divalent organic group having 1 to 50 carbon atoms, and containing an oxygen atom in a main chain is preferably an oxyalkylene group having 1 to 50 carbon atoms, and more preferably an oxyalkylene group having 2 to 30 carbon atoms.

In the general formula (1), $R^3$ may be independently one substituent selected from the residue of the (meth)acrylate (2), exemplified above, from which two (meth)acryloyloxy groups have been removed, and it is preferable that each of the plurality of $R^3$ is one substituent selected from the residue of the (meth)acrylate (2), exemplified above, from which two (meth)acryloyloxy groups have been removed.

(Method 1 of Manufacturing (Meth)Acrylate (A))

Hereinafter, the method 1 of manufacturing the (meth) acrylate (A) in the present disclosure will be described. The method 1 of manufacturing the (meth)acrylate (A) in the present disclosure includes a reaction of the thiol compound (1) and the (meth)acrylate compound (2). Examples of the thiol compound (1) and the (meth)acrylate compound (2) used in the manufacturing method 1 include the above described compounds.

When the thiol compound (1) and the (meth)acrylate compound (2) are reacted, from the point of efficiently producing the (meth)acrylate (A), a ratio (b/a) of a mass b in the (meth)acrylate compound (2) with respect to a mass a in the thiol compound (1) is preferably in a range of from 0.5 to 35, more preferably in a range of from 2 to 15, and further preferably in a range of from 3 to 10.

From the point of efficiently producing the (meth)acrylate (A), a ratio (the number of moles of acryloyloxy group/the number of moles of thiol group) of the number of moles of the acryloyloxy group contained in the (meth)acrylate compound (2) with respect to the number of moles of the thiol group contained in the thiol compound (1) is preferably from 0.5 to 20, more preferably from 1 to 15, and further preferably from 1.5 to 10.

When the thiol compound (1) and the (meth)acrylate compound (2) are reacted, from the point of improving the reaction rate, a catalyst may be added. As the catalyst, a known catalyst that accelerates the reaction of the thiol group contained in the thiol compound (1) and the (meth) acryloyloxy group contained in the (meth)acrylate compound (2), that is, the enethiol reaction can be used.

A phosphine compound is preferably used as the catalyst. Examples of the phosphine compound include trialkylphosphine compounds such as trimethylphosphine, triethylphosphine, triisopropylphosphine, tri-n-propylphosphine, tri-tert-butylphosphine, triisobutylphosphine, tri-n-butylphosphine, tri-n-hexylphosphine, tri-n-octylphosphine, and tricyclohexylphosphine; methyldiphenylphosphine, dimethylphenylphosphine, tri-o-tolylphosphine, tri-m-tolylphosphine, tri-p-tolylphosphine, diethylphenylphosphine, dichloro(ethyl)phosphine, dichloro(phenyl)phosphine, and chlorodiphenylphosphine. These may be used singly or in combination of two or more. Among these catalysts, from the point of suppressing the gelation and proceeding with the reaction preferably, a trialkylphosphine compound is preferable.

As the trialkylphosphine compound, trialkylphosphine compounds such as tri-n-butylphosphine, tri-n-hexylphosphine, tricyclohexylphosphine, and tri-n-octylphosphine are preferable. The trialkylphosphine compound may be used singly or in combination of two or more.

From the point of reaction regulation and catalytic effect, the amount of the catalyst used is preferably from 0.001% by mass to 0.5% by mass, more preferably from 0.002% by mass to 0.3% by mass, further preferably from 0.01% by mass to 0.3% by mass, particularly preferably from 0.01% by mass to 0.2% by mass, and even more preferably from 0.05% by mass to 0.2% by mass, with respect to 100% by mass of the total of the thiol compound (1) and the (meth) acrylate compound (2). The entire amount of the catalyst may be added at the start of the reaction, or the catalyst may be added to the reaction system sequentially or divided as needed.

The reaction temperature is not particularly limited, and, from the point of shortening the reaction time and suppressing the generation of by-products, is preferably from 0° C. to 100° C., more preferably from 20° C. to 80° C., further preferably from 30° C. to 60° C., and particularly preferably from 35° C. to 50° C.

The reaction time is not particularly limited, and, from the point of suppressing the generation of by-products, is preferably from 1 hour to 10 hours, more preferably from 1.5 hours to 6 hours, and further preferably from 2 hours to 5 hours.

When the thiol compound (1) and the (meth)acrylate compound (2) are reacted, from the point of suppressing the polymerization reaction between the (meth)acrylate compounds (2), a polymerization inhibitor may be used. The polymerization inhibitor is not particularly limited, and examples thereof include dibutylhydroxytoluene (BHT), hydroquinone (HQ), hydroquinone monomethyl ether (MEHQ), and phenothiazine (PTZ).

The amount of the polymerization inhibitor used may be from 0.001% by mass to 0.5% by mass, may be from 0.002% by mass to 0.3% by mass, may be from 0.005% by mass to 0.3% by mass, may be from 0.005% by mass to 0.1% by mass, or may be from 0.01% by mass to 0.1% by mass, with respect to 100% by mass of the total of the thiol compound (1) and the (meth)acrylate compound (2)

The monomer composition in the present disclosure may contain the (meth)acrylate (A) described above, and a (meth) acrylate (B) containing a (meth)acrylate other than the (meth)acrylate (A). Typically, the (meth)acrylate (B) is a polymerizable monomer. The (meth)acrylate (B) may be a main component monomer used in combination with the (meth)acrylate (A). For example, when the (meth)acrylate (A) is used as a diluting monomer, the monomer composition in the present disclosure can suppress the functional deterioration of the main component monomer.

When the (meth)acrylate (A) is used as the diluting monomer, for example, a compound used as a main component monomer in a composition for a dental material can be used as the (meth)acrylate (B), and the main component thereof is not particularly limited. The (meth)acrylate (B) may be a reaction product of the thiol compound (1) containing three or more thiol groups described above, an iso(thio)cyanate compound (3) containing two or more iso(thio)cyanate groups, and a (meth)acrylate compound (4) containing a (meth)acryloyloxy group and containing a hydroxy group.

Examples of the isocyanate compound (3) include aliphatic polyisocyanate compounds such as pentamethylene diisocyanate, hexamethylene diisocyanate, 2,2,4-trimethylhexanediisocyanate, 2,4,4-trimethylhexamethylene diisocyanate, lysine diisocyanatomethyl ester, lysine triisocyanate, m-xylylene diisocyanate, p-xylene diisocyanate, α, α, α', α'-tetramethylxylylene diisocyanate, bis(isocyanatomethyl)naphthalin, mesitylylene triisocyanate, bis(isocyanatomethyl)sulfide, bis(isocyanatoethyl)sulfide, bis(isocyanatomethyl)disulfide, bis(isocyanatoethyl)disulfide, bis(isocyanatomethylthio)methane, bis(isocyanatoethylthio)methane, bis(isocyanatoethylthio)ethane, and bis(isocyanatomethylthio)ethane; alicyclic polyisocyanate compounds such as isophorone diisocyanate, bis(isocyanatomethyl)cyclohexane, dicyclohexylmethane-4,4'-diisocyanate, cyclohexanediisocyanate, methylcyclohexanediisocyanate, dicyclohexyldimethylmethaneisocyanate, 2,5-bis(isocyanatomethyl)bicyclo-[2.2.1]-heptane, 2,6-bis(isocyanatomethyl)bicyclo-[2.2.1]-heptane, 3,8-bis(isocyanatomethyl)tricyclodecane, 3,9-bis(isocyanatomethyl)tricyclodecane, 4,8-bis(isocyanatomethyl)tricyclodecane, and 4,9-bis(isocyanatomethyl)tricyclodecane; aromatic polyisocyanate compounds such as phenylenediocyanate, 2,4-tolylene diisocyanate, 2,6-tolylene diisocyanate, 4,4'-diphenylmethane diisocyanate, and diphenyl sulfide-4,4-diisocyanate; and heterocyclic polyisocyanate compounds such as 2,5-diisocyanatothiophene, 2,5-bis(isocyanatomethyl)thiophene, 2,5-diisocyanatotetrahydrothiophene, 2,5-bis(isocyanatomethyl)tetrahydrothiophene, 3,4-bis(isocyanatomethyl)tetrahydrothiophene, 2,5-diisocyanato-1,4-dithiane, 2,5-bis(isocyanatomethyl)-1,4-dithiane, 4,5-diisocyanato-1,3-dithiolane, and 4, 5-bis(isocyanatomethyl)-1,3-dithiolane.

Examples of the isothiocyanate compound (3) include aliphatic polyisothiocyanate compounds such as hexamethylene diisothiocyanate, lysine diisothiocyanate methyl ester, lysine triisothiocyanate, m-xylylene diisothiocyanate, bis(isothiocyanatomethyl)sulfide, bis(isothiocyanatoethyl)sulfide, and bis(isothiocyanatoethyl)disulfide; alicyclic polyisothiocyanate compounds such as isophoron diisothiocianate, bis(isothiocyanatomethyl)cyclohexane, dicyclohexylmethane diisothiocianate, cyclohexane diisothiocianate, methylcyclohexane diisothiocianate, 2,5-bis(isothiocyanatomethyl)bicyclo-[2.2.1]-heptane, 2,6-bis(isothiocyanatomethyl)bicyclo-[2.2.1]-heptane, 3,8-bis(isothiocyanatomethyl)tricyclodecane, 3,9-bis(isothiocyanatomethyl)tricyclodecane, 4,8-bis(isothiocyanatomethyl)tricyclodecane, and 4,9-bis(isothiocyanatomethyl)tricyclodecane; aromatic polyisothiocyanate compounds such as tolylene diisocyanate, 4,4-diphenylmethane diisothiocyanate, and diphenyl disulfide-4,4-diisocyanate; and sulfur-containing heterocyclic polyisothiocyanate compounds such as 2,5-diisothiocyanatothiophene, 2,5-bis(isothiocyanatomethyl)thiophene, 2,5-isothiocyanatotetrahydrothiophene, 2,5-bis(isothiocyanatomethyl)tetrahydrothiophene, 3,4-bis(isothiocyanatomethyl)tetrahydrothiophene, 2,5-diisothiocyanato-1,4-dithiane, 2,5-bis(isothiocyanatomethyl)-1,4-dithiane, 4,5-diisothiocyanato-1,3-dithiolane, and 4,5-bis(isothiocyanatomethyl)-1,3-dithiolane.

Examples of the (meth)acrylate compound (4) include 2-hydroxyethyl (meth)acrylate, 2-hydroxypropyl (meth)acrylate, 2-hydroxybutyl (meth)acrylate, 2-hydroxy-3-phenoxypropyl (meth)acrylate, 4-hydroxybutyl (meth)acrylate, and 1, 4-cyclohexanedimethanol mono(meth)acrylate.

(Method 2 of Manufacturing (Meth)Acrylate (A))

Hereinafter, the method 2 of manufacturing the (meth)acrylate (A) in the present disclosure will be described. The method 2 of manufacturing the (meth)acrylate (A) in the present disclosure includes a step of preparing a composition containing the thiol compound (1) described above, the (meth)acrylate compound (2) described above, and an alkylphosphine compound (5); and a step of producing the (meth)acrylate (A) containing a sulfide bond by reacting the thiol compound (1) and the (meth)acrylate compound (2). In the method 2 of manufacturing the (meth)acrylate in the present disclosure, the thiol compound (1) and the (meth)acrylate compound (2) are reacted using the specific catalyst (the alkylphosphine compound (5)). The description of matters common to the method 1 of manufacturing the (meth)acrylate (A) will be omitted.

In the step of preparing the composition described above in the method 2 of manufacturing the (meth)acrylate (A), the above described composition may be prepared by adding the thiol compound (1), the (meth)acrylate compound (2) and the alkylphosphine compound (5) in a container and mixing them.

(Alkylphosphine Compound (5))

The alkylphosphine compound (5) functions a catalyst in the reaction of the thiol group contained in the thiol compound (1) and the (meth)acryloyloxy group contained in the (meth)acrylate compound (2).

The alkylphosphine compound (5) is not limited as long as a compound containing one or more alkyl group, and, from the point of suppressing the gelation and proceeding with the reaction preferably, a trialkylphosphine compound described above is preferable. The alkylphosphine compound (5) may be used singly or in combination of two or more.

A content of the alkylphosphine compound (5) is preferably 0.2 parts by mass or less with respect to 100 parts by mass of the composition. From the point of reducing the amount used and proceeding with the reaction preferably, the content of the alkylphosphine compound (5) is preferably from 0.01 parts by mass to 0.2 parts by mass, more preferably from 0.03 parts by mass to 0.15 parts by mass, and further preferably from 0.05 parts by mass to 0.1 parts by mass. The entire amount of the alkylphosphine compound (5) may be added to the composition by the start of the reaction, or the alkylphosphine compound (5) may be added to the reaction system sequentially or divided as needed. When the alkylphosphine compound (5) is added to the reaction system sequentially or divided, the content described above of the alkylphosphine compound (5) refers to the content in the composition after the entire amount of the alkylphosphine compound (5) is added to the reaction system.

The method 2 of manufacturing the (meth)acrylate includes the step of producing the (meth)acrylate (A) containing a sulfide bond by reacting the thiol compound (1) and the (meth)acrylate compound (2). Hereinafter, the reaction conditions will be described.

The reaction temperature is not particularly limited, and, from the point of suppressing the gelation and suppressing the generation of by-products, is preferably 80° C. or less, more preferably 60° C. or less, further preferably 55° C. or less, and particularly preferably 50° C. or less. From the point of shortening the reaction time, the reaction temperature is preferably 0° C. or more, more preferably 20° C. or more, further preferably 30° C. or more, and particularly preferably 35° C. or more.

(Method of Manufacturing (Meth)Acrylate (B))

The (meth)acrylate (B) can be obtained by reacting the thiol compound (1), the iso(thio)cyanate compound (3), and the (meth)acrylate compound (4), and this reaction can be carried out by a known method or a method conforming to the known.

When the thiol compound (1), the iso(thio)cyanate compound (3), and the (meth)acrylate compound (4) are reacted, the above described catalyst, polymerization inhibitor and the like may be used.

The reaction temperature is not particularly limited, and, from the point of shortening the reaction time and suppressing the generation of by-products, is preferably from 0° C. to 120° C., more preferably from 20° C. to 100° C., and further preferably from 50° C. to 90° C.

When the thiol compound (1), the iso(thio)cyanate compound (3), and the (meth)acrylate compound (4) are reacted, a ratio (the number of moles of thiol group/the number of moles of iso(thio)cyanate group) of the number of moles of the thiol group contained in the thiol compound (1) with respect to the number of moles of the iso(thio)cyanate group contained in the iso(thio)cyanate compound (3) is preferably from 0.01 to 0.20, and more preferably from 0.01 to 0.18.

A ratio (the total number of moles/the number of moles of iso(thio)cyanate group) of the total number of moles of the thiol group contained in the thiol compound (1) and moles of an active hydrogen group contained in the (meth)acrylate compound (4) with respect to the number of moles of the iso(thio)cyanate group contained in the iso(thio)cyanate compound (3) is preferably from 0.70 to 1.30, more preferably from 0.70 to 1.20, and further preferably from 0.90 to 1.10.

By satisfying the above described ratio of the number of moles, it is possible to more preferably obtain the (meth)acrylate (B) capable of obtaining a cured product having excellent heat resistance, solvent resistance and impact resistance. Further, a monomer composition containing the (meth)acrylate (B) is suitable as a composition for a dental material.

An example of the (meth)acrylate (B) is a compound represented by the following general formula (A).

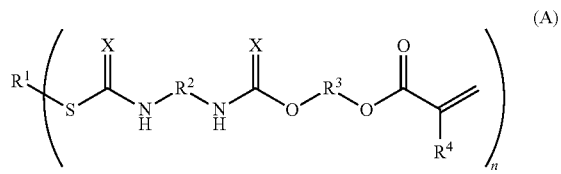

In the general formula (A), $R^1$ represents a residue of a bifunctional to tetrafunctional thiol compound from which all thiol groups have been removed; $R^2$ represents a residue of an iso(thio)cyanate compound from which all iso(thio) cyanate groups have been removed; $R^3$ represents a residue of a (meth)acrylate containing a hydroxy group from which a (meth)acryloyloxy group and the hydroxy group have been removed; and $R^4$ represents a hydrogen atom or a methyl group. X represents an oxygen atom or a sulfur atom. n is an integer from 2 to 4, and preferably 3 or 4. Plural instances of $R^2$ to $R^4$ may be the same or different, respectively. The bifunctional to tetrafunctional thiol compound may be the thiol compound (1) described above, the iso(thio)cyanate compound may be the iso(thio)cyanate compound (3) described above, or the (meth)acrylate containing a hydroxy group may be the (meth)acrylate (4) described above.

In the general formula (A), $R^1$ is the same as the preferred configuration of $R^1$ in the general formula (1) described above, and $R^4$ is the same as the preferred configuration of $R^2$ in the general formula (1) described above. It is preferable that each of the plurality of X is an oxygen atom or a sulfur atom.

When the monomer composition in the present disclosure contains the (meth)acrylate (B), from the point of improving handleability of the monomer composition and the point of suppressing the functional deterioration of the main component monomer, a content of the (meth)acrylate (A) is preferably from 5% by mass to less than 50% by mass, more preferably from 10% by mass to 40% by mass, and further preferably from 15% by mass to 30% by mass, with respect to the total amount of the monomer composition.

When the monomer composition in the present disclosure contains the (meth)acrylate (B), from the point of improving handleability of the monomer composition and the point of suppressing the functional deterioration of the main component monomer, a content of the (meth)acrylate (B) is preferably from more than 50% by mass to 95% by mass, more preferably from 60% by mass to 90% by mass, and further preferably from 70% by mass to 85% by mass, with respect to the total amount of the monomer composition.

(Method of Manufacturing Monomer Composition)

The method of manufacturing the monomer composition in the present disclosure includes a step of obtaining the (meth)acrylate (A) by the method of manufacturing the (meth)acrylate in the present disclosure, and a step of producing the monomer composition by mixing the (meth) acrylate (A), and the (meth)acrylate (B) containing a (meth) acrylate other than the (meth)acrylate (A).

Modified Example of Monomer Composition for Dental Material

The monomer composition for a dental material may contain the (meth)acrylate (A) containing a sulfide bond and a ester bond, or may contain a structure represented by the following general formula (B).

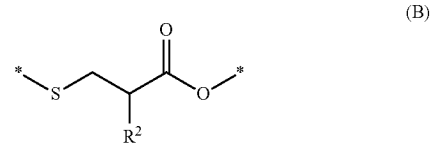

In general formula (B), $R^2$ represents a hydrogen atom or a methyl group.

[Molded Body]

A molded body including a cured product of the monomer composition for a dental material in the present disclosure. For example, by curing the monomer composition containing the (meth)acrylate (A) and the (meth)acrylate (B) which is a compound represented by the general formula (a), it is possible to obtain the cured product having excellent heat resistance, solvent resistance and impact resistance.

[Composition for Dental Material]

A composition for a dental material in the present disclosure contains the monomer composition for a dental material in the present disclosure, a polymerization initiator, and a filler. This composition for a dental material has room temperature polymerizability, thermally polymerizability, or photo polymerizability, and can be preferably used as, for example, a dental restorative material.

A blending amount of monomer composition is preferably from 20% by mass to 80% by mass, and more preferably from 20% by mass to 50% by mass, with respect to 100% by mass of the composition for a dental material.

As the polymerization initiator, a general polymerization initiator used in the dental field can be used, and the polymerization initiator is usually selected in consideration of polymerizability and polymerization conditions of the polymerizable compounds such as the (meth)acrylate (A) and the (meth)acrylate (B) contained in the composition for a dental material.

When performing room temperature polymerization, as the polymerization initiator, for example, a redox-based polymerization initiator formed by a combination of an oxidizing agent and a reducing agent is preferable. When the redox-based polymerization initiator is used, the oxidizing agent and the reducing agent may be packaged separately, and both may be mixed just before use.

The oxidizing agent is not particularly limited, and examples thereof include organic peroxides such as diacyl peroxides, peroxyesters, dialkyl peroxides, peroxyketals, ketone peroxides and hydroperoxides. Examples of the organic peroxides include diacyl peroxides such as benzoyl peroxide, 2,4-dichlorobenzoyl peroxide, and m-toluoyl peroxide; peroxyesters such as t-butylperoxybenzoate, bis-t-butylperoxyisophthalate, 2,5-dimethyl-2,5-bis(benzoylperoxy)hexane, t-butylperoxy-2-ethylhexanoate, and t-butylperoxyisopropyl carbonate; dialkyl peroxides such as dicumyl peroxide, di-t-butyl peroxide, and lauroyl peroxide; peroxyketals such as 1,1-bis(t-butylperoxy)-3,3,5-trimethylcyclohexane; ketone peroxides such as methyl ethyl ketone peroxide; and hydroperoxides such as t-butyl hydroperoxide.

The reducing agent is not particularly limited, and usually a tertiary amine is used as the reducing agent. Examples of the tertiary amine include N, N-dimethylaniline, N, N-dimethyl-p-toluidine, N, N-dimethyl-m-toluidine, N, N-diethyl-p-toluidine, N, N-dimethyl-3,5-dimethylaniline, N, N-dimethyl-3,4-dimethylaniline, N, N-dimethyl-4-ethylaniline, N, N-dimethyl-4-i-propylaniline, N, N-dimethyl-4-t-butylaniline, N, N-dimethyl-3,5-di-t-butylaniline, N, N-bis(2-hydroxyethyl)-p-toluidine, N, N-bis(2-hydroxyethyl)-3,5-dimethyl aniline, N, N-bis(2-hydroxyethyl)-3,4-dimethylaniline, N, N-bis(2-hydroxyethyl)-4-ethylaniline, N, N-bis(2-hydroxyethyl)-4-i-propylaniline, N, N-bis(2-hydroxyethyl)-4-t-butylaniline, N, N-di(2-hydroxyethyl)-3,5-di-i-propylaniline, N, N-bis(2-hydroxyethyl)-3,5-di-t-butylaniline, ethyl 4-dimethylaminobenzoate, n-butoxyethyl 4-dimethylaminobenzoate, (2-methacryloyloxy)ethyl 4-dimethylaminobenzoate, trimethylamine, triethylamine, N-methyldiethanolamine, N-ethyldiethanolamine, N-n-butyldiethanolamine, N-lauryldiethanolamine, triethanolamine, (2-dimethylamino)ethylmethacrylate, N, N-bis(methacryloyloxyethyl)-N-methylamine, N, N-bis(methacryloyloxyethyl)-N-ethylamine, N, N-bis(2-hydroxyethyl)-N-methacryloyloxyethylamine, N, N-bis(methacryloyl)oxyethyl)-N-(2-hydroxyethyl)amine, and tris (methacryloyloxyethyl)amine.

In addition to these organic peroxide/amine-based polymerization initiators, redox-based polymerization initiators such as cumenehydroperoxide/thiourea-based, ascorbic acid/$Cu^2$ salt-based, and organic peroxide/amine/sulfinic acid (or salt thereof)-based can be used. as the polymerization initiator, tributylborane, organic sulfinic acid and the like are also preferably used.

When performing thermal polymerization by heating, the polymerization initiators such as peroxides and azo compounds are preferable.

The peroxide is not particularly limited, and example thereof include benzoyl peroxide, t-butyl hydroperoxide, and cumene hydroperoxide. The azo compound is not particularly limited, and example thereof include azobisisobutyronitrile.

When performing photopolymerization by visible light irradiation, redox-based initiators such as α-diketone/tertiary amine, α-diketone/aldehyde, and α-diketone/mercaptan are preferable.

Photopolymerization initiator is not particularly limited, and examples thereof include α-diketone/reducing agent, ketal/reducing agent, and thioxanthone/reducing agent. Examples of the α-diketone include camphorquinone, benzyl, and 2,3-pentandione. Examples of the ketal include benzyldimethyl ketal, and benzyldiethyl ketal. Examples of the thioxanthone include 2-chlorothioxanthone, and 2,4-diethylthioxanthone. Examples of the reducing agent include Michler's ketone; tertiary amines such as 2-(dimethylamino)ethyl methacrylate, N, N-bis[(meth)acryloyloxyethyl]-N-methylamine, ethyl-N, N-dimethylamino benzoate, butyl-4-dimethylamino benzoate, butoxyethyl-4-dimethylamino benzoate, N-methyldiethanolamine, 4-dimethylaminobenzophenone, N, N-bis(2-hydroxyethyl)-p-toluidine, and dimethylaminophenanthol; aldehydes such as citronellal, laurylaldehyde, phthaldialdehyde, dimethylaminobenzaldehyde, and terephthalaldehyde; compounds containing a thiol group such as 2-mercaptobenzoxazole, decanethiol, 3-mercaptopropyltrimethoxysilane, 4-mercaptoacetophenone, thiosalicylic acid, and thiobenzoic acid. Polymerization initiators such as α-diketone/organic peroxide/reducing agent-based polymerization initiators prepared by adding the organic peroxide to these redox-based polymerization initiators are also preferably used.

When performing photopolymerization by ultraviolet irradiation, the photopolymerization initiators such as benzoin alkyl ether, and benzyl dimethyl ketal are preferable. The photopolymerization initiators of (bis)acylphosphine oxides are also preferably used.

Of the (bis)acylphosphine oxides, examples of acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, and benzoyldi-(2,6-dimethylphenyl)phosphonate. Examples of the (bis) acylphosphine oxides include bis-(2,6-dichlorobenzoyl) phenylphosphine oxide, bis-(2,6-dichlorobenzoyl)-2,5-dimethylphenylphosphine oxide, bis-(2,6-dichlorobenzoyl)-4-propyl phenylphosphine oxide, bis-(2,6-dichlorobenzoyl)-1-naphthylphosphine oxide, bis-(2,6-dimethoxybenzoyl) phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide, and (2,5,6-trimethylbenzoyl)-2,4,4-trimethylpentylphosphine oxide. The photopolymerization initiators of these (bis) acylphosphine oxides may be used singly or in combination with reducing agents such as various amines, aldehydes, mercaptans and sulfinates. The photopolymerization initiators of these (bis)acylphosphine oxides may be used in combination with the above described visible light photopolymerization initiators.

The polymerization initiators described above may be used singly or in combination of two or more. A blending amount of the polymerization initiator is preferably from 0.01% by mass to 20% by mass, and more preferably from 0.1% by mass to 5% by mass, with respect to 100% by mass of the composition for a dental material.

As the filler, a general filler used in the dental field can be used. Fillers are usually roughly classified into organic fillers and inorganic fillers.

Examples of organic fillers include fine powders of polymethyl methacrylate, polyethylmethacrylate, methyl methacrylate-ethyl methacrylate copolymer, crosslinked polymethylmethacrylate, crosslinked polyethyl methacrylate, ethylene-vinyl acetate copolymer, and styrene-butadiene copolymer.

Examples of inorganic fillers include fine powders of various glasses (mainly silicon dioxide, and if necessary, containing oxides such as heavy metals, boron, and aluminum), various ceramics, diatomaceous earth, kaolin, clay minerals (montmorillonite, and the like), activated clay, synthetic zeolite, mica, calcium fluoride, ytterbium fluoride, calcium phosphate, barium sulfate, zirconium dioxide, titanium dioxide, and hydroxyapatite. Specific examples of these inorganic fillers include barium borosilicate glasses (Kimble Raysorb T3000, Shot 8235, Shot GM27884, Shot GM39923, and the like), strontium boroaluminosilicate glasses (Raysorb T4000, Shot G018-093, Shot GM32087, and the like), lantern glasses (Shot GM31684, and the like), fluoroaluminosilicate glasses (shot G018-091, shot G018-117, and the like), and boroaluminosilicate glasses containing zirconium, cesium, and the like (shot G018-307, G018-308, G018-310, and the like).

An organic-inorganic composite filler obtained by preliminarily adding a polymerizable compound to an inorganic filler to form a paste, then polymerizing and curing the polymerizable compound, and pulverizing the mixture may be used.

In the composition for a dental material, a composition mixed with a microfiller having a particle size of 0.1 μm or less is one of the preferred aspects for a dental composite resin. As the material of the filler having such a small particle size, silica (for example, trade name Aerosil), alumina, zirconia, titania and the like are preferable. The mixture of such an inorganic filler having a small particle size is advantageous in obtaining the polishing smoothness of the cured product of the composite resin.

These fillers may be surface-treated with a surface-treating agent such as a silane coupling agent, depending on the purpose. As the surface-treating agent, known silane coupling agents may be used, and for example organic silicon compounds such as methacryloxyalkyltrimethoxysilane (carbon number between methacryloxy group and silicon atom: 3 to 12), methacryloxyalkyltriethoxysilane (carbon number between methacryloxy group and silicon atom: 3 to 12), vinyl trimethoxysilane, vinyl ethoxysilane, and vinyl triacetoxysilane may be used. An amount of the surface-treating agent is preferably from 0.1% by mass to 20% by mass, and more preferably from 1% by mass to 10% by mass, with respect to 100% by mass of the filler before surface treatment.

These fillers may be used singly or in combination of two or more. A blending amount of the filler may be appropriately determined in consideration of the operability (viscosity) of the composition for a dental material (for example, composite resin paste), the mechanical property of the cured product, and the like. The blending amount of the filler is preferably from 10 parts by mass to 2000 parts by mass, more preferably from 50 parts by mass to 1000 parts by mass, and further preferably from 100 parts by mass to 600 parts by mass, with respect to 100 parts by mass of the all components other than the filler contained in the composition for a dental material.

The composition for a dental material in the present disclosure may appropriately contain the monomer composition in the present disclosure, a polymerization initiator, and the component other than a filler, depending on the purpose. For example, the above described polymerization inhibitor for improving storage stability may be contained. In order to adjust a color tone, a pigment such as a known pigment or dye may be contained. In order to improve the strength of the cured product, a reinforcing material such as known fiber may be contained. The composition for a dental material in the present disclosure may contain additives such as a bactericide, a disinfectant, a stabilizer, and a preservative as long as the effect of the present invention is exhibited.

The composition for a dental material in the present disclosure can be cured under appropriate conditions in the polymerization method of the above described polymerization initiator. For example, in the case of the composition for a dental material in the present disclosure containing a photopolymerization initiator by visible light irradiation, a desired cured product can be obtained by processing the composition for a dental material into a predetermined shape, and then irradiating the processed composition with visible light for a predetermined time using a known light irradiation device. Conditions such as irradiation intensity and irradiation intensity can be appropriately changed according to the curability of the composition for a dental material. Further, the mechanical property of the cured product may be improved by heat-treating the cured product cured by light irradiation such as visible light irradiation, under more appropriate conditions.

The cured product, obtained as described above, of the composition for a dental material in the present disclosure is preferably used as the dental material.

The method of using the composition for a dental material in the present disclosure is not particularly limited as long as it is generally known as a method of using a dental material. For example, when the composition for a dental material in the present disclosure is used as a composite resin for filling a caries cavity, the purpose can be achieved by filling the cavity in the oral cavity with the composition for a dental material and then photocured using a known light irradiation device. When the composition is used as a composite resin for a crown, the desired crown material can be obtained by processing the composition for a dental material into a predetermined shape, and then photocured using a known light irradiation device, and further performing heat treatment under predetermined conditions.

The composition for a dental material and the dental material in the present disclosure can be preferably used as, for example, a dental restorative material, a denture base resin, a denture base lining material, an impression material, a joint wearing material (resin cement, resin-added glass ionomer cement and the like), a dental adhesive (an orthodontic adhesive, a cavity coating adhesive and the like), a tooth fissure sealant, resin block for CAD/CAM, temporary crown, and an artificial tooth material. When the dental restorative material is classified according to the applicable range, it can be classified into a composite resin for a crown, a composite resin for filling a caries cavity, a composite resin for abutment construction, a composite resin for filling restoration, and the like.

(Method of Manufacturing Composition for Dental Material)

A method of manufacturing a composition for a dental material in the present disclosure includes a step of preparing the (meth)acrylate (A) by the method of manufacturing the (meth)acrylate in the present disclosure, and a step of producing a composition for a dental material by mixing the (meth)acrylate (A), the (meth)acrylate (B), the polymerization initiator, and the filler. The obtained composition for a dental material has room temperature polymerizability, thermally polymerizability, or photo polymerizability, and can be preferably used as, for example, a dental restorative material. The method of manufacturing the monomer composition for a dental material may include a step of preparing the monomer composition by the method of manufacturing the monomer composition in the present disclosure, and a step of producing the composition for a dental material by mixing the monomer composition, the polymerization initiator, and the filler.

[Dental Material]

A dental material in the present disclosure includes a cured product of the composition for a dental material in the present disclosure. The curing conditions of the composition for a dental material may be appropriately determined according to the composition of the composition for a dental material, the use of the dental material, and the like.

(Method of Manufacturing Dental Material)

The method of manufacturing the dental material in the present disclosure includes a step of preparing a composition for the dental material by the method of manufacturing the composition for a dental material, and a step of producing the dental material by curing the composition for a dental material. The curing conditions may be appropriately determined according to the composition of the composition for a dental material, the usage of the dental material and the like.

EXAMPLES

The invention will now be described more concretely by way of examples thereof; however, the invention is not limited to the following examples.

The abbreviations of the compounds used in the examples of the present invention are shown below.

NPG: neopentyldimethacrylate
3G: triethylene glycol dimethacrylate
HPA: 2-hydroxypropyl acrylate
XDI: m-xylylene diisocyanate
THIOL 1: 4-mercaptomethyl-1,8-dimercapto-3,6-dithiaoctane
THIOL 2: a mixture of 5,7-dimercaptomethyl-1,11-dimercapto-3,6,9-trithiandecan, 4,7-dimercaptomethyl-1,11-dimercapto-3,6,9-trithiandecan, and 4,8-dimercaptomethyl-1,11-dimercapto-3,6,9-trithiaundecane
THIOL 3: pentaerythritol tetrakis(3-mercaptopropionate)
THIOL 4: trimethylolpropane tris(3-mercaptopropionate)
THIOL 5: tris-[(3-mercaptopropionyloxy)-ethyl]-isocyanurate
TBP: tributylphosphine
TPP: triphenylphosphine
DBTDL: dibutyltin dilaurate
BHT: dibutylhydroxytoluene
TUA: thiourethane acrylate
CQ: camphorquinone
DMAB2-BE: 2-butoxyethyl 4-(dimethylamino)benzoate

[Method of Measuring IR Spectrum]

IR spectrum of (meth)acrylate obtained in each example was measured by using Fourier Transform Infrared Spectroscopy, Spectrum Two/UATR (Universal Attenuated Total Reflectance) manufactured by PerkinElmer Japan Co., Ltd.

The (meth)acrylate obtained in each example was left to stand at 20° C., for 24 hours, and then the infrared absorption spectrum of the (meth)acrylate was measured at 20° C.

[Method of Bending Test]

The method of a bending test in the examples and the comparative examples in the present invention is shown below.

(Preparation of Test Piece for Bending Test)

The composition for a dental material was prepared by adding 0.05 parts by mass of CQ and 0.05 parts by mass of DMAB2-BE to 10 parts by mass of the monomer composition obtained in each example and comparative example, stirring the mixture at room temperature until uniform, further adding 15 parts by mass of silica glass (Fusedex-X (Tatsumori Co., Ltd.)), stirring the mixture using a mortar until uniform, and then defoaming the mixture. The obtained composition for a dental material was placed in a stainless steel mold of 2 mm×2 mm×25 mm, and light was irradiated for 3 minutes on each side, that is, for 6 minutes on both sides using a visible light irradiation device (Solidayite V manufactured by Shofu Inc.). Further, the test piece taken out from the mold was heat-treated in an oven at 130° C. for 2 hours. After cooling the test piece taken out from the oven to room temperature, the test piece was immersed in distilled water in a sealable sample bottle and held at 37° C. for 24 hours. The test piece after immersed was used as the test piece (test piece for bending test).

(Bending Test)

A three-point bending test was performed by using the test piece prepared by the above method and a testing machine (Autograph EZ-S manufactured by Shimadzu Corporation) at a distance between fulcrums of 20 mm and a crosshead speed of 1 mm/min.

[Method of Measuring Viscosity]

The Viscosity of thiourethane acrylate and (meth)acrylates in the examples and the comparative examples was measured by using E-type viscometer (TVE-22H manufactured by Toki Sangyo Co.,Ltd). The temperature was controlled to 65° C. or 25° C. using a circulating constant temperature water tank.

[Method of Measuring Refractive Index]

The refractive index of the (meth)acrylate in the examples and the comparative examples was measured by using abbe type full digital refractive index meter (Abbemat 550 manufactured by Anton Paar). The temperature was controlled to 25° C.

[Manufacturing Method of Thiourethane Acrylate]

0.1 parts by mass of DBTDL, 0.05 parts by mass of BHT, 21.35 parts by mass of XDI, and 2.09 parts by mass of a mixture (T4 in Table 1 described later) of 5,7-dimercaptomethyl-1,11-dimercapto-3,6,9-trithiaundecane, 4,7-dimercaptomethyl-1,11-dimercapto-3,6,9-trithiaundecane, and 4,8-dimercaptomethyl-1,11-dimercapto-3,6,9-trithiaundecane were charged in a 100 mL 4-neck flask equipped with a well-dried stirring blade and a thermometer, and after dissolving them to make a homogeneous solution and reacting them at 80° C. for 4 hours, a solution containing an intermediate was obtained. The temperature of this solution was raised to 90° C., and 26.56 parts by mass of HPA was dropped over 1 hour. Since the internal temperature increased due to the heat of reaction during the dropping, the dropping amount was controlled so as to be 90° C. or lower. After dropping the entire amount of HPA, the reaction was carried out for 10 hours while maintaining the reaction temperature at 90° C. At this time, the progress of the reaction was followed by HPLC analysis to confirm the end point of the reaction. By discharging the product from the reactor, 50 g of thiourethane acrylate (TUA) was obtained. The viscosity at 65° C. was 1790 mPa·s. The refractive index at 25° C. was 1.5271.

Example 1A 0.04 parts by mass of TBP, 10.0 parts by mass of pentaerythritol tetrakis(3-mercaptopropionate) (T1 in Table 1), and 45.0 parts by mass of NPG (M1 in Table 1) were charged in a 100 mL 4-neck flask equipped with a well-dried stirring blade and a thermometer, and after dissolving them to make a homogeneous solution, the temperature of the solution was raised to 40° C. After raising the temperature, the reaction was carried out for 3 hours while maintaining the reaction temperature at 40° C. At this time, the progress of the reaction was followed by IR analysis to confirm the end point of the reaction. By discharging the product from the reactor, 50 g of ene-thiol methacrylate (A-1) was obtained. The viscosity at 25° C. was 29 mPa·s. The refractive index at 25° C. was 1.4639. IR spectrum of ene-thiol methacrylate (A-1) is shown in FIG. 1. 3.0 parts by mass of the obtained ene-thiol methacrylate (A-1) and 12.0 parts by mass of TUA were placed in a container and stirred at 50° C. until uniform to obtain a monomer composition (1). By using the obtained monomer composition (1), the composition (1) for a dental material, and the test piece (test piece for bending test) were obtained according to the methods described in the sections of (Preparation of Test Piece for Bending Test) and (Bending Test). When the bending test was carried out, the elastic modulus was 9300 MPa, the breaking strength was 216 MPa, and the breaking energy was 36 mJ.

Examples 2A to 48A 50 g of ene-thiol methacrylates (A-2) to (A-48) were obtained in the same manner as Example 1A except that the thiol compounds and (meth)acrylate compounds were changed to the compounds shown in Tables 1 to 4, and the parts by mass shown in Tables 1 to 4 were charged. The viscosity at 25° C. and the refractive index at 25° C. are shown in Tables 1 to 4. IR spectrums of ene-thiol methacrylates (A-2) to (A-48) are shown in FIG. 2 to FIG. 48. A monomer compositions (2) to (48) were obtained in the same manner as Example 1A except that ene-thiol methacrylate (A-1) was respectively changed to ene-thiol methacrylates (A-2) to (A-48). By using the obtained monomer compositions (2) to (48), the compositions (2) to (48) for a dental material, and the test piece (test piece for bending test) were obtained according to the methods described in the sections of (Preparation of Test Piece for Bending Test) and (Bending Test), and then the bending test was carried out. The elastic modulus, the breaking strength, and the breaking energy are shown in Tables 1 to 4.

Figure 49:
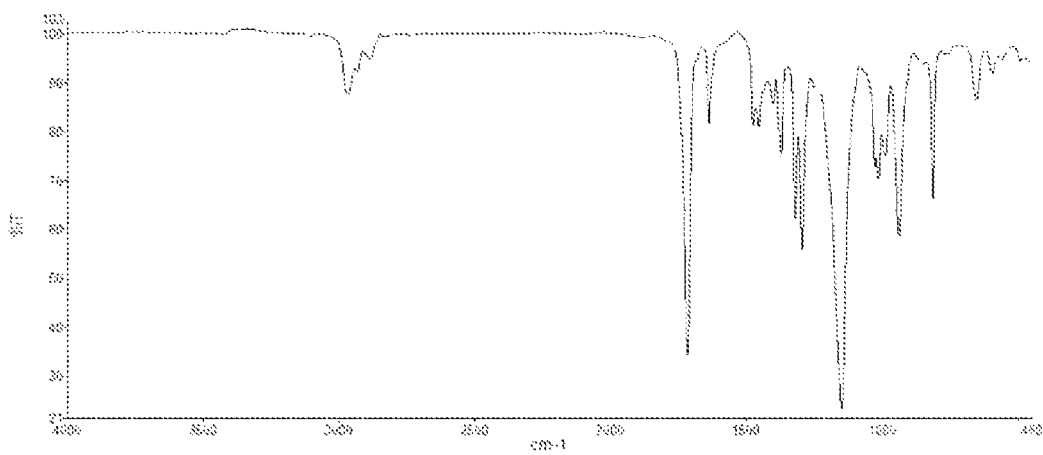
FIG. 49 shows IR spectrum of ene-thiol methacrylate (A-49) obtained in Example 49A.

Example 49A 0.04 parts by mass of TBP, 2.5 parts by mass of trimethylolpropane tris(3-mercaptopropionate) (T2 in Table 5), 2.5 parts by mass of 4-mercaptomethyl-1,8-dimercapto-3,6-dithiaoctane (T3 in Table 5), and 45.0 parts by mass of NPG (M1 in Table 5) were charged in a 100 mL 4-neck flask equipped with a well-dried stirring blade and a thermometer, and after dissolving them to make a homogeneous solution, the temperature of the solution was raised to 40° C. After raising the temperature, the reaction was carried out for 3 hours while maintaining the reaction temperature at 40° C. At this time, the progress of the reaction was followed by IR analysis to confirm the end point of the reaction. By discharging the product from the reactor, 50 g of ene-thiol methacrylate (A-49) was obtained. The viscosity at 25° C. was 28 mPa·s. The refractive index at 25° C. was 1.4682. IR spectrum of ene-thiol methacrylate (A-49) is shown in FIG. 49. 3.0 parts by mass of the obtained ene-thiol methacrylate (A-49) and 12.0 parts by mass of TUA were placed in a container and stirred at 50° C. until uniform to obtain a monomer composition (49). By using the obtained monomer composition (49), the composition (49) for a dental material, and the test piece (test piece for bending test) were obtained according to the methods described in the sections of (Preparation of Test Piece for Bending Test) and (Bending Test). When the bending test was carried out, the elastic modulus was 11370 MPa, the breaking strength was 221 MPa, and the breaking energy was 21 mJ. The results are shown in Table 5.

Figure 50:
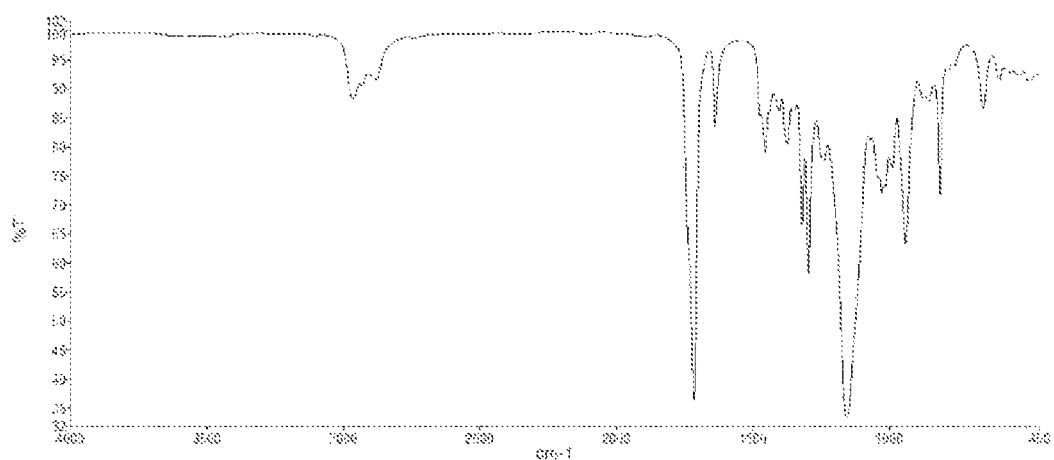
FIG. 50 shows IR spectrum of ene-thiol methacrylate (A-50) obtained in Example 50A.

Example 50A 0.04 parts by mass of TBP, 5.0 parts by mass of trimethylolpropane tris(3-mercaptopropionate) (T2 in Table 6), 22.5 parts by mass of NPG (M1 in Table 6), and 22.5 parts by mass of 3G (M2 in table 6) were charged in a 100 mL 4-neck flask equipped with a well-dried stirring blade and a thermometer, and after dissolving them to make a homogeneous solution, the temperature of the solution was raised to 40° C. After raising the temperature, the reaction was carried out for 3 hours while maintaining the reaction temperature at 40° C. At this time, the progress of the reaction was followed by IR analysis to confirm the end point of the reaction. By discharging the product from the reactor, 50 g of ene-thiol methacrylate (A-50) was obtained. The viscosity at 25° C. was 144 mPa·s. The refractive index at 25° C. was 1.4762. IR spectrum of ene-thiol methacrylate (A-50) is shown in FIG. 50. 3.0 parts by mass of the obtained ene-thiol methacrylate (A-50) and 12.0 parts by mass of TUA were placed in a container and stirred at 50° C. until uniform to obtain a monomer composition (50). By using the obtained monomer composition (50), the composition (50) for a dental material, and the test piece (test piece for bending test) were obtained according to the methods described in the sections of (Preparation of Test Piece for Bending Test) and (Bending Test). When the bending test was carried out, the elastic modulus was 7910 MPa, the breaking strength was 228 MPa, and the breaking energy was 61 mJ. The results are shown in Table 6.

Comparative Example 1A 3.0 parts by mass of NPG and 12.0 parts by mass of TUA were placed in a container and stirred at 50° C. until uniform to obtain a monomer composition (51). By using the obtained monomer composition (51), the composition (51) for a dental material, and the test piece (test piece for bending test) were obtained according to the methods described in the sections of (Preparation of Test Piece for Bending Test) and (Bending Test). When the bending test was carried out, the elastic modulus was 9350 MPa, the breaking strength was 178 MPa, and the breaking energy was 19 mJ. Further, the viscosity of NPG at 25° C. was 6 mPa·s. The results are shown in Tables 1, 3, and 5.

Comparative Example 2A 3.0 parts by mass of 3G and 12.0 parts by mass of TUA were placed in a container and stirred at 50° C. until uniform to obtain a monomer composition (52). By using the obtained monomer composition (52), the composition (52) for a dental material, and the test piece (test piece for bending test) were obtained according to the methods described in the sections of (Preparation of Test Piece for Bending Test) and (Bending Test). When the bending test was carried out, the elastic modulus was 8810 MPa, the breaking strength was 200 MPa, and the breaking energy was 32 mJ. Further, the viscosity of 3G at 25° C. was 9 mPa·s. The results are shown in Table 2, and 4.

Comparative Example 3A 1.5 parts by mass of NPG, 1.5 parts by mass of 3G, and 12.0 parts by mass of TUA were placed in a container and stirred at 50° C. until uniform to obtain a monomer composition (53). By using the obtained monomer composition (53), the composition (53) for a dental material, and the test piece (test piece for bending test) were obtained according to the methods described in the sections of (Preparation of Test Piece for Bending Test) and (Bending Test). When the bending test was carried out, the elastic modulus was 7900 MPa, the breaking strength was 197 MPa, and the breaking energy was 33 mJ. Further, the viscosity of the mixture of 1.5 parts by mass of NPG and 1.5 parts by mass of 3G at 25° C. was 7 mPa·s. The results are shown in Table 6.

TABLE 1

| | | Preparation ratio | | | Monomer properties | | Cured product properties | | |
| --- | --- | --- | --- | --- | --- | --- | --- | --- | --- |
| | | thiol (pbW) | methacrylate (pbW) | M/T (pbW/pbW) | Viscosity [mPa · s] | Refractive index | Elastic modulus [MPa] | Breaking strength [MPa] | Breaking energy [mJ] |
| Example | 1A | T1 5.0 | M1 45.0 | 9.00 | 29 | 1.4639 | 9300 | 216 | 36 |
| | 2A | T1 7.5 | M1 42.5 | 5.67 | 84 | 1.4698 | 9370 | 247 | 53 |
| | 3A | T1 10.0 | M1 40.0 | 4.00 | 306 | 1.4759 | 8680 | 227 | 52 |
| | 7A | T2 5.0 | M1 45.0 | 9.00 | 22 | 1.4625 | 9320 | 190 | 24 |
| | 8A | T2 7.5 | M1 42.5 | 5.67 | 51 | 1.4681 | 8710 | 196 | 28 |
| | 9A | T2 10.0 | M1 40.0 | 4.00 | 134 | 1.4734 | 8570 | 202 | 34 |
| | 13A | T3 5.0 | M1 45.0 | 9.00 | 36 | 1.4749 | 9050 | 234 | 49 |
| | 14A | T3 7.5 | M1 42.5 | 5.67 | 110 | 1.4846 | 9330 | 213 | 27 |
| | 15A | T3 10.0 | M1 40.0 | 4.00 | 480 | 1.4959 | 9590 | 230 | 41 |
| | 19A | T4 5.0 | M1 45.0 | 9.00 | 40 | 1.4740 | 9210 | 194 | 27 |
| | 20A | T4 7.5 | M1 42.5 | 5.67 | 190 | 1.4853 | 9540 | 195 | 24 |
| | 21A | T4 10.0 | M1 40.0 | 4.00 | 1260 | 1.4974 | 9780 | 202 | 27 |
| | 25A | T5 5.0 | M1 45.0 | 9.00 | 21 | 1.4627 | 10160 | 221 | 31 |
| | 26A | T5 7.5 | M1 42.5 | 5.67 | 47 | 1.4681 | 10880 | 213 | 24 |
| | 27A | T5 10.0 | M1 40.0 | 4.00 | 121 | 1.4735 | 11420 | 233 | 28 |
| Comparative Example | 1A | — | — | — | 6 | 1.4522 | 9350 | 178 | 19 |

TABLE 2

| | | Preparation ratio | | | Monomer properties | | Cured product properties | | |
| --- | --- | --- | --- | --- | --- | --- | --- | --- | --- |
| | | thiol (pbW) | methacrylate (pbW) | M/T (pbW/pbW) | Viscosity [mPa · s] | Refractive index | Elastic modulus [MPa] | Breaking strength [MPa] | Breaking energy [mJ] |
| Example | 4A | T1 5.0 | M2 45.0 | 9.00 | 38 | 1.4702 | 8270 | 212 | 34 |
| | 5A | T1 7.5 | M2 42.5 | 5.67 | 87 | 1.476 | 9700 | 211 | 36 |

TABLE 2-continued

| | | Preparation ratio | | | Monomer properties | | Cured product properties | | |
|---|---|---|---|---|---|---|---|---|---|
| | | thiol (pbW) | methacrylate (pbW) | M/T (pbW/pbW) | Viscosity [mPa·s] | Refractive index | Elastic modulus [MPa] | Breaking strength [MPa] | Breaking energy [mJ] |
| | 6A | T1 10.0 | M2 40.0 | 4.00 | 225 | 1.4815 | 9350 | 209 | 36 |
| | 10A | T2 5.0 | M2 45.0 | 9.00 | 31 | 1.4692 | 9560 | 222 | 36 |
| | 11A | T2 7.5 | M2 42.5 | 5.67 | 64 | 1.4744 | 10190 | 237 | 43 |
| | 12A | T2 10.0 | M2 40.0 | 4.00 | 132 | 1.4792 | 10020 | 223 | 36 |
| | 16A | T3 5.0 | M2 45.0 | 9.00 | 44 | 1.4803 | 9580 | 252 | 61 |
| | 17A | T3 7.5 | M2 42.5 | 5.67 | 140 | 1.4917 | 9210 | 220 | 42 |
| | 18A | T3 10.0 | M2 40.0 | 4.00 | 590 | 1.5034 | 9380 | 238 | 56 |
| | 22A | T4 5.0 | M2 45.0 | 9.00 | 60 | 1.4817 | 8000 | 204 | 41 |
| | 23A | T4 7.5 | M2 42.5 | 5.67 | 220 | 1.4927 | 8250 | 213 | 43 |
| | 24A | T4 10.0 | M2 40.0 | 4.00 | 3200 | 1.5048 | 8510 | 209 | 41 |
| | 28A | T5 5.0 | M2 45.0 | 9.00 | 16 | 1.4667 | 10250 | 236 | 39 |
| | 29A | T5 7.5 | M2 42.5 | 5.67 | 22 | 1.4706 | 10290 | 251 | 43 |
| | 30A | T5 10.0 | M2 40.0 | 4.00 | 26 | 1.4730 | 10250 | 223 | 33 |
| Comparative Example | 2A | — | — | — | 9 | 1.4592 | 8810 | 200 | 32 |

TABLE 3

| | | Preparation ratio | | | Monomer properties | | Cured product properties | | |
|---|---|---|---|---|---|---|---|---|---|
| | | thiol (pbW) | methacrylate (pbW) | M/T (pbW/pbW) | Viscosity [mPa·s] | Refractive index | Elastic modulus [MPa] | Breaking strength [MPa] | Breaking energy [mJ] |
| Example | 31A | T6 5.0 | M1 45.0 | 9.00 | 19 | 1.4700 | 11690 | 232 | 43 |
| | 32A | T6 10.0 | M1 40.0 | 4.00 | 102 | 1.4892 | 10182 | 222 | 31 |
| | 33A | T7 5.0 | M1 45.0 | 9.00 | 19 | 1.4642 | 10780 | 238 | 29 |
| | 34A | T7 10.0 | M1 40.0 | 4.00 | 91 | 1.4765 | 11040 | 238 | 30 |
| | 35A | T8 5.0 | M1 45.0 | 9.00 | 18 | 1.4624 | 11000 | 234 | 27 |
| | 36A | T8 10.0 | M1 40.0 | 4.00 | 78 | 1.4727 | 10670 | 228 | 29 |
| | 37A | T9 5.0 | M1 45.0 | 9.00 | 22 | 1.4645 | 11000 | 234 | 27 |
| | 38A | T9 10.0 | M1 40.0 | 4.00 | 130 | 1.4775 | 9920 | 208 | 24 |
| | 39A | T10 5.0 | M1 45.0 | 9.00 | 16 | 1.4604 | 9310 | 205 | 25 |
| | 40A | T10 10.0 | M1 40.0 | 4.00 | 59 | 1.4687 | 9370 | 193 | 26 |
| | 41A | T11 5.0 | M1 45.0 | 9.00 | 14 | 1.4599 | 11010 | 241 | 30 |
| | 42A | T11 10.0 | M1 40.0 | 4.00 | 8 | 1.4621 | 11350 | 282 | 49 |
| Comparative Example | 1A | — | — | — | 6 | 1.4522 | 9350 | 178 | 19 |

TABLE 4

| | | Preparation ratio | | | Monomer properties | | Cured product properties | | |
|---|---|---|---|---|---|---|---|---|---|
| | | thiol (pbW) | methacrylate (pbW) | M/T (pbW/pbW) | Viscosity [mPa·s] | Refractive index | Elastic modulus [MPa] | Breaking strength [MPa] | Breaking energy [mJ] |
| Example | 43A | T6 5.0 | M2 45.0 | 9.00 | 28 | 1.4769 | 10330 | 251 | 32 |
| | 44A | T7 5.0 | M2 45.0 | 9.00 | 30 | 1.4710 | 8970 | 205 | 33 |
| | 45A | T8 5.0 | M2 45.0 | 9.00 | 26 | 1.4686 | 8970 | 205 | 33 |
| | 46A | T9 5.0 | M2 45.0 | 9.00 | 23 | 1.4667 | 8820 | 202 | 33 |
| | 47A | T10 5.0 | M2 45.0 | 9.00 | 22 | 1.4666 | 10640 | 237 | 35 |
| | 48A | T11 5.0 | M2 45.0 | 9.00 | 24 | 1.4668 | 10770 | 206 | 32 |
| Comparative Example | 2A | — | — | — | 9 | 1.4592 | 8810 | 200 | 32 |

TABLE 5

| | | Preparation ratio | | | Monomer properties | | Cured product properties | | |
|---|---|---|---|---|---|---|---|---|---|
| | | thiol (pbW) | methacrylate (pbW) | M/T (pbW/pbW) | Viscosity [mPa·s] | Refractive index | Elastic modulus [MPa] | Breaking strength [MPa] | Breaking energy [mJ] |
| Example | 49A | T2 2.5  T3 2.5 | M1 45.0 | 9.00 | 28 | 1.4682 | 11370 | 221 | 21 |
| Comparative Example | 1A | — | — | — | 6 | 1.4522 | 9350 | 178 | 19 |

TABLE 6

| | | Preparation ratio | | | Monomer properties | | Cured product properties | | |
|---|---|---|---|---|---|---|---|---|---|
| | | thiol (pbW) | methacrylate (pbW) | M/T (pbW/pbW) | Viscosity [mPa·s] | Refractive index | Elastic modulus [MPa] | Breaking strength [MPa] | Breaking energy [mJ] |
| Example | 50A | T2 5.0 | M1 22.5   M2 22.5 | 9.00 | 144 | 1.4762 | 7910 | 228 | 61 |
| Comparative Example | 3A | — | — | — | 7 | 1.4552 | 7900 | 197 | 33 |

T1 to T10, M1 and M2 in Tables 1 to 6 are as follows.
T1: pentaerythritol tetrakis(3-mercaptopropionate)
T2: trimethylolpropane tris(3-mercaptopropionate)
T3: 4-mercaptomethyl-1,8-dimercapto-3,6-dithiaoctane
T4: a mixture of 5,7-dimercaptomethyl-1,11-dimercapto-3,6,9-trithiandecan, 4,7-dimercaptomethyl-1,11-dimercapto-3,6,9-trithiandecan, and 4,8-dimercaptomethyl-1,11-dimercapto-3,6,9-trithiaundecane
T5: tris-[(3-mercaptopropionyloxy)-ethyl]-isocyanurate
T6: 3,7-dithia-1,9-nonanedithiol
T7: 3,6-dioxa-1,8-octanedithiol
T8: 1,4-butanediol bis(thioglycolate)
T9: 1,8-octanedithiol
T10: 1,4-bis(3-mercaptobutylyloxy)butane
T11: bis(3-mercaptopropionic acid)ethylene glycol
M1: neopentyldimethacrylate
M2: triethylene glycol dimethacrylate Further, in Tables 1 to 6, "pbw" means a part by mass, and M/T means thiol/methacrylate.

As shown in Tables 1 to 6, the monomer compositions of Examples 1A to 50A had excellent breaking strength and breaking energy, that is, had excellent toughness, when made into molded bodies as compared with the monomer compositions of Comparative Examples 1A to 3A. More specifically, it was found that the monomer compositions prepared in combination of the thiourethane acrylate monomer which was a main component monomer and the enethiol methacrylate which was a diluting monomer, had excellent handleability while suppressing the decrease in function of the main component monomer due to the diluting monomer.

More specifically, as shown in Tables 1 and 3, by making a comparison between the monomer compositions of Examples 1A to 3A, 7A to 9A, 13A to 15A, 19A to 21A, 25A to 27A and 31A to 42A, and the monomer composition of Comparative Example 1A, which were common in that M1 was used, it was found that in each example, at least one of the breaking strength and the breaking energy when made into a molded body was excellent.

Further, as shown in Tables 2 and 4, by making a comparison between the monomer compositions of Examples 4A to 6A, 10A to 12A, 16A to 18A, 22A to 24A, 28A to 30A and 43A to 48A, and the monomer composition of Comparative Example 2A, which were common in that M2 was used, it was found that in each example, at least one of the breaking strength and the breaking energy when made into a molded body was excellent.

Further, as shown in Tables 5 and 6, by comparing the monomer compositions of Examples 49A and 50A using two kinds of thiol compounds or (meth)acrylate compounds with the monomer compositions of Comparative Examples 1A and 3A, respectively, it was found that in each example, at least one of the breaking strength and the breaking energy when made into a molded body was excellent.

Example 1B 0.04 parts by mass of TBP, 7.5 parts by mass of THIOL 1, and 42.5 parts by mass of 3G were charged in a 100 mL 4-neck flask equipped with a well-dried stirring blade and a thermometer, and after dissolving them to make a homogeneous solution, the temperature of the solution was raised to 40° C. After raising the temperature, the reaction was carried out for 3 hours while maintaining the reaction temperature at 40° C. At this time, the progress of the reaction was followed by IR analysis to confirm the end point of the reaction. By discharging the product from the reactor, 50 g of ene-thiol methacrylate (A-1) was obtained. The viscosity at 25° C. was 140 mPa·s. The refractive index at 25° C. was 1.4917. 3.0 parts by mass of the obtained ene-thiol methacrylate (A-1) and 12.0 parts by mass of TUA were placed in a container and stirred at 50° C. until uniform to obtain a monomer composition (1). By using the obtained monomer composition (1), the composition (1) for a dental material, and the test piece (test piece for bending test) were obtained according to the methods described in the sections of (Preparation of Test Piece for Bending Test) and (Bending Test). When the bending test was carried out, the elastic modulus was 9210 MPa, the breaking strength was 220 MPa, and the breaking energy was 42 mJ.

Example 2B 50 g of ene-thiol methacrylate (A-2) was obtained in the same manner as Example 1B except that the reaction time was changed from 3 hours to 6 hours. The viscosity at 25° C. was 150 mPa·s. The refractive index at 25° C. was 1.4917. 3.0 parts by mass of the obtained ene-thiol methacrylate (A-2) and 12.0 parts by mass of TUA were placed in a container and stirred at 50° C. until uniform to obtain a monomer composition (2). By using the obtained monomer composition (2), the composition (2) for a dental material, and the test piece (test piece for bending test) were obtained according to the methods described in the sections of (Preparation of Test Piece for Bending Test) and (Bending Test). When the bending test was carried out, the elastic modulus was 9240 MPa, the breaking strength was 218 MPa, and the breaking energy was 41 mJ.

Example 3B 50 g of ene-thiol methacrylate (A-3) was obtained in the same manner as Example 1B except that the reaction temperature was changed from 40° C. to 50° C. The viscosity at 25° C. was 300 mPa·s. The refractive index at 25° C. was 1.4917. 3.0 parts by mass of the obtained ene-thiol methacrylate (A-3) and 12.0 parts by mass of TUA were placed in a container and stirred at 50° C. until uniform to obtain a monomer composition (3). By using the obtained monomer composition (3), the composition (3) for a dental material, and the test piece (test piece for bending test) were obtained according to the methods described in the sections of (Preparation of Test Piece for Bending Test) and (Bending Test). When the bending test was carried out, the elastic modulus was 9200 MPa, the breaking strength was 221 MPa, and the breaking energy was 42 mJ.

Example 4B 50 g of ene-thiol methacrylate (A-4) was obtained in the same manner as Example 1B except that the reaction temperature was changed from 40° C. to 55° C. The viscosity at 25° C. was 600 mPa·s. The refractive index at 25° C. was 1.4917. 3.0 parts by mass of the obtained ene-thiol methacrylate (A-4) and 12.0 parts by mass of TUA were placed in a container and stirred at 50° C. until uniform to obtain a monomer composition (4). By using the obtained monomer composition (4), the composition (4) for a dental material, and the test piece (test piece for bending test) were obtained according to the methods described in the sections of (Preparation of Test Piece for Bending Test) and (Bending Test). When the bending test was carried out, the elastic modulus was 9160 MPa, the breaking strength was 215 MPa, and the breaking energy was 40 mJ.

Examples 5B to 13B 50 g of ene-thiol methacrylates (A-5) to (A-13) were obtained in the same manner as Example 1B except that the thiol compounds and the (meth)acrylate compounds were changed to the compound shown in Table 7. The viscosity at 25° C. and the refractive index at 25° C. are shown in Table 7. A monomer compositions (5) to (13) were obtained in the same manner as Example 1B except that ene-thiol methacrylate (A-1) was respectively changed to ene-thiol methacrylates (A-5) to (A-13). By using the obtained monomer compositions (5) to (13), the compositions (5) to (13) for a dental material, and the test piece (test piece for bending test) were obtained according to the methods described in the sections of (Preparation of Test Piece for Bending Test) and (Bending Test), and then the bending test was carried out. The elastic modulus, the breaking strength, and the breaking energy are shown in Table 7.

Comparative Example 1B 0.04 parts by mass of TPP, 7.5 parts by mass of THIOL 1, and 42.5 parts by mass of 3G were charged in a 100 mL 4-neck flask equipped with a well-dried stirring blade and a thermometer, and after dissolving them to make a homogeneous solution, the temperature of the solution was raised to 40° C. After raising the temperature, the reaction was carried out for 3 hours while maintaining the reaction temperature at 50° C. At this time, the end point of the reaction was attempted to confirm by following the progress of the reaction by IR analysis, but the reaction did not end.

Comparative Example 2B

The synthesis of the ene-thiol methacrylate was attempted in the same manner as Comparative Example 1B except that the reaction time was changed from 3 hours to 6 hours. At this time, the end point of the reaction was attempted to confirm by following the progress of the reaction by IR analysis, but the reaction did not end.

Comparative Example 3B

The synthesis of the ene-thiol methacrylate was attempted in the same manner as Comparative Example 1B except that the reaction time was changed from 3 hours to 12 hours. At this time, the end point of the reaction was attempted to confirm by following the progress of the reaction by IR analysis, but the reaction did not end.

Comparative Example 4B

The synthesis of the ene-thiol methacrylate was attempted in the same manner as Comparative Example 1B except that the reaction temperature was changed from 40° C. to 60° C. About 20 minutes after the reaction started, mixture rapidly thickened and became a gel-like solid. It was not possible to discharge the product, which is the gel-like solid, from the reactor.

a diluting monomer, had excellent handleability while suppressing the decrease in function of the main component monomer due to the diluting monomer.

The disclosures of Japanese Patent Application No. 2018-154941 filed on Aug. 21, 2018, Japanese Patent Application No. 2018-154942 filed on Aug. 21, 2018, and Japanese Patent Application No. 2018-154943 filed on Aug. 21, 2018, are hereby incorporated by reference in its entirety.

All the documents, patent applications and technical standards that are described in the present specification are hereby incorporated by reference to the same extent as if each individual document, patent application or technical standard is concretely and individually described to be incorporated by reference.

The invention claimed is:

1. A method of manufacturing a (meth)acrylate, the method comprising:
preparing a composition comprising a thiol compound containing two or more thiol groups, a (meth)acrylate compound containing two or more (meth)acryloyloxy groups, and an alkylphosphine compound; and

TABLE 7

| | | Preparation conditions | | | | Monomer properties | | Cured product properties | | | Presence of absence reaction of progress | Presence or absence of gelation |
|---|---|---|---|---|---|---|---|---|---|---|---|---|
| | | Catalyst | Thiol | Meth-acrylate | Reaction temperature [° C.] | Reaction time [hour] | Viscosity [mPa·s] | Refractive index | Elastic modulus [MPa] | Breaking strength [MPa] | Breaking energy [mJ] | | |
| Example | 1B | TBP | THIOL 1 | 3G | 40 | 3 | 140 | 1.4917 | 9210 | 220 | 42 | Presence | Absence |
| | 2B | TBP | THIOL 1 | 3G | 40 | 6 | 150 | 1.4917 | 9240 | 218 | 41 | Presence | Absence |
| | 3B | TBP | THIOL 1 | 3G | 50 | 3 | 300 | 1.4917 | 9200 | 221 | 42 | Presence | Absence |
| | 4B | TBP | THIOL 1 | 3G | 55 | 3 | 600 | 1.4917 | 9160 | 215 | 40 | Presence | Absence |
| | 5B | TBP | THIOL 2 | 3G | 40 | 3 | 220 | 1.4927 | 8250 | 213 | 43 | Presence | Absence |
| | 6B | TBP | THIOL 3 | 3G | 40 | 3 | 87 | 1.476 | 9700 | 211 | 36 | Presence | Absence |
| | 7B | TBP | THIOL 4 | 3G | 40 | 3 | 64 | 1.4744 | 10190 | 237 | 43 | Presence | Absence |
| | 8B | TBP | THIOL 5 | 3G | 40 | 3 | 22 | 1.4706 | 10290 | 251 | 43 | Presence | Absence |
| | 9B | TBP | THIOL 1 | NPG | 40 | 3 | 110 | 1.4846 | 9330 | 213 | 27 | Presence | Absence |
| | 10B | TBP | THIOL 2 | NPG | 40 | 3 | 190 | 1.4853 | 9540 | 195 | 24 | Presence | Absence |
| | 11B | TBP | THIOL 3 | NPG | 40 | 3 | 84 | 1.4698 | 9370 | 247 | 53 | Presence | Absence |
| | 12B | TBP | THIOL 4 | NPG | 40 | 3 | 51 | 1.4681 | 8710 | 196 | 28 | Presence | Absence |
| | 13B | TBP | THIOL 5 | NPG | 40 | 3 | 47 | 1.4681 | 10880 | 213 | 24 | Presence | Absence |
| Comparative Example | 1B | TPP | THIOL 1 | 3G | 40 | 3 | — | — | — | — | — | Absence | Absence |
| | 2B | TPP | THIOL 1 | 3G | 40 | 6 | — | — | — | — | — | Absence | Absence |
| | 3B | TPP | THIOL 1 | 3G | 40 | 12 | — | — | — | — | — | Absence | Absence |
| | 4B | TPP | THIOL 1 | 3G | 60 | 1 | — | — | — | — | — | Presence | Absence |

As shown in Table 7, in Examples 1B to 13B, the (meth)acrylate could be produced. On the other hand, in Comparative Examples 1B to 3B, the (meth)acrylate could not be produced. Further, in Comparative Example 4B, the obtained product was gelled, and this product could not be used as a diluting monomer of the monomer composition.

The monomer compositions of Examples 1B to 8B had excellent breaking strength and breaking energy, that is, had excellent toughness, when made into molded bodies as compared with the monomer composition of Comparative Example 2A. The monomer compositions of Examples 9B to 13B had excellent breaking strength and breaking energy, that is, had excellent toughness, when made into molded bodies as compared with the monomer composition of Comparative Example TA. More specifically, it was found that the monomer compositions prepared in combination of the thiourethane acrylate monomer which was a main component monomer and the ene-thiol methacrylate which was producing a (meth)acrylate (A) containing a sulfide bond by reacting the thiol compound and the (meth)acrylate compound,
wherein the alkylphosphine compound comprises a trialkylphosphine compound, and
wherein the (meth)acrylate (A) comprises a structure formed by reacting the thiol groups contained in the thiol compound and the (meth)acryloyloxy groups contained in the (meth)acrylate compound, and wherein the (meth)acrylate (A) does not contain a thiol group, and contains a (meth)acryloyloxy group.

2. The method of manufacturing the (meth)acrylate according to claim 1, wherein a content of the alkylphosphine compound is 0.2 parts by mass or less with respect to 100 parts by mass of the composition.

3. The method of manufacturing the (meth)acrylate according to claim 1, wherein a reaction temperature of the thiol compound and the (meth)acrylate compound is 50° C. or less when producing the (meth)acrylate (A).

4. The method of manufacturing the (meth)acrylate according to claim 1, wherein the trialkylphosphine compound comprises at least one selected from the group consisting of tri-n-butylphosphine, tri-n-hexylphosphine, tricyclohexylphosphine and tri-n-octylphosphine.

5. The method of manufacturing the (meth)acrylate according to claim 1, wherein the (meth)acrylate (A) comprises a structure represented by the following general formula (B), and two or more (meth)acryloyloxy groups in a molecule:

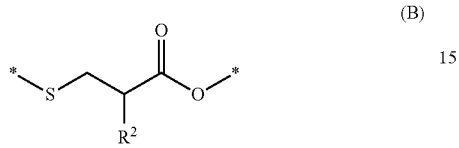

(B)

wherein, in the general formula (B), $R^2$ represents a hydrogen atom or a methyl group; and each * represents a binding site.

6. The method of manufacturing the (meth)acrylate according to claim 1, wherein the (meth)acrylate (A) is represented by the following general formula (1):

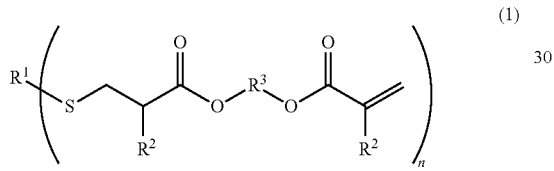

(1)

wherein, in the general formula (1), $R^1$ represents a residue of a bifunctional to tetrafunctional thiol compound from which all thiol groups have been removed; $R^2$ represents a hydrogen atom or a methyl group; $R^3$ represents a residue of a di(meth)acrylate from which two (meth)acryloyloxy groups have been removed; n is an integer from 2 to 4; and plural instances of $R^2$ and $R^3$ may be the same or different, respectively.

7. The method of manufacturing the (meth)acrylate according to claim 6, wherein a molecular weight of $R^1$ is from 100 to 500 in the general formula (1).

8. The method of manufacturing the (meth)acrylate according to claim 6, wherein $R^1$ is a group represented by the following formula (2), (3), (4), (5), (6-1), (6-2), (6-3), (7), (8), (9) or (10) in the general formula (1):

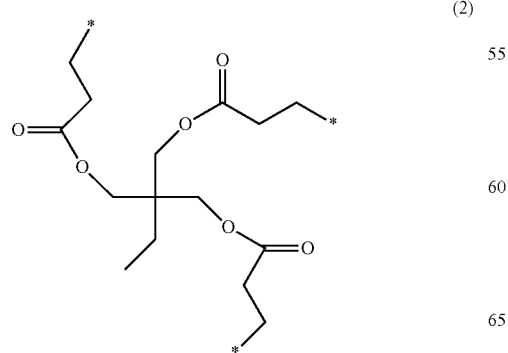

(2)

-continued

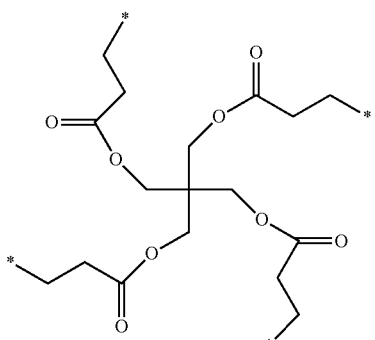

(3)

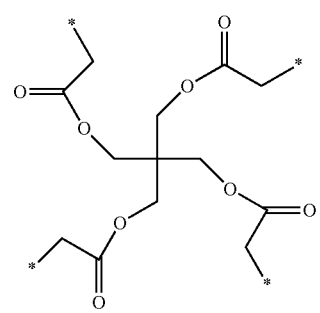

(4)

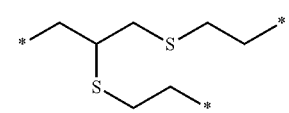

(5)

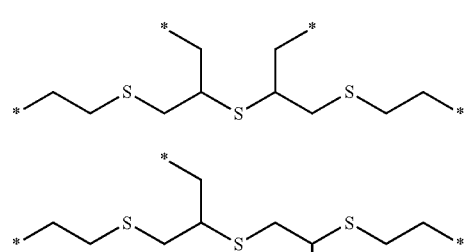

(6-1)

(6-2)

(6-3)

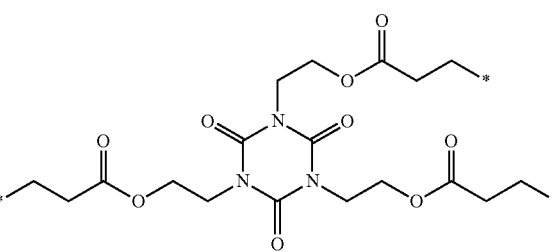

(7)

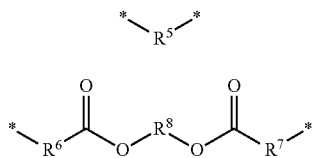

(8)

(9)

-continued

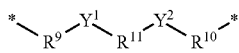
(10)

wherein, in formulae (2), (3), (4), (5), (6-1), (6-2), (6-3), (7), (8), (9) and (10), each * represents a binding site; in formula (8), $R^5$ represents a divalent hydrocarbon group having 1 to 10 carbon atoms; in formula (9), $R^6$, $R^7$, and $R^8$ each independently represent a divalent hydrocarbon group having 1 to 10 carbon atoms; in formula (10), $R^9$, $R^{10}$, and $R^{11}$ each independently represent a divalent hydrocarbon group having 1 to 10 carbon atoms; and $Y^1$ and $Y^2$ each independently represent an oxygen atom or a sulfur atom.

9. The method of manufacturing the (meth)acrylate according to claim 6, wherein, in general formula (1), the di(meth)acrylate is neopentyl di(meth)acrylate, 1,4-butanediol di(meth)acrylate, 1,6-hexanediol di(meth)acrylate, 1,8-octanediol di(meth)acrylate, 1,9-nonanediol di(meth)acrylate, 1,10-decanediol di(meth)acrylate, tricyclodecanedimethanol di(meth)acrylate, ethylene glycol di(meth)acrylate, diethylene glycol di(meth)acrylate, triethylene glycol di(meth)acrylate, tetraethylene glycol di(meth)acrylate, polyethylene glycol di(meth)acrylate, tripropylene glycol di(meth)acrylate, tetrapropylene glycol di(meth)acrylate, polypropylene glycol di(meth)acrylate, 2,2-bis[4-(3-(meth)acryloyloxy-2-hydroxypropoxy)phenyl]propane, ethylene oxide-modified bisphenol A di(meth)acrylate, or propylene oxide-modified bisphenol A di(meth)acrylate.

10. The method of manufacturing the (meth)acrylate according to claim 1, wherein the (meth)acrylate (A) has a viscosity at 25° C. of from 1 mPa·s to 10,000 mPa·s.

* * * * *